(12) United States Patent
d'Adda di Fagagna et al.

(10) Patent No.: US 12,234,455 B2
(45) Date of Patent: Feb. 25, 2025

(54) THERAPEUTIC OLIGONUCLEOTIDES

(71) Applicant: IFOM—FONDAZIONE ISTITUTO FIRC DI ONCOLOGIA MOLECOLARE, Milan (IT)

(72) Inventors: Fabrizio d'Adda di Fagagna, Milan (IT); Francesca Rossiello, Milan (IT); Julio Aguado, Milan (IT); Corey Jones-Weinert, Milan (IT)

(73) Assignee: IFOM—FONDAZIONE ISTITUTO FIRC DI ONCOLOGIA MOLECOLARE, Milan (IT)

(*) Notice: Subject to any disclaimer, the term of this patent is extended or adjusted under 35 U.S.C. 154(b) by 228 days.

(21) Appl. No.: 17/065,409

(22) Filed: Oct. 7, 2020

(65) Prior Publication Data
US 2021/0087567 A1 Mar. 25, 2021

Related U.S. Application Data

(63) Continuation of application No. 15/748,133, filed as application No. PCT/EP2016/068162 on Jul. 29, 2016, now abandoned.

(30) Foreign Application Priority Data

Jul. 29, 2015 (EP) ..................... 15178809

(51) Int. Cl.
C07H 21/02 (2006.01)
C07H 21/04 (2006.01)
C12N 15/113 (2010.01)

(52) U.S. Cl.
CPC ...... *C12N 15/113* (2013.01); *C12N 2310/113* (2013.01); *C12N 2310/314* (2013.01); *C12N 2310/315* (2013.01); *C12N 2310/321* (2013.01); *C12N 2310/3231* (2013.01); *C12N 2310/3233* (2013.01); *C12N 2310/341* (2013.01); *C12N 2310/3521* (2013.01); *C12N 2310/3525* (2013.01)

(58) Field of Classification Search
CPC .......................... C12N 15/113; C12N 2310/11
See application file for complete search history.

(56) References Cited

U.S. PATENT DOCUMENTS

| | | | | |
|---|---|---|---|---|
| 6,046,307 A | * | 4/2000 | Shay ................... | C07K 14/003 530/324 |
| 8,999,643 B2 | * | 4/2015 | Reddel ................. | C12Q 1/6883 435/6.12 |
| 2007/0270363 A1 | | 11/2007 | Bennett et al. | |

FOREIGN PATENT DOCUMENTS

WO WO 2013/167744 A1 11/2013

OTHER PUBLICATIONS

Elayadi et al. (Current Opinion in Investigational Drugs, 2001, 2(4), 1-5).*
Shay (Clinical Cancer Research, vol. 9, 3521-3525, 2003).*
Henson et al. (Oncogene (2002) 21, 598-610).*
Aguado et al. "Inhibition of DNA damage response at telomeres improves the detrimental phenotypes of Hutchinson-Gilford Progeria Syndrome". Nature Communications. 10, 4990, pp. 1-11, 2019.
Armanios et al.: "The telomere syndromes", Nature Reviews Genetics, vol. 13, No. 10, Sep. 11, 2012, pp. 693-704.
Benson et al.: "Role of progerin-induced telomere dysfunction in HGPS premature cellular senescence", Journal of Cell Science, vol. 123, No. 15, Jul. 6, 2010, pp. 2605-2612.
Conomos et al.: "Variant repeats are interspersed throughout the telomeres and recruit nuclear receptors in ALT cells", Journal of Biological Chemistry, vol. 282, No. 40, 1 O Dec. 2012, pp. 893-906.
Crees et al.: "Oligonucleotides and G-quadruplex stabilizers: targeting telomeres and telomerase in cancer therapy", Current Pharmaceutical Design, vol. 20, No. 41, Dec. 1, 2014, pp. 6422-6437.
Draskovic et al.: "Telomere recombination and the ALT pathway: a therapeutic perspective for cancer", Current Pharmaceutical Design, vol. 20, No. 41, Dec. 1, 2014, pp. 6466-6471.
Elayadi A. et al.: "Implications of high-affinity hybridization by Locked Nucleic Acid oligomers for inhibition of human Telomerase", Biochemistry, American Chemical Society, US, vol. 41, No. 31, Jan. 1, 2002, pp. 9973-9981.
Folini et al.: "Targeting Telomerase by antisense-based approaches: perspectives for new anti-cancer therapies", Current Pharmaceutical Design, vol. 11, No. 9, Apr. 1, 2005, pp. 1105-1117.
Folini et al.: "Telomeres as targets for anticancer therapies", Expert Opinion on Therapeutic Targets, Feb. 3, 2011, pp. 1-15.
Liu et al. "Structural transformation induced by locked nucleic acid or 2'-O_methyl nucleic acid site-specific modifications on thrombin binding aptamer". Chemistry Central Journal, 8:19, pp. 1-6, 2014.
Lovejoy et al.: "Loss of ATRX, genome instability, and an altered DNA damage response are hallmarks of the alternative lengthening of telomeres pathway", PLOS Genetics, vol. 8, No. 7, Jul. 19, 2012, p. e1002772.
Potts et al.: "The SMC5/6 complex maintains telomere length in ALT cancer cells through SUMOylation of telomere-binding proteins", Nature Structural & Molecular Biology, vol. 14, No. 7, Jul. 2007, pp. 581-590.
Santambrogio et al.: "MicroRNA-dependent regulation of telomere maintenance mechanisms: a field as much unexplored as potentially promising", Current Pharmaceutical Design, vol. 20, No. 41, Dec. 1, 2014, pp. 6404-6421.

(Continued)

*Primary Examiner* — Amy Rose Hudson
(74) *Attorney, Agent, or Firm* — Lucas & Mercanti, LLP

(57) ABSTRACT

The present invention relates to an oligonucleotide comprising one of the following sequence: (TTAGGG) SEQ ID No. 1, (TAGGGT) SEQ ID No. 2, (AGGGTT) SEQ ID No. 3, (GGGTTA) SEQ ID No. 4, (GGTTAG) SEQ ID No. 5 or (GTTAGG) SEQ ID No. 6 or a complementary sequence thereof or a fragment or a variant or a mixture thereof for use in the treatment and/or prevention of a disease characterized by alternative lengthening of telomeres or a non-cancer condition associated with telomere dysfunction and relative pharmaceutical compositions and to relative pharmaceutical composition and method.

12 Claims, 21 Drawing Sheets

Figure 1:
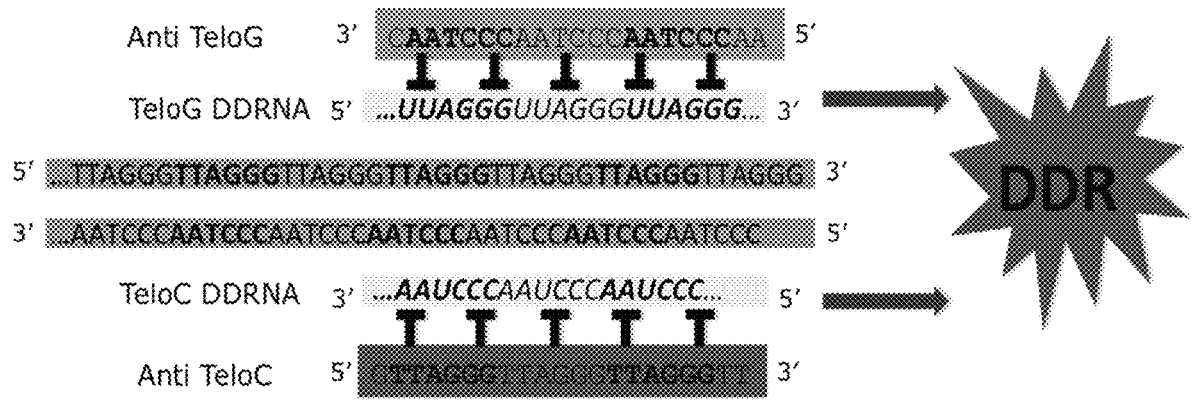

Specification includes a Sequence Listing.

(56) References Cited

OTHER PUBLICATIONS

Tamura Y. et al. : "Inhibition of human telomerase activity by antisense phosphorothioate oligonucleotides encapsulated with the transfection reagent, FuGENE6, in HeLa cells", Antisense & Nucleic Acid Drug Development, vol. 10, No. 2, Apr. 2000, pp. 87-96.

\* cited by examiner a.

b.

A

B

THERAPEUTIC OLIGONUCLEOTIDES

RELATED CASES

This application is a continuation of U.S. patent application Ser. No. 15/748,133, filed on Jan. 26, 2018, which is the U.S. National Phase under 35 U.S.C. § 171 of International Patent Application No. PCT/EP2016/068162, filed Jul. 29, 2016, which claims priority to European Patent Application No. EP 15178809.8, filed Jul. 29, 2015, the entire content of each of which is incorporated by reference herein.

Reference to Sequence Listing Submitted Electronically Via PATENT CENTER

The content of the electronically submitted sequence listing, file name: 128-1280 ReplacementSeqListing.txt; size: 6,752 bytes; and date of creation: Oct. 17, 2024, filed herewith, is incorporated herein by reference in its entirety.

TECHNICAL FIELD

The present invention relates to an oligonucleotide comprising one of the following sequence: (TTAGGG) SEQ ID No. 1, (TAGGGT) SEQ ID No. 2, (AGGGTT) SEQ ID No. 3, (GGGTTA) SEQ ID No. 4, (GGTTAG) SEQ ID No. 5 or (GTTAGG) SEQ ID No. 6 or a complementary sequence thereof or a fragment or a variant or a mixture thereof for use in the treatment and/or prevention of a disease characterized by alternative lengthening of telomeres or a non-cancer condition associated with telomere dysfunction and relative pharmaceutical compositions and to relative pharmaceutical composition and method.

BACKGROUND

DNA is a unique type of molecule in a cell in that, if damaged, it cannot be replaced. The so-called "DNA damage response" (DDR) is a coordinated set of evolutionarily-conserved events that, when triggered upon DNA damage detection, arrests the cell cycle (DNA damage checkpoint function) and coordinates DNA repair (Jackson and Bartek, 2009). DNA damage is a physiological event. Ageing and cancer are probably the two best examples in mammals that highlight the relevance of DNA damage accumulation, DDR activation and its consequences. Significant contribution has been made to the understanding of DDR engagement both in ageing and in cancer (d'Adda di Fagagna, 2008; Jackson and Bartek, 2009).

More recently, the present inventors have unveiled and reported that full DDR activation depends on RNA molecules. They observed that DNA double-strand breaks (DSBs) trigger the local generation of non-coding RNAs at the site of DNA damage carrying the sequence surrounding the damaged site. They have also shown that these RNA (the authors called them DDRNAs) are essential for DDR activation. Indeed, removal of DDRNA by RNase A treatment inhibits DDR activation, and DDR can be fully restored by the addition of chemically-synthesized DDRNA carrying the sequence surrounding the damaged site but not other sequences (Francia et al., 2012).

Several studies have shown that RNA functions can be inhibited by the use of inhibitory antisense oligonucleotides (ASOs) that act by pairing with target RNAs and thus impairing their functions. Their use is successfully reaching the clinical stage (Janssen et al., 2013; Li and Rana, 2014; Monteleone et al., 2015; Stenvang et al., 2012). Cancer cells must preserve telomere length and counteract natural telomere attrition to retain unlimited proliferative potential. Most cancers cells achieve this by reactivating telomerase expression, an enzyme that elongates short telomeres. However, 10-15% of all human tumors, with a higher incidence in, but not exclusively, osteosarcomas, soft tissue sarcomas, primary brain tumors, glioblastoma multiforme (GBM) and neuroblastomas maintain telomere length by the so-called Alternative Lengthening of Telomeres (ALT) mechanism based on homologous recombination (HR) among telomeres (Cesare and Reddel, 2010; Durant, 2012; Henson and Reddel, 2010).

Although ALT tumors may carry different genetic mutations causative of their transformed and malignant state, most ALT cancer cells show mutations in DAXX and ATRX genes, thus making possible the classification of tumors as ALT by common genetic analyses (Heaphy et al., 2011).

ALT mechanisms have never been reported in healthy/normal cells (Cesare and Reddel, 2010). However, in addition to cancer, ALT mechanisms have been reported in EBV-infected cells (Kamranvar et al., 2013) highlighting the possibility that other viral infections may trigger such mechanisms.

The use of telomerase inhibitors in cancer therapy has been investigated widely (Ruden and Puri, 2013); however, an intrinsic limitation of this approach is that lack of telomerase activity in tumors can lead to the selection of ALT positive clones, as reported in (Hu et al., 2012). Differently, so far, no reversal from ALT to telomerase mechanisms of telomere maintenance have been reported.

ALT cells show chronic DDR activation at telomeres indicating the dysfunctional nature of telomeres in such cells. Critically short/dysfunctional telomeres are then elongated/"repaired" by DDR mechanism engaging HR pathways. ALT-associated PML bodies (APBs) contain telomeric DNA and DDR factors and are a known biomarker of ALT cells (Cesare and Reddel, 2010; Yeager et al., 1999). HR is a DNA repair mechanism part of DDR and it has been shown to be necessary for the maintenance of telomeres in ALT cells. The MRN (MRE11/RAD50/NBS1) complex is a key DDR factor involved in the HR pathway. Indeed, its inactivation by either overexpression of the inhibitory protein SP100 or short hairpin-mediated knockdown, determines the inhibition of the telomere maintenance specifically in the ALT-positive cells (Jiang et al., 2005; Jiang et al., 2007; Zhong et al., 2007). RNA interference-mediated depletion of the SMCS/6 complex, which promotes HR-mediated repair of DSBs, results in shortened telomeres and cellular senescence in ALT cells (Potts and Yu, 2007). RPA binds to single strand DNA during the initial phase of HR and its down-regulation through RNA interference causes impairment in ALT activity (Jiang et al., 2007). More recently, an ATR small molecule inhibitor has been shown to prevent cell growth specifically of ALT-positive cells (Flynn et al., 2015), although this specificity seems to be broader, including non-ALT cancer cells and only in combination with CHK1 inhibitors (Sanjiv et al., 2016). Consistently, another recent report suggested that the cell-type specificity of the ATR inhibitors is more related to the cell confluency than to the mechanism of telomere maintenance (http://biorxiv.org/content/early/2016/06/04/053280).

The inhibition of DDR and consequent recombination events at telomeres in ALT cells could be exploited to conceive novel potential therapeutic avenues for anticancer treatments. Consistently, as mentioned above, ALT cells have been proposed to be highly sensitive to the inhibition of the ATR kinase (Flynn et al., 2015), a protein involved in DDR signalling in the context of DNA repair by HR, although its specificity has been recently put into question (Sanjiv et al., 2016) and (http://biorxiv.org/content/early/2016/06/04/053280).

Similarly, conditions characterized by telomeric DNA damage often leading to a progeric phenotype (premature ageing), are expected to be associated with the generation of DDRNAs with a telomeric sequence.

WO2013/167744 relates to small RNAs molecules (DDRNAs) produced at a site of DNA damage and having the specific sequence of the damaged locus. The existence and generation of DDRNAs from telomeres in cells exhibiting ALT, such as ALT cancer cells, or in EBV-infected ALT cells or in cells from premature ageing conditions is not described neither it is suggested DDRNA inhibition as therapeutic rationale.

WO2014092609 relates to a method for influencing the proliferative status of cells using specific G-chain oligonucleotide sequences of human telomeric DNA.

US2013065950 discloses compounds comprising an oligonucleotide moiety covalently linked to a lipid moiety. The oligonucleotide moiety comprises a sequence that is complementary to the RNA component of human telomerase. The compounds inhibit telomerase activity in cells.

WO97/38013 does not refer specifically to a disease (in particular a cancer) characterized by alternative lengthening of telomeres (ALT) neither to a non-cancer condition characterized by dysfunctional telomeres. In addition, it relates to inhibition of telomerase. By contrast, the oligonucleotides of the present invention are not active on telomerase-positive cancer cells.

WO 2006/107949 refers to a method of treating oxidative stress disorders. The present invention relates to the specific treatment of ALT cancer cells and non-cancer conditions characterized by dysfunctional telomeres.

CN1936011 relates to a polycation liposome telomere enzyme antisense oligonucleotide compound that is made up of polycation liposome and antisense oligonucleotide.

WO2006028160 relates to phosphorothioate oligonucleotide conjugate which has high inhibitory activity against the telomerase contained in a human leukemic cell extract and which gives a stable duplex hybrid with a complementary DNA.

US2006183704 relates to methods for treating hyperproliferative disorders, including cancers, by administering to an affected mammal an effective amount of a composition comprising pTT or a composition comprising one or more oligonucleotides which share at least 50% nucleotide sequence identity with the human telomere overhang repeat.

WO01/74342 relates to methods of treatment or prevention of hyperproliferative diseases or precancerous conditions affecting epithelial cells, such as psoriasis, vitiligo, atopic dermatitis, or hyperproliferative or UV-responsive dermatoses, hyperproliferative or allergically mediated diseases of other epithelia and methods for reducing photoaging, or oxidative stress or for prophylaxis against or reduction in the likelihood of the development of skin cancer.

WO96/23508 discloses a method of inhibiting proliferation of cancer and other immortal type cellular disease states. The method includes introduction of synthetic oligonucleotides which mimic telomere motifs.

Sandra Sampl et al. (Proceedings: AACR Annual Meeting 2014; Apr. 5-9, 2014; Abstract 2743, San Diego, Calif.), indicate that RNA transcripts from telomeres called TERRA were identified to block telomerase activity (TA) potentially via direct binding to TERC. TERRA are constitutive single-stranded non-coding RNA, from around 100 bases up to at least 9 kilobases in length (Azzalin et al., 2007). They are transcribed starting from a promoter located in the subtelomeric region, thus they carry both subtelomeric and the G-rich telomeric sequences. Differently, DDRNAs are short RNA (at least 6 or 8 nucleotides long or between 10 and 50 nucleotides long, around 22 nucleotides long) that can potentially form double-stranded RNAs. They are generated by processing of precursor transcripts, which are transcribed from both telomeric strands, generating a G-rich and a C-rich telomeric repeats-containing RNA molecules, starting at the very end of telomeres or within telomeric repeats.

Therefore there is still the need for treatment of diseases characterized by alternative lengthening of telomeres and non-cancer conditions associated with telomere dysfunction.

SUMMARY OF THE INVENTION

The present invention is based on the discovery that upon telomeric DNA damage or dysfunction non-coding RNAs (named tDDRNAs) accumulate. These are RNA transcripts synthesized using a dysfunctional telomere as a template for transcription of a long RNA precursor, which can be then processed by Dicer and/or Drosha into shorter non-coding RNAs (tDDRNAs).

In the present invention it was surprisingly found that inhibitors of generation and/or synthesis and/or functions of tDDRNAs and their precursors also inhibit DDR activation and thus may be applied for the treatment of ALT-associated conditions and conditions associated with telomeric DNA damage or dysfunction.

Antisense oligonucleotides (ASOs), for instance in the form of locked nucleic acids (LNA) complementary to tDDRNAs and/or their precursors were synthetized, together with LNA with unrelated sequences as negative control. It was observed that telomeric ASOs can specifically inhibit DDR activation, inhibiting both signaling and ensuing DNA repair. With a sequence-specific ASO, results showing decreased cell proliferation specifically in ALT cells were obtained.

Telomeric DDR activation in ALT tumors may be targeted by sequence-specific ASOs, thus impairing telomere maintenance and reducing proliferation. The inventors synthesized LNA ASOs with the sequence complementary to telomeric RNAs generated upon telomere DNA damage or dysfunction. They observed that transfection of an ASO oligonucleotide carrying a specific telomeric sequence was able to strongly suppress the proliferation of ALT positive cell lines (i.e. osteosarcoma U-2 OS and G292 cell lines, glioblastoma GBM14 cell lines, fibroblasts WI38 VA13 and SW26) while the same amount of ASO with a different sequence not targeting telomeric RNA and not targeting any human sequence had no significant effect. Importantly, none of these ASOs has an impact on normal human fibroblasts (of mesenchymal origin like osteosarcomas) proliferation or on the proliferation of telomerase-positive cancer cells, as tested in parallel, suggesting that this approach is specific for ALT tumors and indicates that this treatment will not be toxic in living animals and human patients. At this stage, they have:

1) identified a new potential therapeutic agent;
2) defined a specific subset of tumors that might benefit from a treatment with this agent. Furthermore, ageing is associated with DDR activation especially at telomeres (d'Adda di Fagagna et al., 2003; Fumagalli et al., 2012; Herbig et al., 2006; Herbig et al., 2004; Hewitt et al., 2012). The Hutchinson-Gilford progeria syndrome (HGPS) (Pollex and Hegele, 2004) is one example of a progeria syndrome caused by a mutant form of lamin A, also called progerin. Progeria means premature ageing. HGPS progeric phenotypes can be suppressed by the expression of telomerase, by decreasing progerin-induced DNA-damage signaling (Kudlow et al., 2008). This indicates that the progeric phenotype of HGPS cells (and of HGPS patients by extension) is caused by dysfunctional telomeres causing DDR. Indeed DDR is found at the telomeres in HGPS cells (Benson et al., 2010; Chojnowski et al., 2015). The fish *Danio rerio* (zebrafish) is a simple vertebrate model, suitable for ageing studies. Indeed it has been shown that telomerase mutation accelerates physiological ageing by speeding up telomere shortening and consequent telomere dysfunction and DDR activation (Henriques et al., 2013). Specifically telomerase-mutant fish are characterized by shorter lifespan, tissue atrophy and decreased fertility. They represent a model of non-cancer condition associated with telomere dysfunction. By using LNA ASOs with the sequence complementary to tDDRNAs and their precursors generated upon telomere DNA damage or dysfunction the inventors prevented cellular senescence in progerin-expressing cells. Moreover they extended the lifespan of a mouse model for HGPS and of telomerase-mutant zebrafish, suggesting that they could suppress ageing-related phenotypes.

In the present invention, the inhibition of DDR through the inhibition of DDRNAs and/or their precursors have the great advantage to be sequence specific, thus minimizing the possibility of adverse side effects in normal cells due for instance by DDR inhibition away from telomeres.

Further, in the context of cancer therapeutics, these inhibitors may synergize with telomerase inhibitors in order to prevent the potential emergence of clones of cancer cells using ALT mechanism of telomere maintenance and thus resistant to telomerase inhibitions.

In fact, existing anticancer therapies are effective anticancer treatments that act by damaging the DNA of or inhibiting DDR in cancer cells. However the DNA damaging activity or the DDR inhibition of most of them is not sequence specific. The oligonucleotides of the present invention impair DDR in a sequence-specific manner, then they may also confer sequence specificity to existing DNA damaging treatments thus enhancing efficacy.

Therefore, the present invention provides an oligonucleotide comprising one of the following sequence:
(TTAGGG) SEQ ID No. 1, (TAGGGT) SEQ ID No. 2, (AGGGTT) SEQ ID No. 3, (GGGTTA) SEQ ID No. 4, (GGTTAG) SEQ ID No. 5 or (GTTAGG) SEQ ID No. 6 or a complementary sequence thereof or a fragment or a variant or a mixture thereof for use in the treatment and/or prevention of a disease characterized by alternative lengthening of telomeres. Preferably the oligonucleotide or a fragment or a variant thereof comprises one of the following sequence: $(TTAGGG)_n$, $(TAGGGT)_n$, $(AGGGTT)_n$, $(GGGTTA)_n$, $(GGTTAG)_n$ or $(GTTAGG)_n$ wherein $1<n<1000$, preferably $1<n<500$, preferably $1<n<200$, preferably $1<n<100$, preferably $1<n<50$, preferably $1<n<20$, preferably $1<n<10$, preferably $1<n<5$.

Preferably said oligonucleotide is complementary to the sequence of an RNA, said RNA being a RNA transcript synthesized using a specific dysfunctional telomeric DNA as a template for transcription or a fragment of said RNA transcript, said fragment (DDRNA) being generated by processing by Dicer and/or Drosha.

Preferably the disease is cancer or an Epstein-Bar virus infection. Still preferably the disease is ALT-positive cancer.

Yet preferably the cancer is selected from the group consisting of: soft tissue sarcoma, preferably chondrosarcoma, undifferentiated pleomorphic sarcomas including malignant fibrous histiocytoma, leiomyosarcoma, epithelioid sarcoma, liposarcoma, fibrosarcoma and variants, angiosarcoma and neurofibroma, central nervous system cancer, preferably grade 2 diffuse astrocytoma; grade 3 anaplastic astrocytoma; grade 4 paediatric glioblastoma multiforme, oligodendroglioma, anaplastic medulloblastoma, grade 1 pilocytic astrocytoma, nonanaplastic medulloblastoma, meningioma, schwannoma, urinary bladder cancer, in particular small cell carcinoma and invasive urothelial carcinoma, adrenal gland or peripheral nervous system cancer, in particular ganglioneurobalstoma, neuroblastoma and pheochromocytoma, neuroendocrine neoplasms such as paraganglioma and carcinoid tumour, kidney cancer, in particular chromophobe carcinoma, sarcomatoid carcinoma and clear cell and papillary carcinomas, lung and pleural cancer, in particular malignant mesothelioma, large cell carcinoma and small cell carcinoma, skin cancer such as malignant melanoma, liver cancer such as hepatocellular carcinoma, testis cancer such as non seminomatous germ cell tumor, breast cancer, in particular lobular carcinoma; ductal carcinoma and medullary carcinoma, uterus cancer such as serous endometrial carcinoma, squamous carcinoma of cervix, ovary cancer, in particular clear cell carcinoma, endometrioid carcinoma, Gall bladder cancer such as adenocarcinoma, oesophagus cancer.

In a further aspect the invention provides an oligonucleotide comprising one of the following sequence:
(TTAGGG) SEQ ID No. 1, (TAGGGT) SEQ ID No. 2, (AGGGTT) SEQ ID No. 3, (GGGTTA) SEQ ID No. 4, (GGTTAG) SEQ ID No. 5 or (GTTAGG) SEQ ID No. 6 or a complementary sequence thereof or a fragment or a variant or a mixture thereof for use in the treatment and/or prevention of a non-cancer condition associated with telomere dysfunction.

Preferably the non-cancer condition associated with telomere dysfunction is selected from the group consisting of: Hutchinson-Gilford progeria syndrome (HGPS), Werner's syndrome, Bloom's syndrome, ataxia telangiectasia, familial IPF, sporadic IPF, aplastic anaemia, autosomal-dominant dyskeratosis congenital, Familial MDS-AML, de novo dyskeratosis congenita, X-linked recessive dyskeratosis congenita, Hoyeraal-Hreiderasson syndrome, Revesz syndrome, Autosomal-recessive dyskeratosis congenita, Coats plus syndrome, condition caused by mutations or inactivation of any one of TRF1, POT1, TPP1, TINF2, RAP1 or TRF2, impaired regeneration upon partial hepatectomy, liver fibrosis, liver Chronic inflammation, liver cirrhosis, pulmonary fibrosis, altered myeloid progenitor differentiation, bone marrow failure, chronic obstructive pulmonary disease (COPD), neurological disorders including Alzheimer's Disease, osteoporosis, atherosclerosis, heart disease, Duchenne muscular dystrophy, Type 2 diabetes, impaired fertility, impaired wound healing, arthritis, cataracts, age-related macular degeneration, ageing.

Preferably the oligonucleotide is a locked nucleic acid (LNA)-modified oligonucleotide or a 2'-O-Methyl-modified oligonucleotide.

LNA is generally considered to be an RNA mimic in which the ribose sugar moiety is locked by an oxymethylene bridge connecting the C(2')- and C(4')-atoms which conformationally restricts LNA monomers into an N-type sugar puckering (Veedu R et al. 2010). LNA is a molecule which contains at least one nucleotide bearing the LNA modification. Preferably the LNA contains, at least 2, at least 3, at least 4, at least 5, at least 10, at least 15, at least 20 nucleotides bearing the LNA modification. 2'-O-Methylmodified oligonucleotide is a molecule which contains at least one nucleotide bearing the 2'-O-Methyl modification. Preferably the 2'-O-Methyl-modified oligonucleotide contains, at least 2, at least 3, at least 4, at least 5, at least 10, at least 15, at least 20 nucleotides bearing the 2'-O-Methyl modification.

In a further aspect the invention provides a pharmaceutical composition comprising at least one oligonucleotide as defined above and pharmaceutically acceptable carriers for use in the treatment and/or prevention of a disease characterized by alternative lengthening of telomeres or for use in the treatment and/or prevention of a non-cancer condition associated with telomere dysfunction.

Preferably the pharmaceutical composition further comprises at least another therapeutic agent, preferably the other therapeutic agent is selected from the group of: anti-tumoral agent, anti-pain agent, anti-emetic agent (such as aprepitant, fosaprepitant, Dolasetron, granisetron, ondansetron, palonosetron, tropisetron, or ramosetron, Dexamethasone).

Preferably the other therapeutic agent is selected from the group consisting of: ATR inhibitor, DDR inhibitor, HR inhibitor, molecule that specifically target telomeres, preferably G-quadruplexes interacting molecules, molecule that cause DNA damage generation specifically at telomeres.

In a further aspect the invention provides a method to identify a subject to be treated with the oligonucleotide as defined above or with the pharmaceutical composition as defined above comprising detecting the presence and/or measuring the amount of an RNA, said RNA being a RNA transcript synthesized using a specific dysfunctional telomeric DNA as a template for transcription or a fragment of said RNA transcript, said fragment (DDRNA) being generated by processing by Dicer and/or Drosha wherein said subject is affected by a disease characterized by alternative lengthening of telomeres or affected by a non-cancer condition associated with telomere dysfunction.

In the present invention DDRNAs are non-coding RNAs. They are RNA transcripts synthesized using a specific damaged and/or dysfunctional telomeric DNA as a template for transcription of a long RNA precursor which can be then processed by Dicer and/or Drosha into shorter non-coding RNAs (DDRNAs or tDDRNAs).

DDRNAs originate at the locus and carry the sequence of the damaged locus. When chemically synthesized or generated in vitro by DICER and/or DROSHA cleavage of transcripts spanning the locus, DDRNAs promote DDR activation at the DNA damage site in RNase A-treated cells even in the absence of other mammalian RNAs.

DDRNAs act differently from microRNAs and canonical RNAi mechanisms because as shown in (Francia et al., 2012):
  DDRNAs act without the need for any other cellular RNA (see the results obtained with gel-extracted RNA and synthetic RNAs in RNase A-treated cells experiments).
  DDRNAs can have a sequence (LAC or TET repeats) that has no endogenous cellular transcripts match and still be biological active.
  DDRNAs can act fast (in minutes) at room temperature in cells inhibited for transcription and translation (see the results obtained in RNAse A-treated cells experiments).
  Inactivation of GW proteins (effectors of canonical miRNAs) does not affect DDR foci.
DDRNAs are small RNAs, with the potential to form double-stranded pairs, they are generated by processing by DICER and/or DROSHA of a sequence-specific RNA transcript synthesized upon transcription of a damaged DNA locus. DDRNAs are small RNAs of a length between 10 and 50 nucleotides. For example of a length between 17 and 32 nucleotides. For example of a length between 20 and 25 nucleotides. For example of a length between 21 and 23 nucleotides.

Said DDRNAs function by favoring the sequence-specific accumulation of DDR factors at specific sites of DNA damage and promote DDR activation (i.e. comprising, but not limiting to, DNA damage signalling, such as through protein phosphorylation events, and DNA damage repair, such as homologous recombination).

DDRNA precursors are RNA molecules longer than DDRNAs (at least 25 bases long, preferably at least 30 bases long, preferably at least 50 bases long, preferably at least 100 bases long, preferably at least 150 bases long, preferably at least 200 bases long, preferably at least 250 bases long, preferably at least 300 bases long), transcribed upon DNA damage, using damaged DNA as a template. They are processed by DROSHA and/or DICER to generate DDRNAs. Telomeric DDRNA precursors are multiples of telomeric DDRNAs.

In the present invention a fragment of SEQ ID No. 1 to SEQ ID No. 6 is a functional fragment that has the same therapeutic activity as said sequences. The fragment corresponds to the oligonucleotides of the present invention that are truncated by one or more nucleotides on the Tend, the 3'end, or both the Tend and the 3'end, so long as at least two contiguous nucleotides of the untruncated oligonucleotide remain. Preferably the truncated oligonucleotides have 2, 3, 4 or 5 contiguous nucleotides found in the untruncated oligonucleotides.

Comprised in the present invention are also oligonucleotides comprising the above sequences (SEQ ID No. 1 to 6) that are repeated 1 or more times, for instance oligonucleotides comprising one of the following sequence: $(TTAGGG)_n$, $(TAGGGT)_n$, $(AGGGTT)_n$, $(GGGTTA)_n$, $(GGTTAG)_n$ or $(GTTAGG)_n$ wherein $1<n<1000$, preferably $1<n<500$, preferably $1<n<200$, preferably $1<n<100$, preferably $1<n<50$, preferably $1<n<20$, preferably $1<n<10$, preferably $1<n<5$.

The oligonucleotides may be also 6, 7, 8, 9, 10, 11, 12, 13, 14, 15, 16, 17, 18, 19, 20 21, 22, 23, 24, 25 ect . . . nucleotide long. They are not necessarily multiple of 6 nucleotides.

In the present invention the variant of SEQ ID No. 1 to 6 are oligonucleotides in which 1, 2, 3, 4 or 5 nucleotides are substituted with a different nucleotide. The variants have at least 50% identity with SEQ ID No. 1 to 6, preferably at least 60%, preferably at least 70%, preferably at least 80%, preferably at least 85%, preferably at least 90%, preferably at least 95% identity. The variant has the same therapeutic activity as the oligonucleotide. Preferred telomeric hexanucleotide variants include: TCAGGG, TTCGGG, GTAGGG, TGAGGG, TTGGGG, TAAGGG, ATAGGG, CTAGGG, TTTGGG, TTAAGGG and their complementary sequences (FIG. 5 of (Lee et al., 2014)).

The oligonucleotide of the present invention, fragment thereof or variant thereof is complementary to the sequence of DDRNAs and/or their precursors, thereby inhibiting DDRNAs and/or their precursors function.

Preferably the oligonucleotide is a LNA molecule or a 2'-O-Methyl modified oligonucleotide.

These oligonucleotides comprise but are not limiting to locked nucleic acids (LNA), phosphorothioate modified oligonucleotides, phosphorothioate modified locked nucleic acids, 2'-O-methoxyethyl modified oligonucleotides, 2' O-Methyl modified oligonucleotides, 2O-[2-(N-Methylcarbamoyl) ethyl] ribonucleosides, methylphosphonates, morpholino oligonucleotides, LNA-DNA-LNA gapmer oligonucleotides, mixmers, Chimeric 2'-O-methyl RNA-DNA gapmer, N3'-P5' Phosphoroamidate, 2'-fluoro-arabino nucleic acid, Phosphoroamidate Morpholino, Cyclohexene nucleic acid, Tricyclo-DNA, Peptide nucleic acid, Unlocked nucleic acid, Hexitol nucleic acid, Boranophosphate oligonucleotides, Phosphoroamidate oligonucleotides, preferably said modified oligonucleotide is phosphorothioated, and/or oligonucleotides expressed by plasmid-encoded genes delivered by different means (comprising but not limited to plasmid transfection, viral infection).

In the present invention a disease characterized by alternative lengthening of telomeres is a disease characterized by the presence of cells that maintain telomeres despite lacking telomerase activity and/or showing one or more features listed below.

In particular, alternative lengthening of telomeres may be identified/measured by at least one of the following feature:
  lack of telomerase activity (for instance measured by enzymatic assays)
  presence of longer and more heterogeneous telomeres, compared with telomerase-positive cells, as measured by telomere restriction fragment and southern blot analysis, or other means based on in situ hybridization.
  presence of ALT-associated PML bodies (APBs), which are foci of PML protein, co-localizing with telomere chromatin, as detected by immunofluorescence.
  presence of DDR markers such as (γH2AX, RPA, HR proteins) co-localizing at telomeres, as detected by immunofluorescence or other means.
  presence of mutations in ATRX and/or DAXX genes or altered expression or functions thereof (Heaphy et al., 2011).
  Presence of c-circles, which are single-strand c-rich extrachromosomal telomeric DNAs.
  Presence of t-circles, which are extrachromosomal double-stranded telomeric DNAs.
  Telomere sister chromatid exchange, a marker of recombination among telomeres.
  Increased tandem repeat instability at the MS32 minisatellite locus.

These features may be measured/identified by known methods in the art, for instance as reported in (Henson and Reddel, 2010) (included by reference herein).

In the present invention a non-cancer condition associated with telomere dysfunction is a disease or condition or syndrome characterized by telomeres engaging the components of the DDR machinery. In the present invention "telomere dysfunction" or "dysfunctional telomere" is a telomere with damaged telomeric DNA and/or a critically short telomeric DNA and/or uncapped telomeric DNA and/or deprotected telomeric DNA and/or accelerated telomere loss and/or any instance where DDR signal is active at a telomere.

Telomere dysfunction has a causal role in a number of degenerative disorders. Their manifestation encompass common disease states such as Hutchinson-Gilford progeria syndrome (HGPS), Werner's syndrome, Bloom's syndrome, ataxia telangiectasia, familial IPF, sporadic IPF, aplastic anaemia, autosomal-dominant dyskeratosis congenital, Familial MDS-AML, de novo dyskeratosis congenita, X-linked recessive dyskeratosis congenita, Hoyeraal-Hreiderasson syndrome, Revesz syndrome, Autosomal-recessive dyskeratosis congenita, Coats plus syndrome, condition caused by mutations or inactivation of any one of TRF1, POT1, TPP1, TINF2, RAP1 or TRF2, impaired regeneration upon partial hepatectomy, liver fibrosis, liver Chronic inflammation, liver cirrhosis, pulmonary fibrosis, altered myeloid progenitor differentiation, bone marrow failure, chronic obstructive pulmonary disease (COPD), neurological disorders including Alzheimer's Disease, osteoporosis, atherosclerosis, heart disease, Duchenne muscular dystrophy, Type 2 diabetes, impaired fertility, impaired wound healing, arthritis, cataracts, age-related macular degeneration, ageing. In example, accelerated telomere loss, i.e a telomere dysfunction, has been proposed to be a factor leading to end-stage organ failure in chronic diseases of high cellular turnover such as liver cirrhosis (Rudolph et al. 2000).

Although these disorders seem to be clinically diverse, collectively they comprise a spectrum of syndromes characterized by short or damaged and more broadly dysfunctional telomeres, and telomere dysfunction is also a key feature of ageing and age-related diseases (see (Armanios and Blackburn, 2012; Gray et al., 2015; Opresko and Shay, 2016; Wang et al., 2015; Xi et al., 2013; Satyanarayana et al, 2003; Rudolph et al. 2000)).

Further telomere dysfunction may be caused by mutations or inactivation, in particular of TRF1 (official name TERF1, gene ID 7013), POT1 (gene ID 25913), TPP1 (official name ACD, gene ID 65057), TINF2 (gene ID 26277), RAP1 (official name TERF2IP, gene ID 54386) or TRF2 (official name TERF2, gene ID 7014).

In addition, TRF2KO models cause telomere dysfunction and recapitulate the non-cancer conditions associated with telomere dysfunction.

Telomere dysfunction may be identified/measured by at least one of the following feature or method: indirect immunofluorescence, immunohistochemistry, chromatin immunoprecipitation, tDDRNA detection.

More specifically, the invention pertains to the use of polynucleotides, oligonucleotides, deoxynucleotides, dinucleotides, or dinucleotide dimers, or similar compounds, for the inhibition of cell proliferation or inhibition of DNA repair. As used herein, inhibition of cell proliferation includes complete abrogation of cell division, partial inhibition of cell division and transient inhibition of cell division, cell death, apoptosis, necrosis, cellular senescence, cell differentiation, mitotic catastrophe as measured by standard tests in the art and as described in the Examples. The invention also pertains to the prevention and/or treatment of diseases characterized by ALT, including, but not limited to, cancer and pre-cancerous conditions, wherein the disease affects cells of any organ and any embryonic origin. Metastatic ALT tumors and cancers that have regrown or relapsed after treatment, as well as primary tumors, can be treated by the methods of the invention.

In one embodiment, the compositions of the present invention comprise oligonucleotides approximately 2-200 bases in length, which can be administered to a mammal (e.g., human) in an appropriate vehicle. In another embodiment, the oligonucleotides are about 5 to about 100 nucleotides in length. In still another embodiment, the oligonucleotides are about 5 to about 50 nucleotides in length. In yet another embodiment, the DNA oligonucleotides are about 8-30 nucleotides in length. Preferably they are 8-21 nucleotide in length, still preferably 8-16 nucleotide in length.

Any suitable method of administering the oligonucleotide of the present invention to the organism, such that the oligonucleotide contacts and/or enters the cells or tissues of interest, is reasonably expected to be effective. The effects can be optimized using routine optimization protocols.

The oligonucleotide, deoxynucleotides of the present invention can be obtained from any appropriate source, or can be synthetically produced.

DNA fragments, oligonucleotides, deoxynucleotides, dinucleotides or dinucleotide dimers, may be applied to the skin and can be administered alone, or in combination with physiologically acceptable carriers, including solvents, perfumes or colorants, stabilizers, sunscreens or other ingredients, for medical or cosmetic use. They can be administered in a vehicle, such as water, saline, or in another appropriate delivery vehicle. The delivery vehicle can be any appropriate vehicle, which delivers the oligonucleotides, deoxynucleotides, dinucleotides, or dinucleotide dimers. In one embodiment, the concentration range of oligonucleotide can be from 0.1 nM to 500 µM, preferably the in vitro range is between 0.2 nM and 300 µM, preferably the in vitro range is between 0.5 nM to 200 µM. Preferred in vivo range is 0.1-500 mg/kg, preferably in vivo range is 1-50 mg/kg.

To allow access of the active ingredients of the composition to deeper-lying skin cells, vehicles which improve penetration through outer layers of the skin, e.g., the stratum corneum, are useful. Vehicle constituents for this purpose include, but are not limited to, ethanol, isopropanol, diethylene glycol ethers such as diethylene glycol monoethyl ether, azone (1-dodecylazacycloheptan-2-one), oleic acid, linoleic acid, propylene glycol, hypertonic concentrations of glycerol, lactic acid, glycolic acid, citric acid, and malic acid. In one embodiment, propylene glycol is used as a delivery vehicle. In a preferred embodiment, a mixture of propylene glycol: ethanol: isopropyl myristate (1:2.7:1) containing 3% benzylsulfonic acid and 5% oleyl alcohol is used.

In another embodiment, a liposome preparation can be used. The liposome preparation can comprise liposomes which penetrate the cells of interest or the stratum corneum, and fuse with the cell membrane, resulting in delivery of the contents of the liposome into the cell. For example, liposomes such as those described in U.S. Pat. No. 5,077,211 of Yarosh, U.S. Pat. No. 4,621,023 of Redziniak et al. or U.S. Pat. No. 4,508,703 of Redziniak et al. can be used. The compositions of the invention intended to target skin conditions can be administered before, during, or after exposure of the skin of the mammal to UV or agents causing oxidative damage. Other suitable formulations can employ niosomes. Niosomes are lipid vesicles similar to liposomes, with membranes consisting largely of non-ionic lipids, some forms of which are effective for transporting compounds across the stratum corneum.

Other suitable delivery methods intended primarily for skin include use of a hydrogel formulation, comprising an aqueous or aqueous-alcoholic medium and a gelling agent in addition to the oligonucleotide (s). Suitable gelling agents include methylcellulose, carboxymethylcellulose, hydroxypropylmethylcellulose, carbomer (carbopol), hypan, polyacrylate, and glycerol polyacrylate.

In one embodiment, the oligonucleotides, deoxynucleotides, dinucleotides, dinucleotide dimers, or composition comprising one or more of the foregoing, is applied topically to the skin surface. In other embodiments, the oligonucleotides, deoxynucleotides, dinucleotides, dinucleotide dimers, or composition comprising one or more of the foregoing, is delivered to other cells or tissues of the body such as epithelial cells. Cells of tissue that is recognized to have a lesser barrier to entry of such substances than does the skin can be treated, e.g., orally to the oral cavity; by aerosol to the respiratory epithelium; by instillation to the bladder epithelium; by instillation or suppository to intestinal (epithelium) or by other topical or surface application means to other cells or tissues in the body, including eye drops, nose drops and application using angioplasty, for example. Furthermore, the oligonucleotides of the present invention can be administered intravenously or injected directly into the tissue of interest intracutaneously, subcutaneously, intramuscularly or intraperitoneally. In addition, for the treatment of blood cells, the compounds of the present invention can be administered intravenously or during extracorporeal circulation of the cells, such as through a photophoresis device, for example. As demonstrated herein, all that is needed is contacting the cells of interest with the oligonucleotide compositions of the present invention.

The oligonucleotides, deoxynucleotides, dinucleotides, dinucleotide dimers, agent that promotes differentiation, or composition comprising one or more of the foregoing, is administered to (introduced into or contacted with) the cells of interest in an appropriate manner.

The "cells of interest" as used herein are those cells which may become affected or are affected by a disease characterized by ALT or by dysfunctional telomeres.

The oligonucleotides, deoxynucleotides, dinucleotides, dinucleotide dimers, agent that promotes differentiation, or composition comprising one or more of the foregoing, is applied at an appropriate time, in an effective amount. The "appropriate time" will vary, depending on the type and molecular weight of the oligonucleotides, deoxynucleotides, dinucleotides, dinucleotide dimers, or other agent employed, the condition to be treated or prevented, the results sought, and the individual patient.

An "effective amount" as used herein, is a quantity or concentration sufficient to achieve a measurable desired result. The effective amount will depend on the type and molecular weight of the oligonucleotides, deoxynucleotides, dinucleotides, dinucleotide dimers, or agent employed, the condition to be treated or prevented, the results sought, and the individual patient. For example, for the treatment or prevention of ALT hyperproliferative disease, cancerous, or pre-cancerous conditions, the effective amount is the amount necessary to reduce or relieve any one of the symptoms of the disease, to reduce the volume, area or number of cells affected by the disease, to prevent the formation of affected areas, or to reduce the rate of growth of the cells affected by the hyperproliferative disorder.

As demonstrated herein, the inhibitors of the present invention are active in vitro and in vivo in their unmodified form, e.g., sequences of unmodified oligonucleotides linked by phosphodiester bonds. As used herein, the terms "oligonucleotide", "dinucleotide," etc., refer to molecules having ribose and/or deoxyribose as the sugar, and having phosphodiester linkages ("phosphate backbone") as occur naturally, unless a different linkage or backbone is specified.

Oligonucleotides are relatively short polynucleotides. Polynucleotides are linear polymers of nucleotide monomers in which the nucleotides are linked by phosphodiester bonds between the 3' position of one nucleotide and the 5' position of the adjacent nucleotide. Unless otherwise indicated, the "oligonucleotides" of the invention as described herein have a phosphodiester backbone.

To enhance delivery through the skin, the oligonucleotides of the invention may be modified so as to either mask or reduce their negative charges or otherwise alter their chemical characteristics. This may be accomplished, for example, by preparing ammonium salts of the oligonucleotides using readily available reagents and methods well known in the art. Preferred ammonium salts of the oligonucleotides include trimethyl-, triethyl-, tributyl-, tetramethyl-, tetraethyl-, and tetrabutyl-ammonium salts. Ammonium and other positively charged groups can be convalently bonded to the oligonucleotide to facilitate its transport across the stratum corneum, using an enzymatically degradable linkage that releases the oligonucleotide upon arrival inside the cells of the viable layers of the epidermis.

Another method for reducing or masking the negative charge of the oligonucleotides includes adding a polyoxyethylene spacer to the 5'phosphate groups of the oligonucleotides and/or the internal phosphates of the oligonucleotides using methods and reagents well known in the art. This, in effect, adds a 6-or 12-carbon modifier (linker) to the phosphate that reduces the net negative charge by +1 and makes the oligonucleotides less hydrophilic.

Further negative charge reduction is achieved by adding a phosphoroamidite to the end of the polyoxyethylene linker, thereby providing an additional neutralizing positive charge. The phosphodiester backbone of the oligonucleotides of the present invention can also be modified or synthesized to reduce the negative charge. A preferred method involves the use of methyl phosphonic acids (or chiral-methylphosphonates), whereby one of the negatively charged oxygen atoms in the phosphate is replaced with a methyl group. These oligonucleotides are similar to oligonucleotides having phosphorothioate linkages which comprise a sulfate instead of a methyl group and which are also within the scope of the present invention.

The oligonucleotides of the present invention can also take the form of peptide nucleic acids (PNAs) in which the bases of the nucleotides are connected to each other via a peptide backbone.

Other modifications of the oligonucleotides such as those described, for example, in U.S. Pat. Nos. 6,537,973 and 6,506,735 as well as in (Stenvang et al., 2012) (all of which are incorporated herein by reference for all of the oligonucleotide modifications described therein) and others will be readily apparent to those skilled in the art.

The oligonucleotides can also be "chimeric" oligonucleotides which are synthesized to have a combination of two or more chemically distinct backbone linkages, one being phosphodiester. In one embodiment chimeric oligonucleotides are with one or more phosphodiester linkages at the 3' end. In one embodiment chimeric oligonucleotides are with one or more phosphodiester linkages at the 5' end. In another embodiment chimeric oligonucleotides are with one or more phosphodiester linkages at the 3' and 5' ends.

The oligonucleotide or oligonucleotides to be used to treat and/or prevent a disease characterized by alternative lengthening of telomeres, such as cancer or an Epstein-Bar virus infection, in particular soft tissue sarcoma, preferably chondrosarcoma, undifferentiated pleomorphic sarcomas including malignant fibrous histiocytoma, leiomyosarcoma, epithelioid sarcoma, liposarcoma, fibrosarcoma and variants, angiosarcoma and neurofibroma, central nervous system cancer, preferably grade 2 diffuse astrocytoma; grade 3 anaplastic astrocytoma; grade 4 paediatric glioblastoma multiforme, oligodendroglioma, anaplastic medulloblastoma, grade 1 pilocytic astrocytoma, nonanaplastic medulloblastoma, meningioma, schwannoma, urinary bladder cancer, in particular small cell carcinoma and invasive urothelial carcinoma, adrenal gland or peripheral nervous system cancer, in particular ganglioneurobalstoma, neuroblastoma and pheochromocytoma, neuroendocrine neoplasms such as paraganglioma and carcinoid tumour, kidney cancer, in particular chromophobe carcinoma, sarcomatoid carcinoma and clear cell and papillary carcinomas, lung and pleural cancer, in particular malignant mesothelioma, large cell carcinoma and small cell carcinoma, skin cancer such as malignant melanoma, liver cancer such as hepatocellular carcinoma, testis cancer such as non seminomatous germ cell tumor, breast cancer, in particular lobular carcinoma; ductal carcinoma and medullary carcinoma, uterus cancer such as serous endometrial carcinoma, squamous carcinoma of cervix, ovary cancer, in particular clear cell carcinoma, endometrioid carcinoma, gall bladder cancer such as adenocarcinoma, oesophagus cancer or to treat and/or prevent for use in the treatment and/or prevention of a non-cancer condition associated with telomere dysfunction, in particular Hutchinson-Gilford progeria syndrome (HGPS), Werner's syndrome, Bloom's syndrome, ataxia telangiectasia, familial IPF, sporadic IPF, aplastic anaemia, autosomal-dominant dyskeratosis congenital, Familial MD S-AML, de novo dyskeratosis congenita, X-linked recessive dyskeratosis congenita, Hoyeraal-Hreiderasson syndrome, Revesz syndrome, Autosomal-recessive dyskeratosis congenita, Coats plus syndrome, condition caused by mutations or inactivation of any one of TRF1, POT1, TPP1, TINF2, RAP1 or TRF2impaired regeneration upon partial hepatectomy, liver fibrosis, liver Chronic inflammation, liver cirrhosis, pulmonary fibrosis, altered myeloid progenitor differentiation, bone marrow failure, chronic obstructive pulmonary disease (COPD), neurological disorders including Alzheimer's Disease, osteoporosis, atherosclerosis, heart disease, Duchenne muscular dystrophy, Type 2 diabetes, impaired fertility, impaired wound healing, arthritis, cataracts, age-related macular degeneration, ageing.

For instance such diseases are described in (Durant, 2012) (enclosed by reference herein).

The oligonucleotides can be used in a composition in combination with a pharmaceutically or physiologically acceptable carrier. Such a composition may also contain in addition, diluents, fillers, salts, buffers, stabilizers, solubilizers, and other materials well known in the art. Cationic lipids such as DOTAP [N-(2, 3-dioleoyloxy) propyl]-N, N, N-trimethylammonium salts may be used with oligonucleotides to enhance stability. Oligonucleotides may be complexed with PLGA/PLA copolymers, chitosan or fumaric acid/sebacic acid copolymers for improved bioavailability {where PLGA is [poly (lactide-co-glycolide)]; PLA is poly (L-lactide)}. The terms "pharmaceutically acceptable" and "physiologically acceptable" mean a non-toxic material that does not interfere with the effectiveness of the biological activity of the active ingredient (s). The characteristics of the carrier will depend on the route of administration.

A composition to be used as an antiproliferative agent for ALT disease may further contain other agents which either enhance the activity of the oligonucleotide (s) or complement its activity or use in treatment, such as chemotherapeutic or radioactive agents. Such additional factors and/or agents may be included in the composition to produce a synergistic effect with the oligonucleotide (s), or to minimize side effects. Additionally, administration of the composition of the present invention may be administered concurrently with other therapies, e.g., administered in conjunction with a chemotherapy or radiation therapy regimen. The oligonucleotides as described herein can be used in combination with other compositions and procedures for the treatment of diseases. For example, a tumor may be treated conventionally with surgery, radiation, chemotherapy, or immunotherapy, combined with oligonucleotide therapy, and then oligonucleotides may be subsequently administered to the patient to extend the dormancy of micrometastases and to stabilize and inhibit the growth of any residual primary tumor. The oligonucleotides can be used in combination with telomerase inhibitors, to prevent the expansion of telomerase-negative, ALT-positive clones. Preferably the other therapeutic agent is selected from the group consisting of: ATR inhibitor, DDR inhibitor, HR inhibitor, molecule that specifically targets and/or causes DNA damage generation specifically at telomeres, preferably G-quadruplexes interacting molecules.

In the present invention an ATR inhibitor is a small molecule compound able to inhibit the kinase activity of ATR, comprising but not limited to VE-821 (Vertex Pharmaceuticals), VE-822 (Vertex Pharmaceuticals), AZ20 (AstraZeneca), AZD6738 (AstraZeneca) (as described in (Flynn et al., 2015; Weber and Ryan, 2015) (all references are incorporated by reference).

A DDR inhibitor is any compound or experimental approach able to impair or inhibit the cellular process known as DNA damage response (DDR), comprising but not limited to: Caffeine, Wortmannin, KU-55933, KU-60019, KU-559403, Schisandrin B, NU6027, NVP-BEZ235, (as described in (Begg et al., 2011; Kelley et al., 2014; Weber and Ryan, 2015), all references are incorporated by reference).

A HR inhibitor is any compound or experimental approach able to impair or inhibit the cellular process known as DNA repair by homologous recombination (HR), comprising but not limited to: Iniparib (SAR240550, BSI-201; Sanofi-Aventis), Olaparib (AZD2281, KU-0069436; AstraZeneca), Niraparib (Tesaro), Rucaparib (CO-338, AG-014699, PF-01367338; Pfizer), Veliparib (ABT-888; Abbott), AZD2461 (AstraZeneca), BMN673 (BioMarin Pharmaceutical), CEP-9722 (Cephalon), E7016 (Esai), INO-1001 (Inotek Pharmaceuticals), MK-4827 (Merck), Methoxyamine (Sigma Aldrich), RI-1, IBR2, B02, Halenaquinone (described in (Feng et al., 2015; Kelley et al., 2014; Ward et al., 2015), all references are incorporated by reference).

A molecule that specifically targets and/or causes DNA damage generation at telomeres is any compound or experimental approach which specifically or preferentially interacts with telomeres, inducing DNA damage within telomeric DNA and/or activation or inhibition of DDR signalling and/or DNA repair, comprising but not limited to: G-quadruplex-binding ligands (e.g. BRAC 0-19, Telomestatin, RHPS4, Quarfloxin, TMPyP4, AS1410), topoisomerase inhibitors, cisplatin, hydroxyurea, (as described in (Lu et al., 2013; Muller and Rodriguez, 2014; Neidle, 2010; Salvati et al., 2015; Sissi and Palumbo, 2014), all references are incorporated by reference).

Other molecules that can be used in combination with the oligonucleotides are: Abitrexate (Methotrexate Injection), Abraxane (Paclitaxel Injection), Adcetris (Brentuximab Vedotin Injection), Adriamycin (Doxorubicin), Adrucil Injection (5-FU (fluorouracil)), Afinitor (Everolimus), Afinitor Disperz (Everolimus), Alimta (PEMETREXED), Alkeran Injection (Melphalan Injection), Alkeran Tablets (Melphalan), Aredia (Pamidronate), Arimidex (Anastrozole), Aromasin (Exemestane), Arranon (Nelarabine), Arzerra (Ofatumumab Injection), Avastin (Bevacizumab), Bexxar (Tositumomab), BiCNU (Carmustine), Blenoxane (Bleomycin), Bosulif (Bosutinib), Busulfex Injection (Busulfan Injection), Campath (Alemtuzumab), Camptosar (Irinotecan), Caprelsa (Vandetanib), Casodex (Bicalutamide), CeeNU (Lomustine), CeeNU Dose Pack (Lomustine), Cerubidine (Daunorubicin), Clolar (Clofarabine Injection), Cometriq (Cabozantinib), Cosmegen (Dactinomycin), CytosarU (Cytarabine), Cytoxan (Cytoxan), Cytoxan Injection (Cyclophosphamide Injection), Dacogen (Decitabine), DaunoXome (Daunorubicin Lipid Complex Injection), Decadron (Dexamethasone), DepoCyt (Cytarabine Lipid Complex Injection), Dexamethasone Intensol (Dexamethasone), Dexpak Taperpak (Dexamethasone), Docefrez (Docetaxel), Doxil (Doxorubicin Lipid Complex Injection), Droxia (Hydroxyurea), DTIC (Decarbazine), Eligard (Leuprolide), Ellence (Ellence (epirubicin)), Eloxatin (Eloxatin (oxaliplatin)), Elspar (Asparaginase), Emcyt (Estramustine), Erbitux (Cetuximab), Erivedge (Vismodegib), Erwinaze (Asparaginase *Erwinia chrysanthemi*), Ethyol (Amifostine), Etopophos (Etoposide Injection), Eulexin (Flutamide), Fareston (Toremifene), Faslodex (Fulvestrant), Femara (Letrozole), Firmagon (Degarelix Injection), Fludara (Fludarabine), Folex (Methotrexate Injection), Folotyn (Pralatrexate Injection), FUDR (FUDR (floxuridine)), Gemzar (Gemcitabine), Gilotrif (Afatinib), Gleevec (Imatinib Mesylate), Gliadel Wafer (Carmustine wafer), Halaven (Eribulin Injection), Herceptin (Trastuzumab), Hexalen (Altretamine), Hycamtin (Topotecan), Hycamtin (Topotecan), Hydrea (Hydroxyurea), Iclusig (Ponatinib), Idamycin PFS (Idarubicin), Ifex (Ifosfamide), Inlyta (Axitinib), Intron A alfab (Interferon alfa-2a), Iressa (Gefitinib), Istodax (Romidepsin Injection), Ixempra (Ixabepilone Injection), Jakafi (Ruxolitinib), Jevtana (Cabazitaxel Injection), Kadcyla (Ado-trastuzumab Emtansine), Kyprolis (Carfilzomib), Leukeran (Chlorambucil), Leukine (Sargramostim), Leustatin (Cladribine), Lupron (Leuprolide), Lupron Depot (Leuprolide), Lupron DepotPED (Leuprolide), Lysodren (Mitotane), Marqibo Kit (Vincristine Lipid Complex Injection), Matulane (Procarbazine), Megace (Megestrol), Mekinist (Trametinib), Mesnex (Mesna), Mesnex (Mesna Injection), Metastron (Strontium-89 Chloride), Mexate (Methotrexate Injection), Mustargen (Mechlorethamine), Mutamycin (Mitomycin), Myleran (Busulfan), Mylotarg (Gemtuzumab Ozogamicin), Navelbine (Vinorelbine), Neosar Injection (Cyclophosphamide Injection), Neulasta (filgrastim), Neulasta (pegfilgrastim), Neupogen (filgrastim), Nexavar (Sorafenib), Nilandron (Nilandron (nilutamide)), Nipent (Pentostatin), Nolvadex (Tamoxifen), Novantrone (Mitoxantrone), Oncaspar (Pegaspargase), Oncovin (Vincristine), Ontak (Denileukin Diftitox), Onxol (Paclitaxel Injection), Panretin (Alitretinoin), Paraplatin (Carboplatin), Perjeta (Pertuzumab Injection), Platinol (Cisplatin), Platinol (Cisplatin Injection), PlatinolAQ (Cisplatin), PlatinolAQ (Cisplatin Injection), Pomalyst (Pomalidomide), Prednisone Intensol (Prednisone), Proleukin (Aldesleukin), Purinethol (Mercaptopurine), Reclast (Zoledronic acid), Revlimid (Lenalidomide), Rheumatrex (Methotrexate), Rituxan (Rituximab), RoferonA alfaa (Interferon alfa-2 a), Rubex (Doxorubicin), Sandostatin (Octreotide), Sandostatin LAR Depot (Octreotide), Soltamox (Tamoxifen), Sprycel (Dasatinib), Sterapred (Prednisone), Sterapred DS (Prednisone), Stivarga (Regorafenib), Supprelin LA (Histrelin Implant), Sutent (Sunitinib), Sylatron (Peginterferon Alfa-2b Injection (Sylatron)), Synribo (Omacetaxine Injection), Tabloid (Thioguanine), Taflinar (Dabrafenib), Tarceva (Erlotinib), Targretin Capsules (Bexarotene), Tasigna (Decarbazine), Taxol (Paclitaxel Injection), Taxotere (Docetaxel), Temodar (Temozolomide), Temodar (Temozolomide Injection), Tepadina (Thiotepa), Thalomid (Thalidomide), TheraCys BCG (BCG), Thioplex (Thiotepa), TICE BCG (BCG), Toposar (Etoposide Injection), Torisel (Temsirolimus), Treanda (Bendamustine hydrochloride), Trelstar (Triptorelin Injection), Trexall (Methotrexate), Trisenox (Arsenic trioxide), Tykerb (lapatinib), Valstar (Valrubicin Intravesical), Vantas (Histrelin Implant), Vectibix (Panitumumab), Velban (Vinblastine), Velcade (Bortezomib), Vepesid (Etoposide), Vepesid (Etoposide Injection), Vesanoid (Tretinoin), Vidaza (Azacitidine), Vincasar PFS (Vincristine), Vincrex (Vincristine), Votrient (Pazopanib), Vumon (Teniposide), Wellcovorin IV (Leucovorin Injection), Xalkori (Crizotinib), Xeloda (Capecitabine), Xtandi (Enzalutamide), Yervoy (Ipilimumab Injection), Zaltrap (Ziv-aflibercept Injection), Zanosar (Streptozocin), Zelboraf (Vemurafenib), Zevalin (Ibritumomab Tiuxetan), Zoladex (Goserelin), Zolinza (Vorinostat), Zometa (Zoledronic acid), Zortress (Everolimus), Zytiga (Abiraterone), Nimotuzumab and immune checkpoint inhibitors such as nivolumab, pembrolizumab/MK-3475, pidilizumab and AMP-224 targeting PD-1; and BMS-935559, MEDI4736, MPDL3280A and MSB0010718C targeting PD-L1 and those targeting CTLA-4 such as ipilimumab. Radiotherapy means the use of radiation, usually X-rays, to treat illness. X-rays were discovered in 1895 and since then radiation has been used in medicine for diagnosis and investigation (X-rays) and treatment (radiotherapy). Radiotherapy may be from outside the body as external radiotherapy, using X-rays, cobalt irradiation, electrons, and more rarely other particles such as protons. It may also be from within the body as internal radiotherapy, which uses radioactive metals or liquids (isotopes) to treat cancer. Still further aspects include combining the oligonucleotides described herein with other anticancer therapies for synergistic or additive benefit.

Existing anticancer therapies are effective anticancer treatments that act by damaging the DNA or inhibiting DDR of cancer cells. However the DNA damaging activity of most of them is not sequence specific. The oligonucleotides of the present invention impair DDR in a sequence-specific manner, then they may confer sequence specificity to existing DNA damaging treatments thus enhancing efficacy.

The schedule of treatment with the combinations can foresee that the oligonucleotide is administered concomitantly, before and/or after any of the "partner" therapeutic agent identified above.

Combination therapies can be utilized for advanced stage of disease but also, prospectively, in the adjuvant and neo-adjuvant setting.

In the present invention "dysfunctional telomeric DNA" is a damaged telomeric DNA and/or a critically short telomeric DNA and/or uncapped telomeric DNA and/or deprotected telomeric DNA and/or any instance where DDR signal is active at a telomere.

The compositions of the present invention can be in the form of a liposome in which oligonucleotide (s) of the present invention are combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Pharmaceutical compositions can be made containing oligonucleotides to be used in antiproliferative therapy. Administration of such pharmaceutical compositions can be carried out in a variety of conventional ways known to those of ordinary skill in the art, such as oral ingestion, inhalation, for example, of an aerosol, topical or transdermal application, or intracranial, intracerebroventricular, intracerebral, intravaginal, intrauterine, oral, rectal or parenteral (e.g., intravenous, intraspinal, subcutaneous or intramuscular) route, or cutaneous, subcutaneous, intraperitoneal, parenteral or intravenous injection. The route of administration can be determined according to the site of the tumor, growth or lesion to be targeted. To deliver a composition comprising an effective amount of one or more oligonucleotides to the site of a growth or tumor, direct injection into the site can be used. Alternatively, for accessible mucosal sites, ballistic delivery, by coating the oligonucleotides onto beads of micrometer diameter, or by intraoral jet injection device, can be used. Viral vectors for the delivery of DNA in gene therapy have been the subject of investigation for a number of years. Retrovirus, adenovirus, adeno-associated virus, vaccinia virus and plant-specific viruses can be used as systems to package and deliver oligonucleotides for the treatment of cancer or other growths. Adeno-associated virus vectors have been developed that cannot replicate, but retain the ability to infect cells. An advantage is low immunogenicity, allowing repeated administration. Delivery systems have been reviewed, for example, in (Page and Cudmore, 2001). Studies carried out using oligonucleotides on the theory of their inhibiting the function of a target nucleic acid (antisense oligonucleotides), most of these studies carried out with phosphorothioate oligonucleotides, have found effective methods of delivery to target cells. Antisense oligonucleotides in clinical trials have been administered in saline solutions without special delivery vehicles (reviewed in (Hogrefe, 1999)). Formulations suitable for parenteral administration include aqueous and non-aqueous sterile injection solutions which may contain anti-oxidants, buffers, bacteriostats and solutes which render the formulation isotonic with the fluids of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described. A preferred pharmaceutical composition for intravenous, cutaneous, or subcutaneous injection should contain, in addition to oligonucleotide (s) of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

Use of timed release or sustained release delivery systems are also included in the invention. Such systems are highly desirable in situations where surgery is difficult or impossible, e.g., patients debilitated by age or the disease course itself, or where the risk-benefit analysis dictates control over cure. One method is to use an implantable pump to deliver measured doses of the formulation over a period of time, for example, at the site of a tumor. A sustained-release matrix can be used as a method of delivery of a pharmaceutical composition comprising oligonucleotides, especially for local treatment of a growth or tumor. It is a matrix made of materials, usually polymers, which are degradable by enzymatic or acid/base hydrolysis or by dissolution. Once inserted into the body, the matrix is acted upon by enzymes and body fluids. The sustained-release matrix desirably is chosen from biocompatible materials such as liposomes, polylactides (polylactic acid), polyglycolide (polymer of glycolic acid), polylactide co-glycolide (co-polymers of lactic acid and glycolic acid) polyanhydrides, poly (ortho) esters, polyproteins, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (copolymers of lactic acid and glycolic acid). The amount of oligonucleotide of the present invention in the pharmaceutical composition of the present invention will depend upon the nature and severity of the condition being treated, and on the nature of prior treatments which the patient has undergone. For a human patient, the attending physician will decide the dose of oligonucleotide of the present invention with which to treat each individual patient. Initially, the attending physician can administer low doses and observe the patient's response. Larger doses may be administered until the optimal therapeutic effect is obtained for the patient, and at that point the dosage is not increased further. The duration of therapy using the pharmaceutical composition of the present invention will vary, depending on the severity of the disease being treated and the condition and potential idiosyncratic response of each individual patient.

The present invention also provides a kit comprising at least one oligonucleotide as defined above or pharmaceutical composition comprising the same. The kit may contain written instructions. The oligonucleotide may be in a separate container.

In the present invention the method to identify a subject to be treated with the oligonucleotide as defined above or with the pharmaceutical composition as defined above may further comprise comparing the measured amount of DDR-NAs or tDDRNAs to a control amount. The control amount may be the amount measured in a healthy subject, the control amount may be the amount measured in a subject not affected by an ALT-disease or not affected by a non-cancer condition associated with telomere dysfunction, the control amount may be the amount measured in the same subject before or after therapeutic intervention.

The invention will be illustrated by means of non-limiting examples in reference to the following figures.

FIG. 1. Schematic of the DDRNA molecules generated at the telomeres and of LNA oligonucleotides. TeloG and TeloC DDRNAs are generated from dysfunctional telomeres, and are necessary for DDR activation. Antisense oligonucleotides (anti TeloG and anti TeloC) can bind and inhibit DDRNA function, thereby having a therapeutic activity. Sequences shown are non-limiting examples of the present invention. The reported sequences are one example of the possible ASO sequences.

Figure 2:
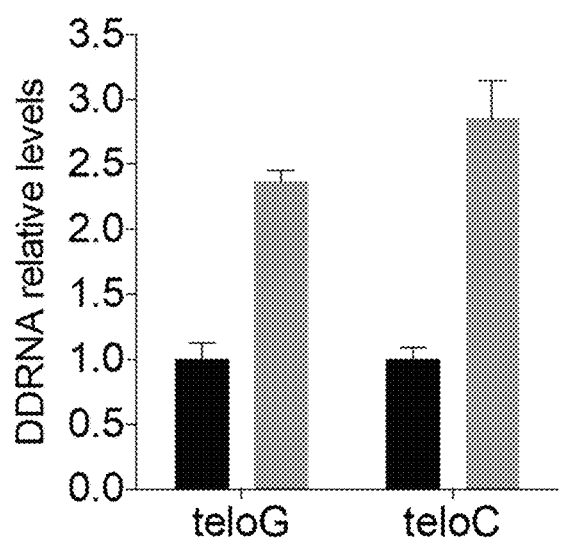

FIG. 2. Telomeric DDRNAs are upregulated upon telomere uncapping. Size selected (shorter than 40 nucleotides) RNA species were analyzed by RT-qPCR. MicroRNA mir29b was used as normalizer (n=4 independent experiments). TRF2+/− and TRF2−/− refer to cells that have a heterozygous or homozygous deletion of TRF2; TeloG and TeloC are DDRNAs with either telomeric strand sequence, as described in FIG. 1.

Figure 3:
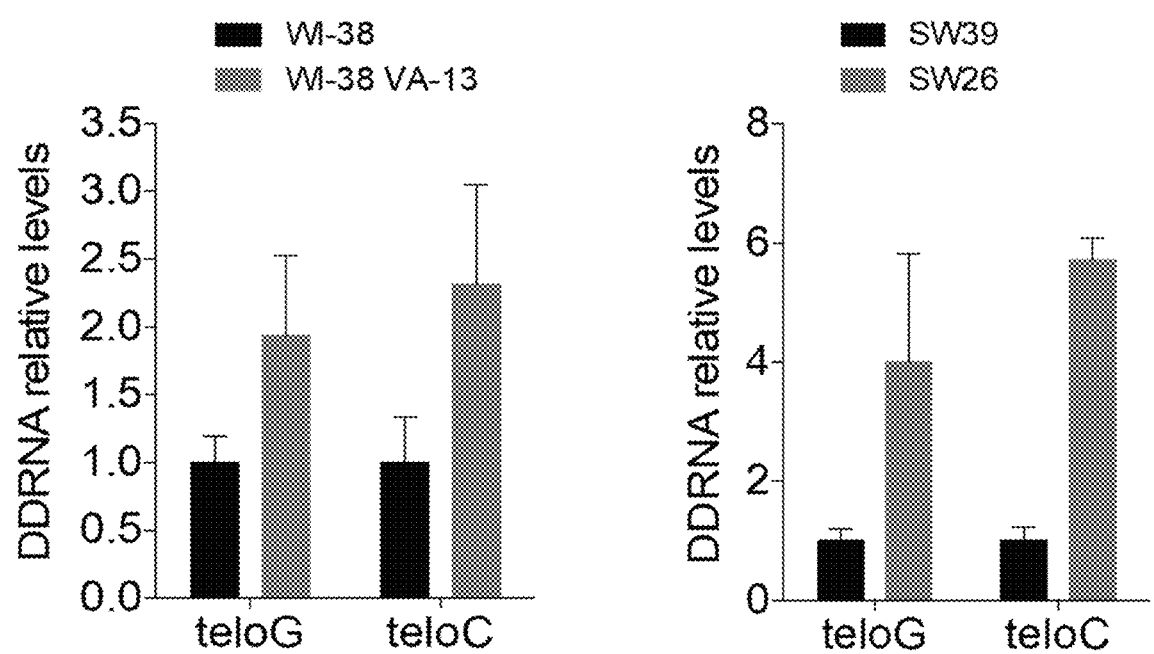

FIG. 3. Telomeric DDRNAs are upregulated in ALT cell lines. Size selected (shorter than 40 nucleotides) RNA was analyzed by RT-qPCR to detect DDRNA levels. The WI-38 VA-13 ALT cell line was compared to its parental non-ALT (or ALT negative) cell line, WI-38 (n=3 independent experiments; the telomerase-positive (non-ALT or ALT negative) cell line SW39 was compared to the ALT-positive cell line SW26 (n=2 independent experiments). An artificial spike-in RNA oligonucleotide was used as a normalizer. TeloG and TeloC are DDRNA with either telomeric strands sequence, as described in FIG. 1.

Figure 4:
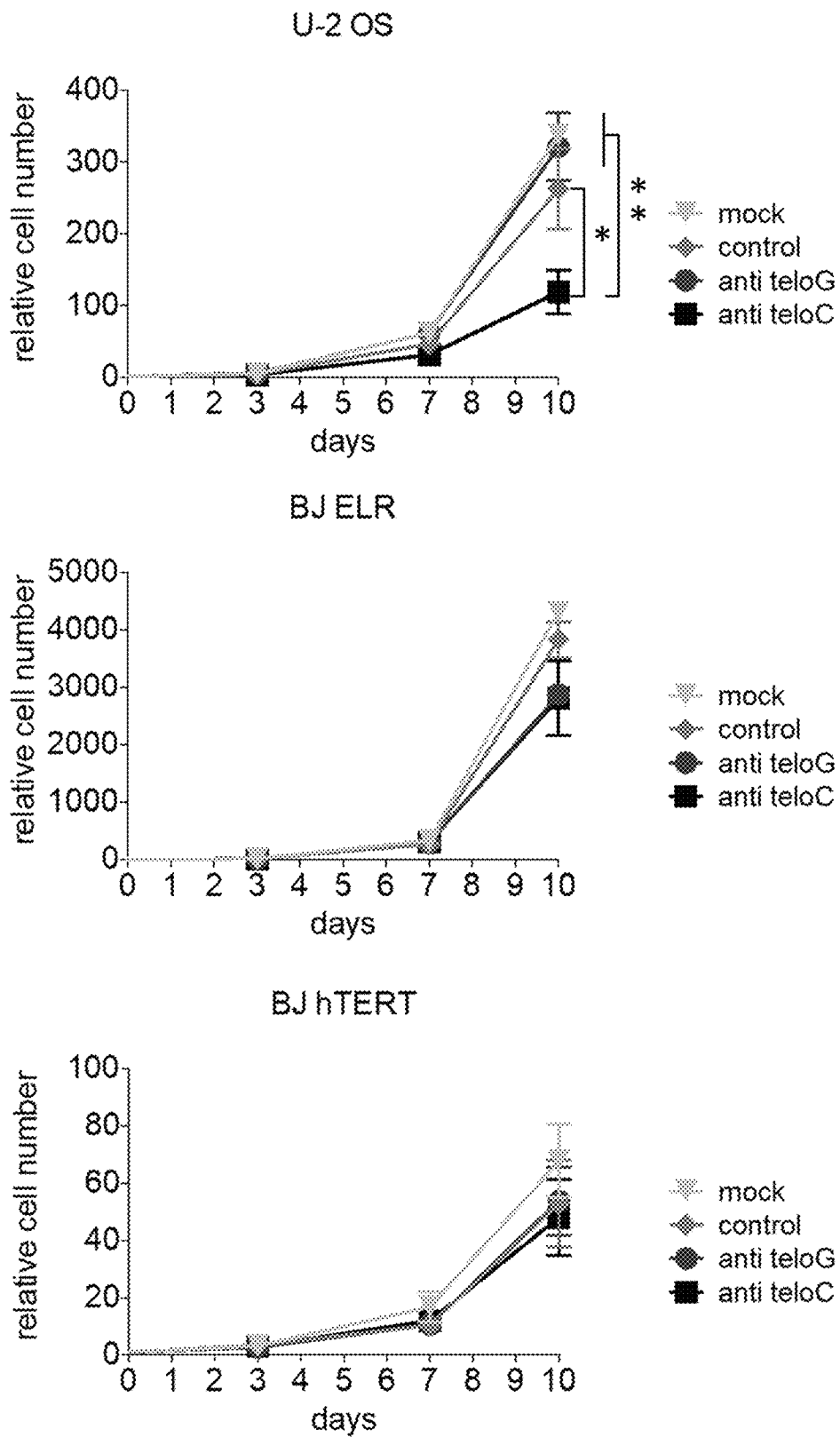

FIG. 4. LNA oligonucleotide with a telomeric sequence reduces cell growth specifically in U-2 OS cells. U-2 OS (ALT or ALT positive), BJ ELR (non-ALT or ALT negative) and BJ hTERT (non-ALT or ALT negative) cells were transfected at day 0, 3 and 7 with the indicated LNA (mock, control, anti TeloG or anti TeloC) at a concentration of 200 nM. Graphs show the relative cell number normalized on day 0 (n=3 independent experiments; *=p value<0.05, **=p value<0.01).

Figure 5:
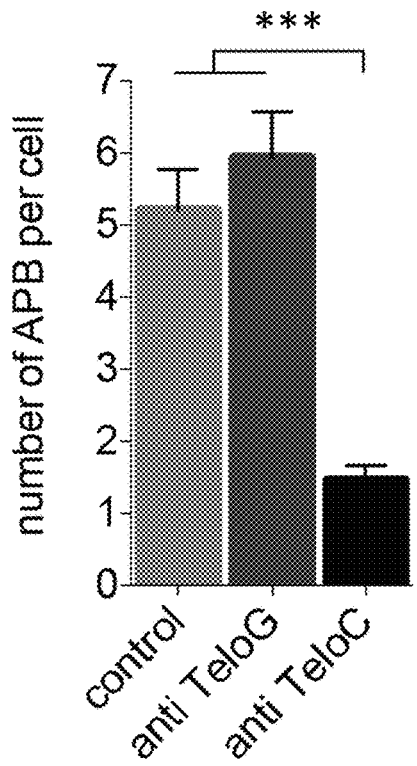

FIG. 5. An LNA oligonucleotide with a telomeric sequence reduces the number of ALT-associated PML bodies (APBs) in U-2 OS. U-2 OS cells were transfected with the indicated LNA at a final concentration of 200 nM and stained for APBs at day 3 post transfection (n=3 independent experiments; **=p value<0.001).

Figure 6:
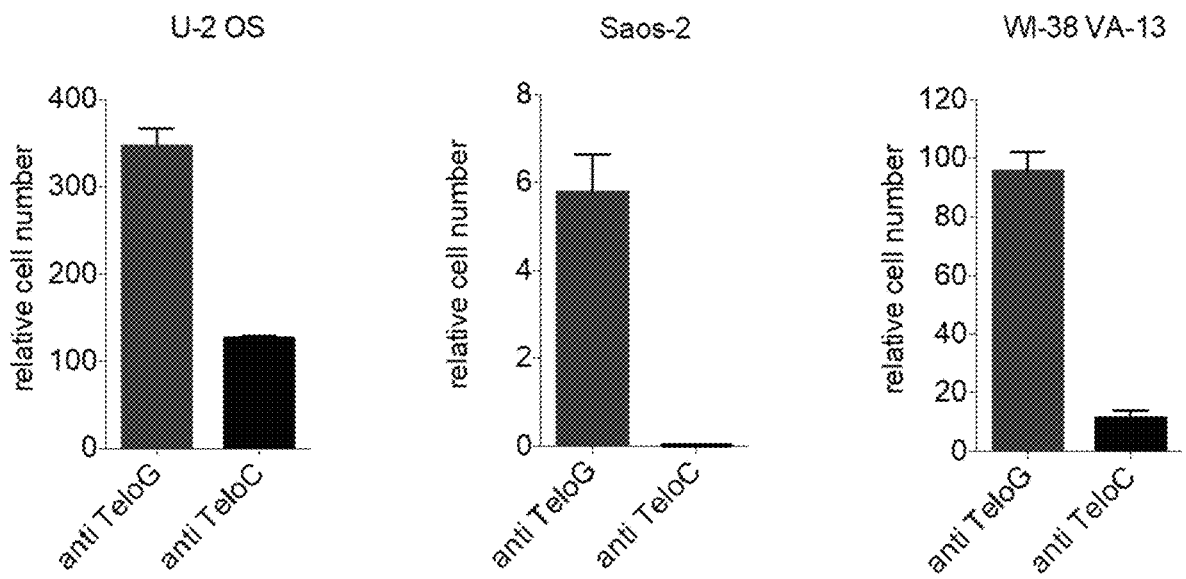

FIG. 6. AN LNA oligonucleotide with a telomeric sequence reduce cell growth in different ALT cell lines. U-2 OS, Saos-2 and WI-38 VA-13 cells were transfected at day 0, 3 and 7 with the indicated LNA at a final concentration of 200 nM. The graphs show the relative cell number at day 10, normalized on day 0.

Figure 7:
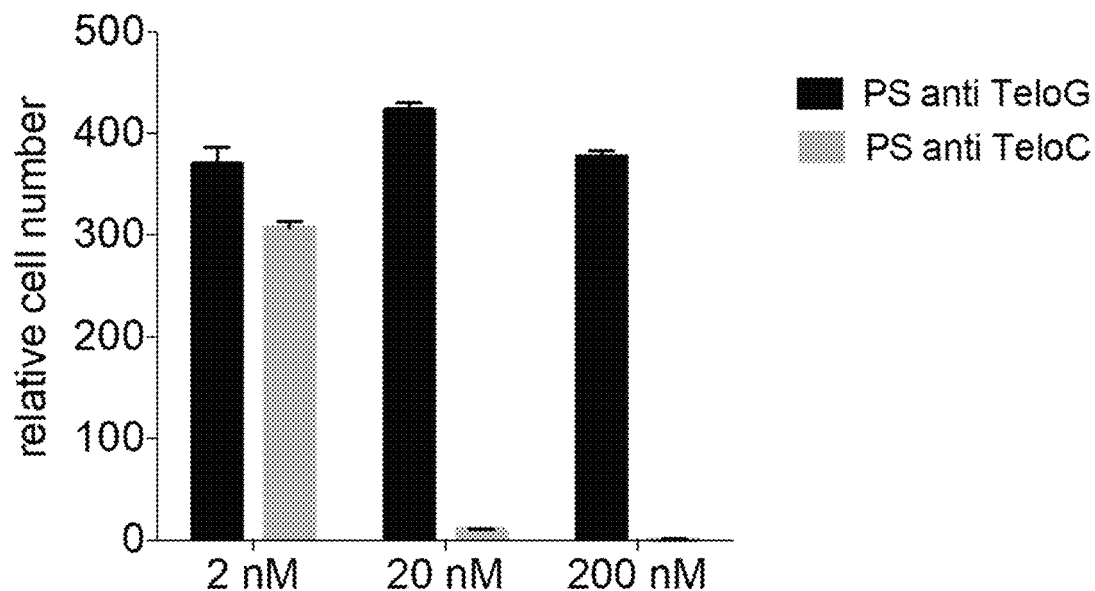
Figure 7:
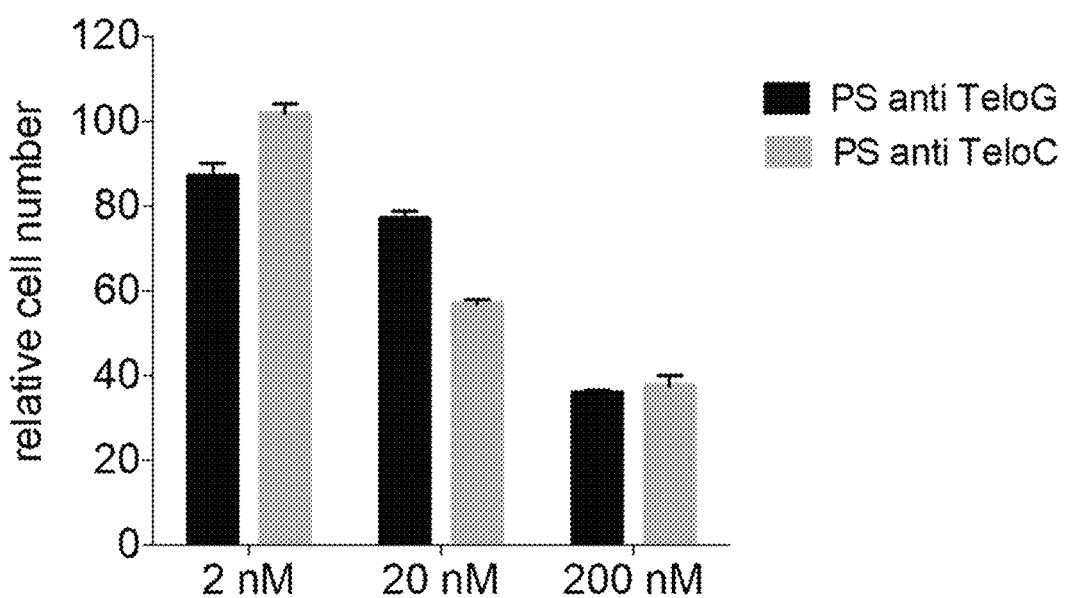

FIG. 7. Phosphorothioate backbone LNA oligonucleotide (PSLNA) with a telomeric sequence is 10 times more effective in inhibiting cell growth and retain specificity for ALT cells. U-2 OS and BJ hTERT cells were transfected at day 0, 3 and 7 with the indicated PS LNA at the indicated concentrations. The graphs show the relative cell number at day 10, normalized on day 0.

Figure 8:
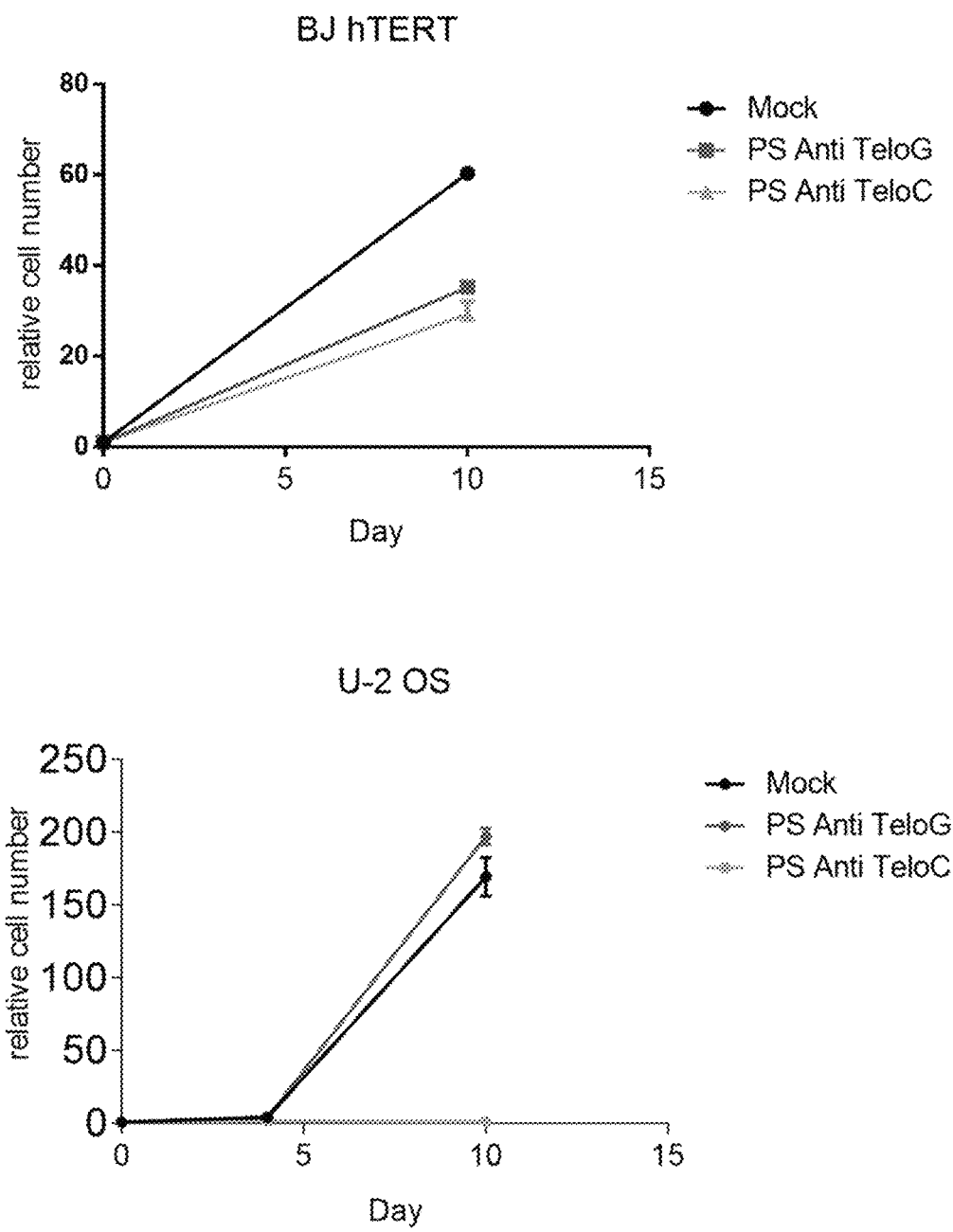

FIG. 8. Phosphorothioate backbone LNA oligonucleotide (PSLNA) with a telomeric sequence is effective in inhibiting cell growth specifically in U-2 OS cells. U-2 OS and BJ hTERT cells were transfected at day 0, 3 and 7 with the indicated PS LNA, at a concentration of 20 nM. Graphs show the relative cell number at day 10, normalized on day 0.

Figure 9:
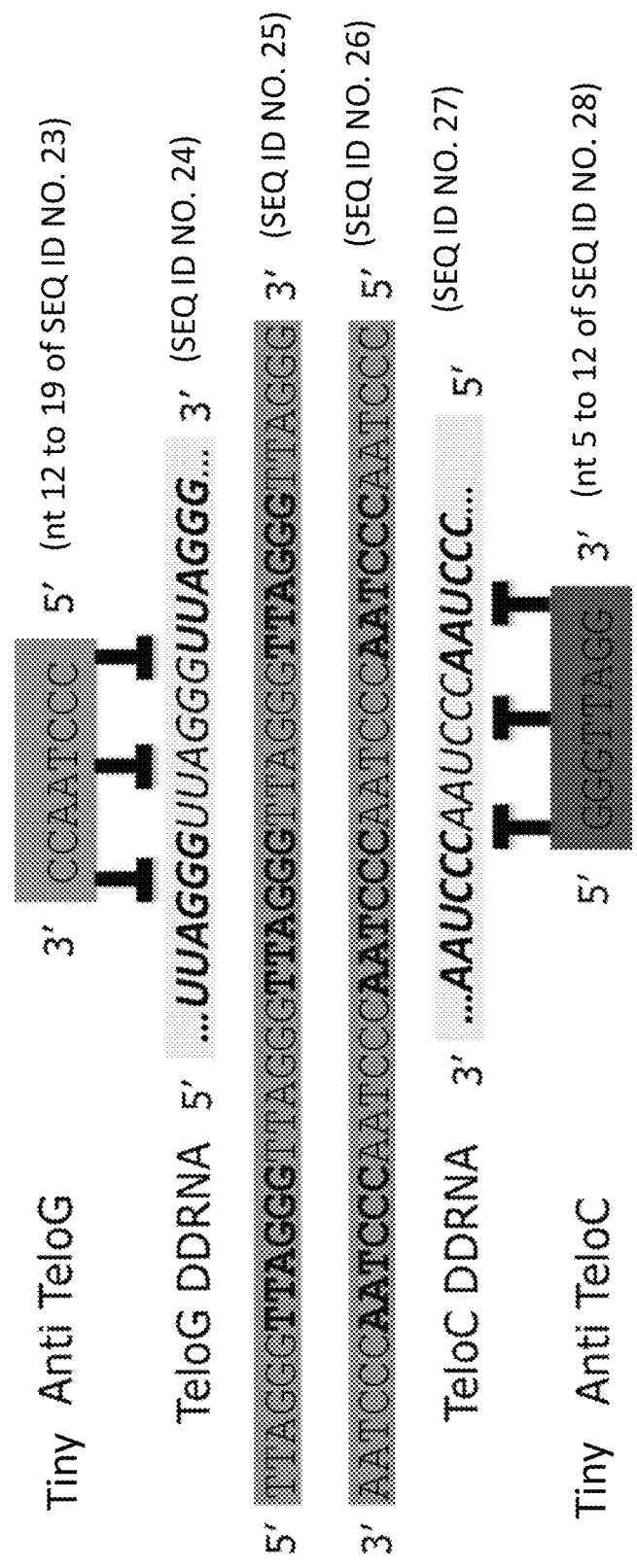

FIG. 9. Schematic of the DDRNA molecules generated at the telomeres and of the tiny LNA oligonucleotides. Tiny LNA molecules can bind and inhibit TeloG and TeloC DDRNAs, thereby having a therapeutic activity. Sequences shown are non-limiting examples of the present invention.

Figure 10:
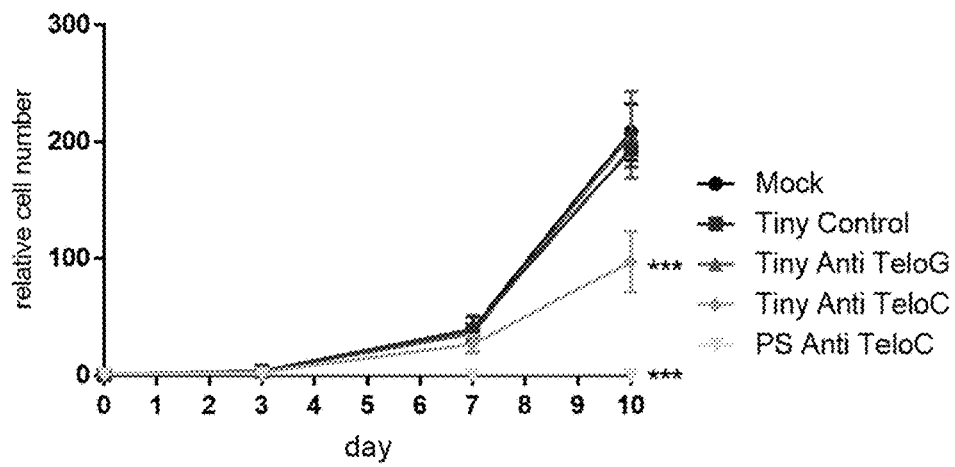

FIG. 10. Tiny anti TeloC LNA oligonucleotide is effective in inhibiting cell growth in U-2 OS cells. U-2 OS cells were transfected at day 0, 3 and 7 with the indicated phosphorothioate LNA, at a final concentration of 20 nM. Graph shows the relative cell growth, as measured by resazurin method (see Materials and Methods), normalized on day 0 (n=3 independent experiments; ***=p value<0.001).

Figure 11:
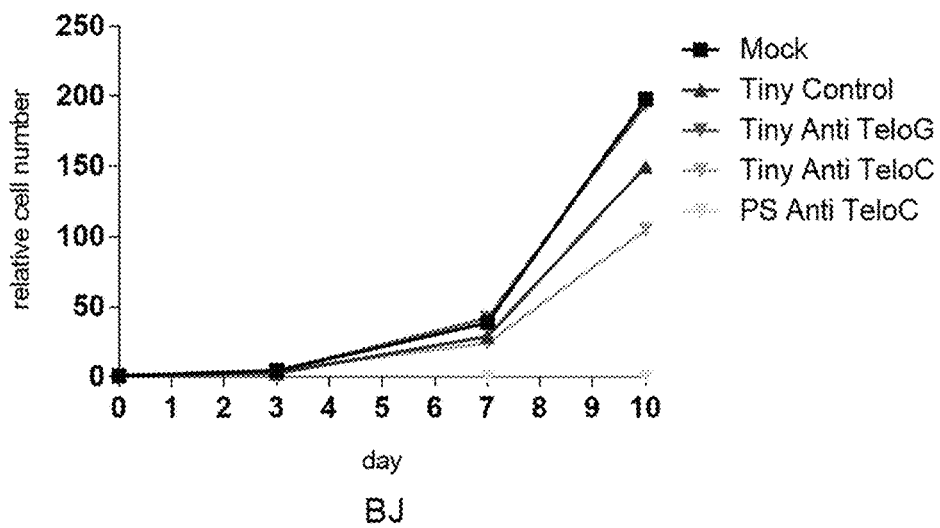
Figure 11:
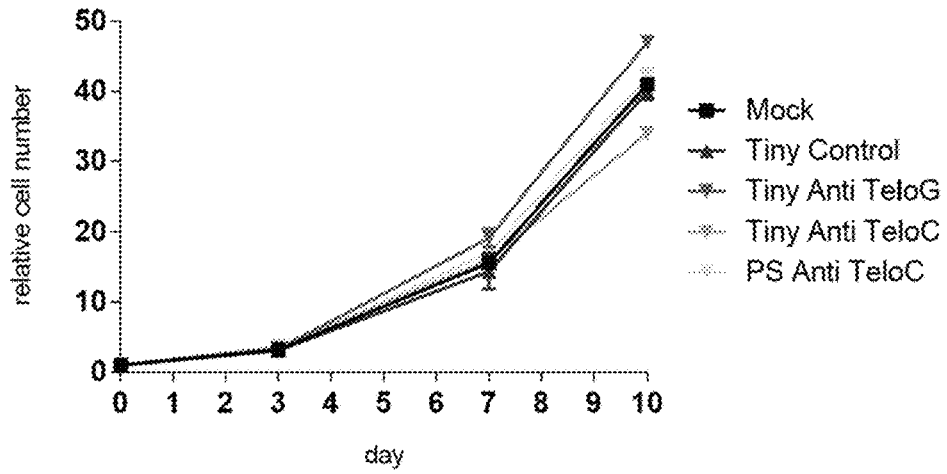

FIG. 11. Tiny anti TeloC LNA oligonucleotide is effective in inhibiting cell growth specifically in U-2 OS cells. U-2 OS and BJ cells were transfected at day 0, 3 and 7 with the indicated LNA, at a concentration of 20 nM. Graphs show the relative cell growth, as measured by resazurin method, normalized on day 0.

Figure 12:
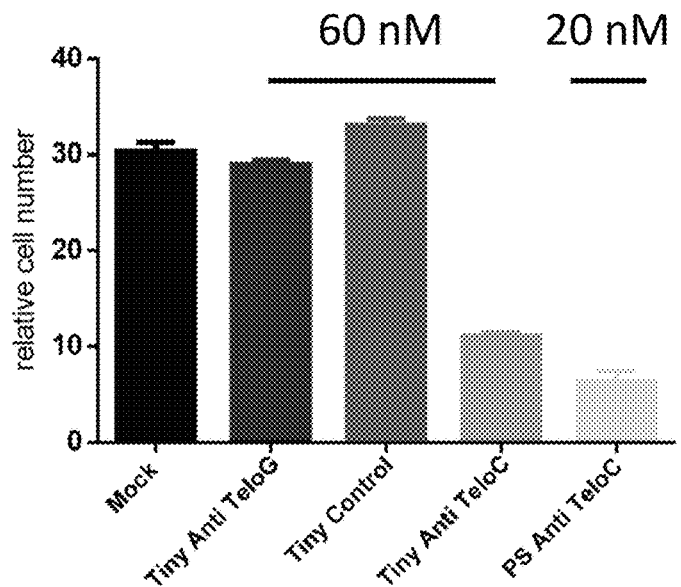

FIG. 12. When used at a 3 fold higher concentration, the Tiny anti TeloC LNA oligonucleotide shows similar efficacy to the PS anti TeloC LNA oligonucleotide in inhibiting cell growth in U-2 OS cells. U-2 OS cells were transfected at day 0 with the indicated phosphorothioate LNA, at a concentration of either 20 nM (PS anti TeloC), or 60 nM (Tiny control, Tiny anti TeloG, Tiny anti TeloC). Graph shows the relative cell growth at day 6, as measured by resazurin method, at day 6 normalized on day 0 FIG. 13. At a 3 fold higher concentration, the Tiny anti TeloC LNA oligonucleotide is specific for U-2 OS cells. U-2 OS and BJ cells were transfected at day 0 with the indicated phosphorothioate LNA, at a concentration of 60 nM (Tiny control, Tiny anti TeloG, Tiny anti TeloC) or 20 nM (PS anti TeloC). Graphs show the relative cell growth, as measured by resazurin method, normalized on day 0.

Figure 14:
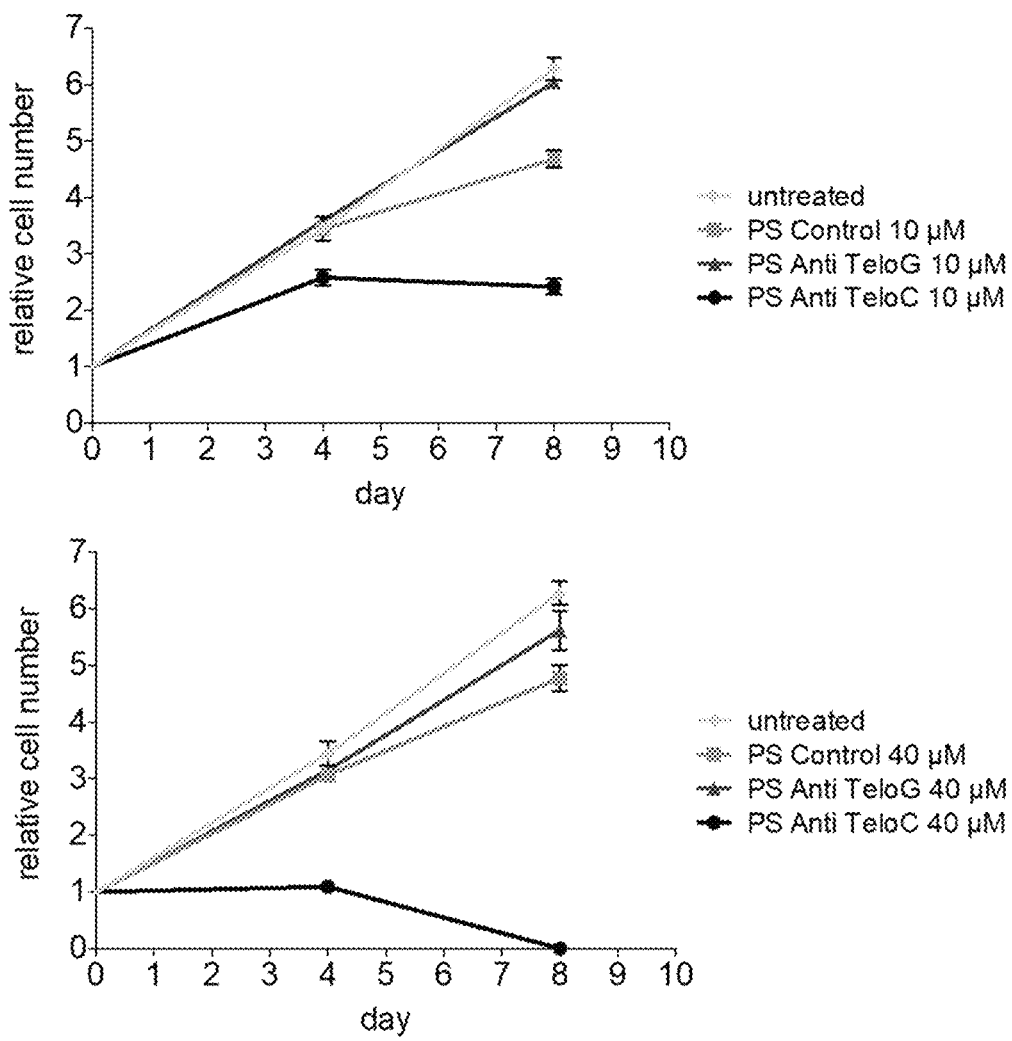

FIG. 14. GBM14 cells are sensitive to naked-delivered PS anti TeloC LNA oligonucleotide in a concentration-dependent manner. GBM14 were incubated with 10 or 40 µM of the indicated PS LNA in the cell culture medium. Graphs show the relative cell growth, as measured by resazurin method, normalized on day 0.

Figure 15:
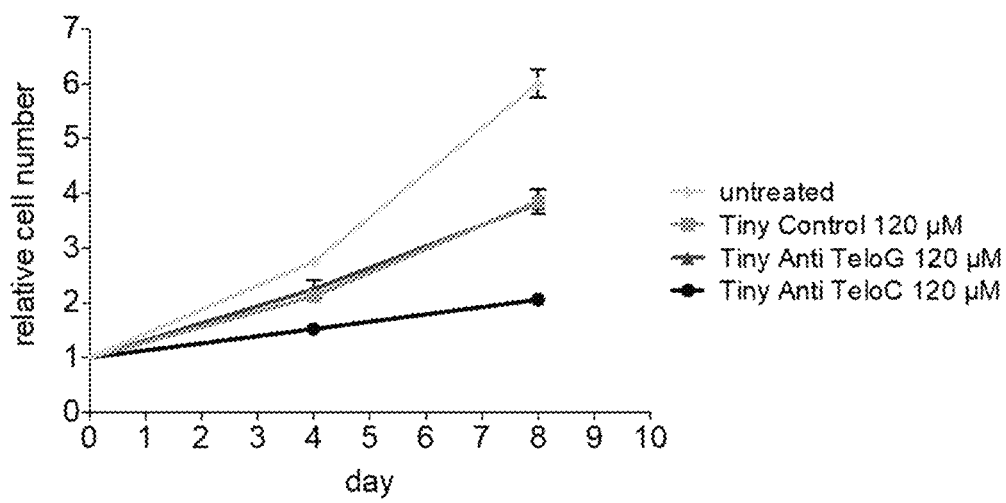

FIG. 15. GBM14 cells are sensitive to naked-delivered tiny anti TeloC LNA oligonucleotide. GBM14 were incubated with 120 µM of the indicated tiny LNA in the cell culture medium. Graph shows the relative cell growth, as measured by resazurin method, normalized on day 0.

Figure 16:
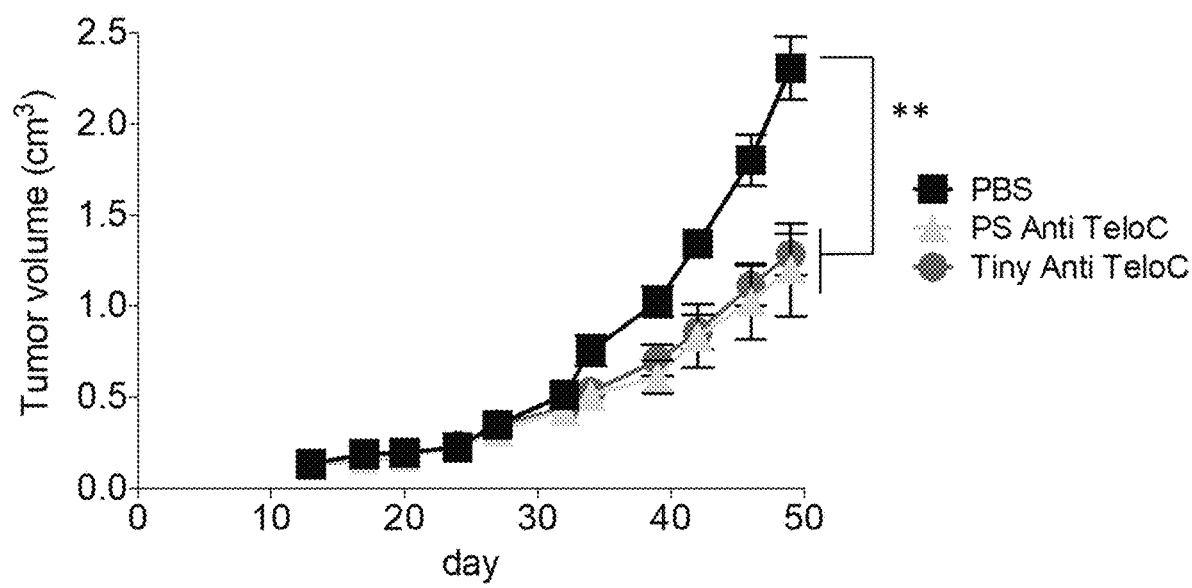

FIG. 16. G292 tumor growth in vivo is reduced upon treatment with PS anti TeloC and tiny anti TeloC. Mice bearing G292 tumors were treated with intraperitoneal injection of the indicated oligonucleotide or PBS as control. (n=7 mice per group; **=p value<0.01).

Figure 17:
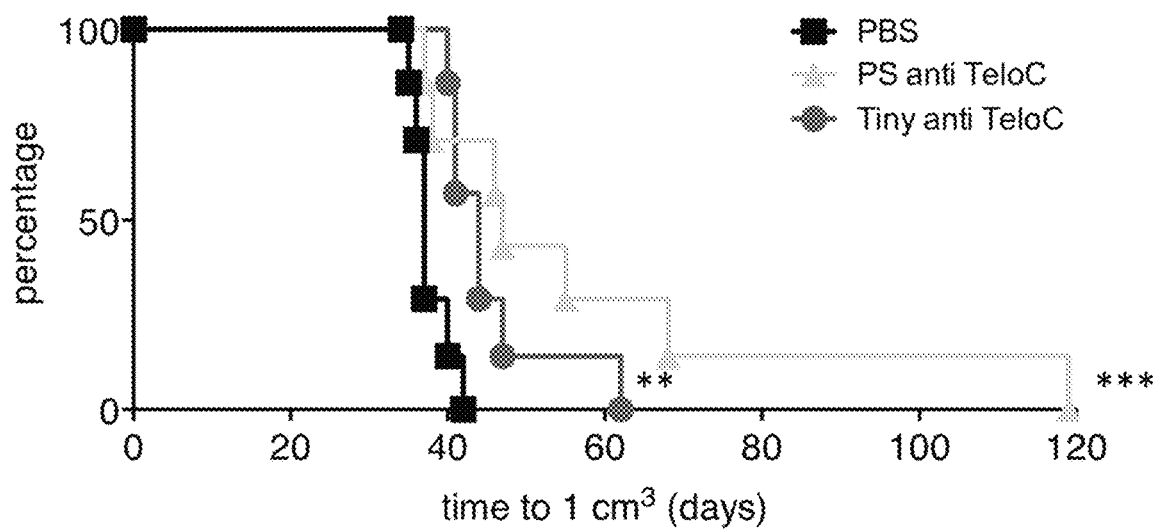

FIG. 17. G292 tumors reached the size of 1 cm$^3$ slower when treated with PS anti TeloC. (n=7 mice per group; =p value<0.01; *=p value<0.001).

Figure 18:
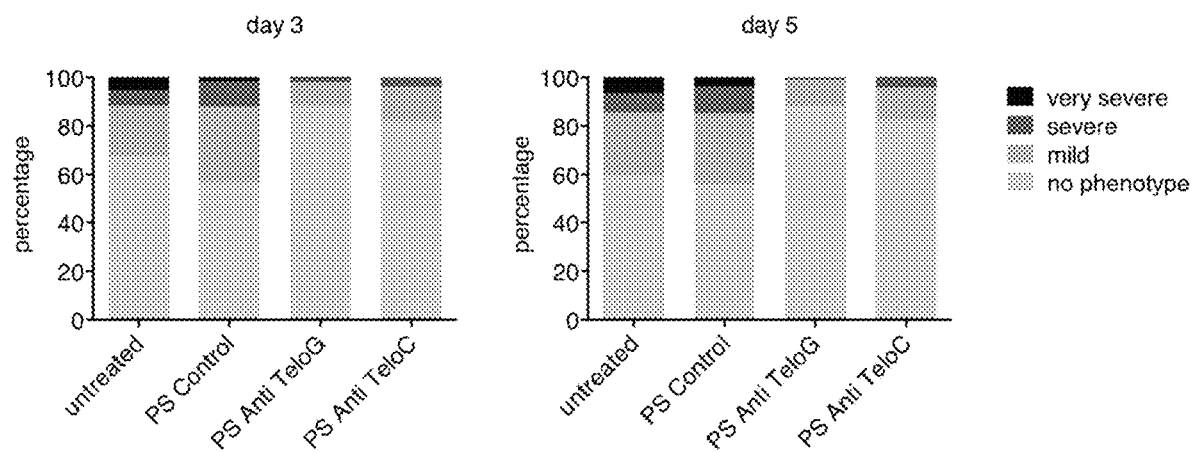

FIG. 18. Second generation telomerase mutant zebrafish treated with PS anti TeloC or anti TeloG show a less severe phenotype. Telomerase mutant zebrafish were injected with the PS LNA and crossed to obtain a second generation. Graphs show the percentage of second-generation fish showing different degrees of severity of morphological defect associated with telomerase mutation (at least 200 fish per sample were analyzed).

Figure 19:
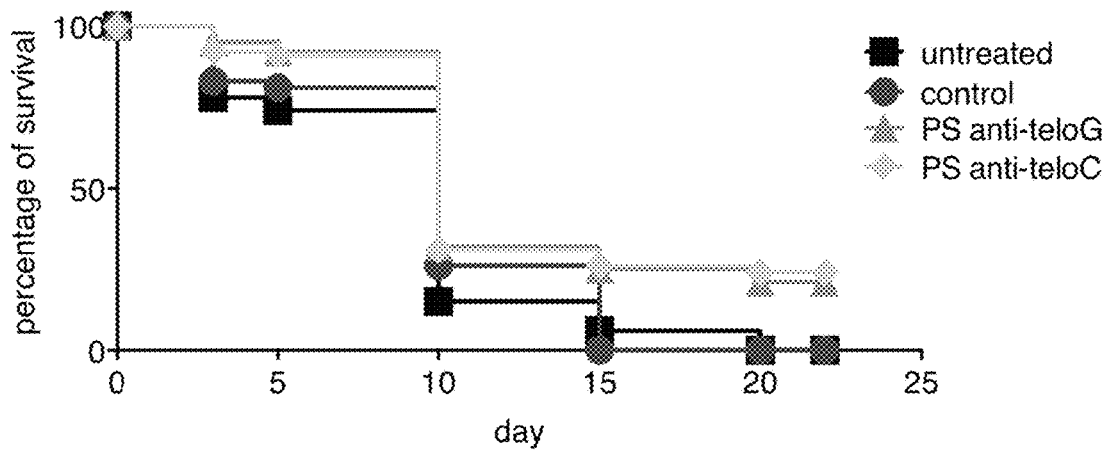

FIG. 19. Second-generation telomerase mutant zebrafish treated with PS anti TeloC or anti TeloG survive longer. Graph shows the survival rate of second generation telomerase mutant zebrafish (at least 200 fish per sample were analyzed).

Figure 20:
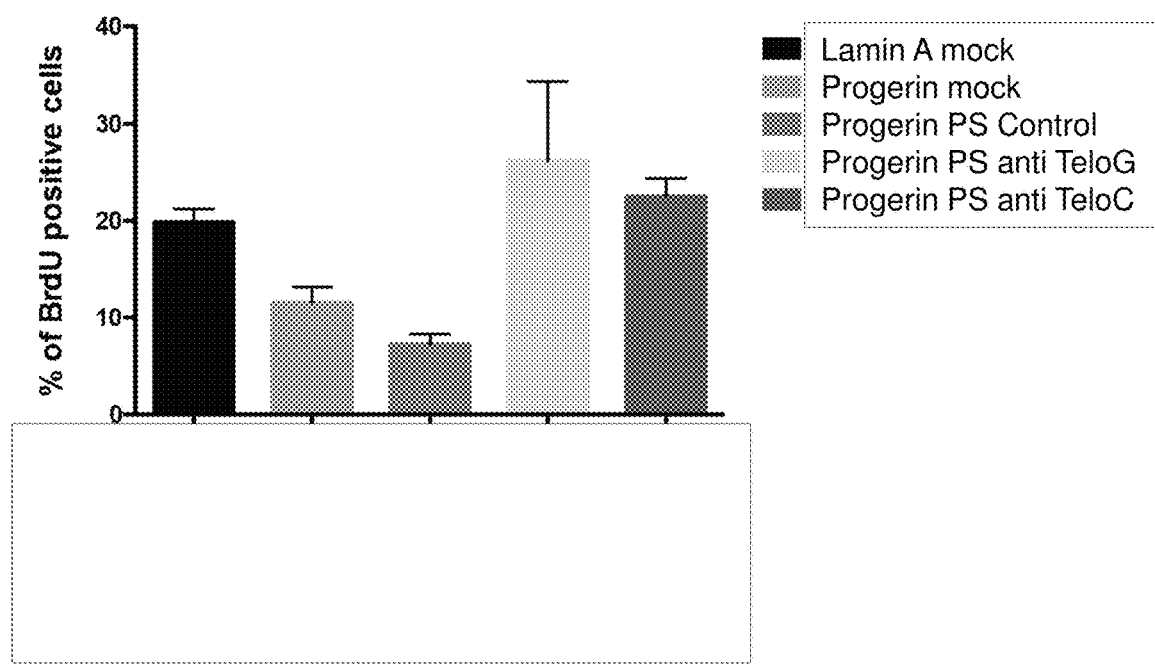
Figure 20:
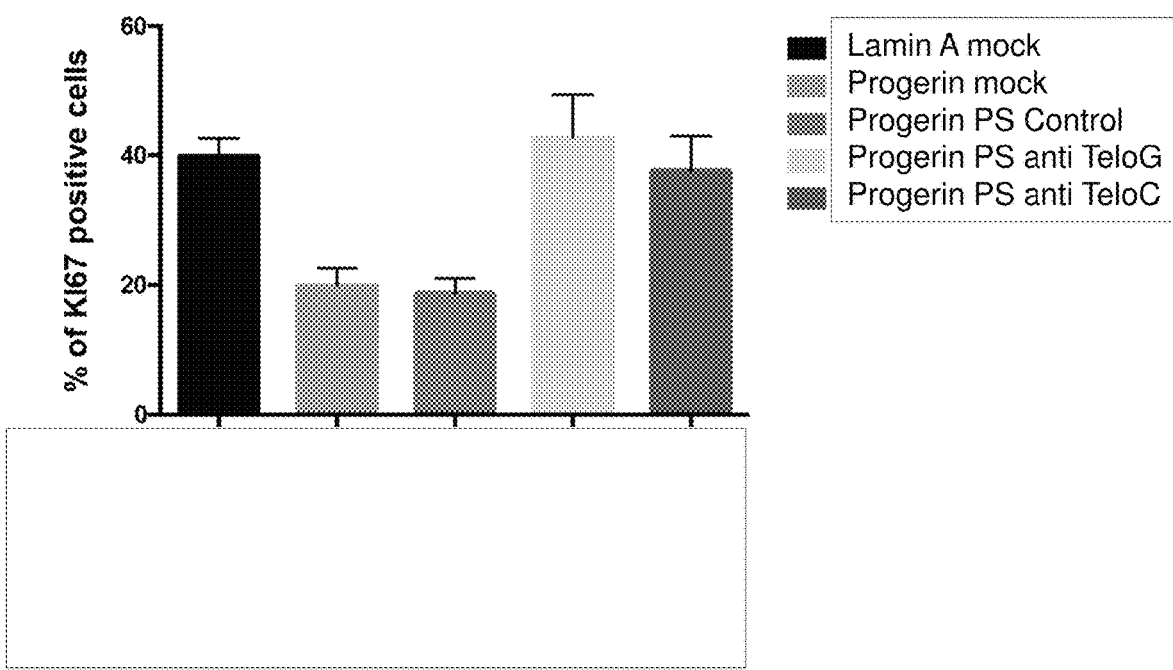

FIG. 20. PS anti TeloG and anti TeloC prevents cell growth in Progerin-expressing cells. Retroviral infected BJ cells expressing either Lamin A or Progerin were transfected with the indicated PS LNA (20 nM). Cells were fixed and stained after an 8-hour-BrdU pulse for immunofluorescence. Antibodies against BrdU and KI67 were used for quantification.

Figure 21:
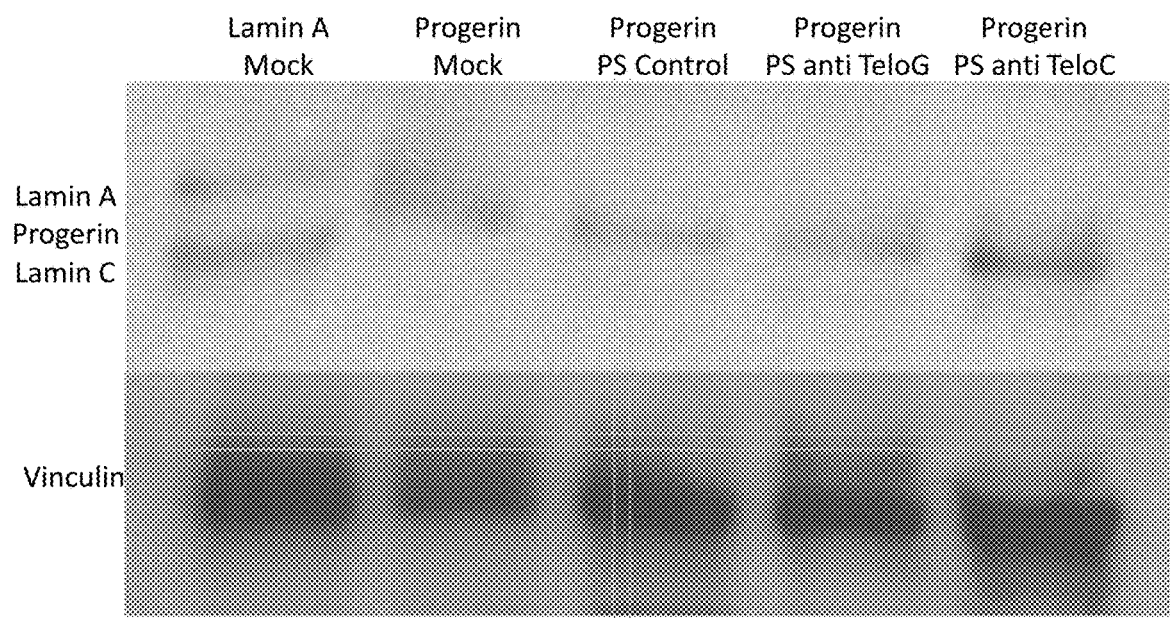

FIG. 21. Progerin is expressed at similar levels in PS LNA-treated samples. Retroviral infected BJ cells expressing either Lamin A or Progerin were probed for Lamin (which detects both isoform A and C), Progerin, and vinculin expression as loading control.

Figure 22:
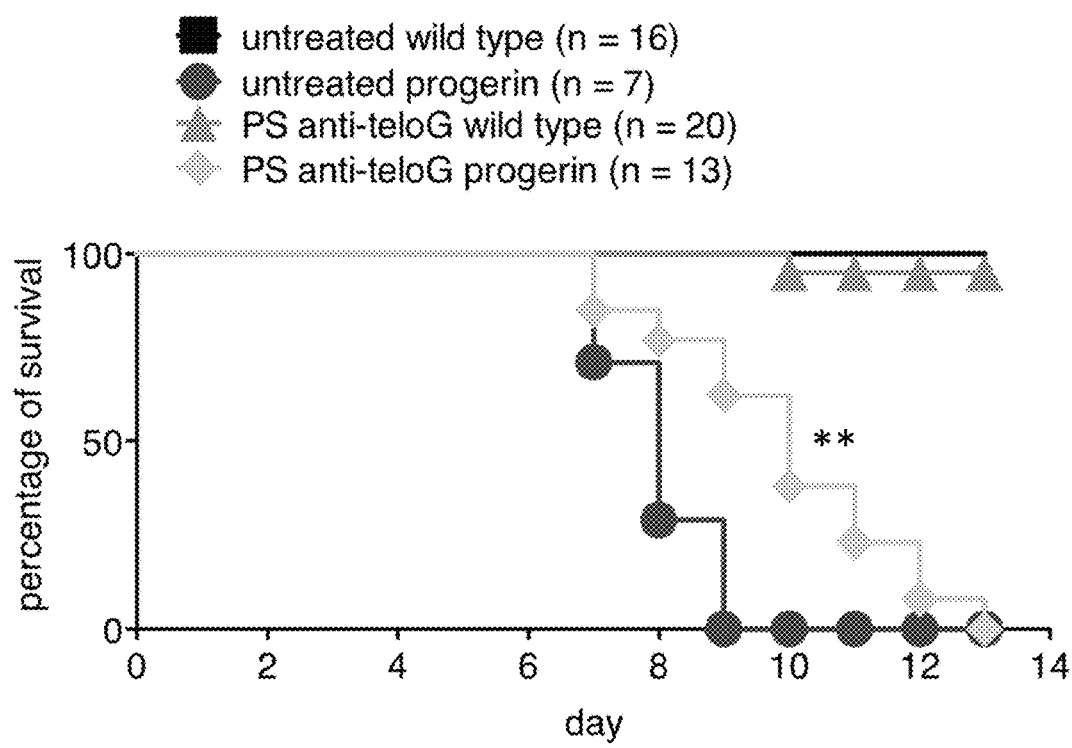

FIG. 22. PS anti TeloG increases survival rates in a mouse model of progerin expression in the skin. Graph shows the survival rate of HGPS (progerin-expressing) and wild type mice, treated with PS anti TeloG LNA oligonucleotide compared with untreated mice (n represents the number of mice analyzed per each group).

Figure 23:
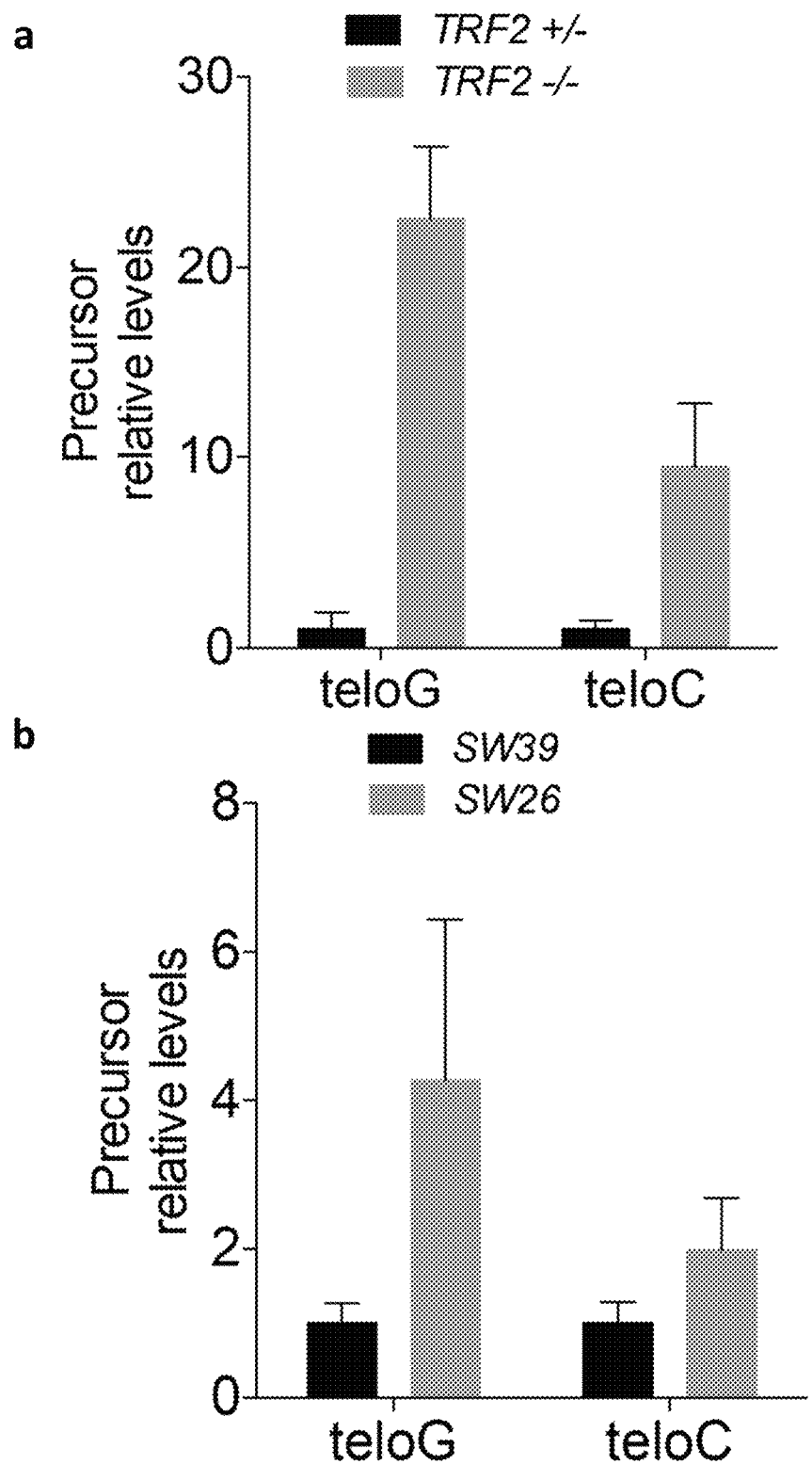

FIG. 23. Detection of telomeric precursor transcripts. (a) Total cell RNA was isolated from MEFs (mouse embryonic fibroblasts) of the indicated genotype and used for strand-specific RT-qPCR to detect telomeric precursor transcripts. (b) Same RT-qPCR as in (a) was used to detect telomeric precursor transcripts from human fibroblasts. Total cell RNA was isolated from SW39 (non-ALT) and SW26 (ALT) for the right panel.

Figure 24:
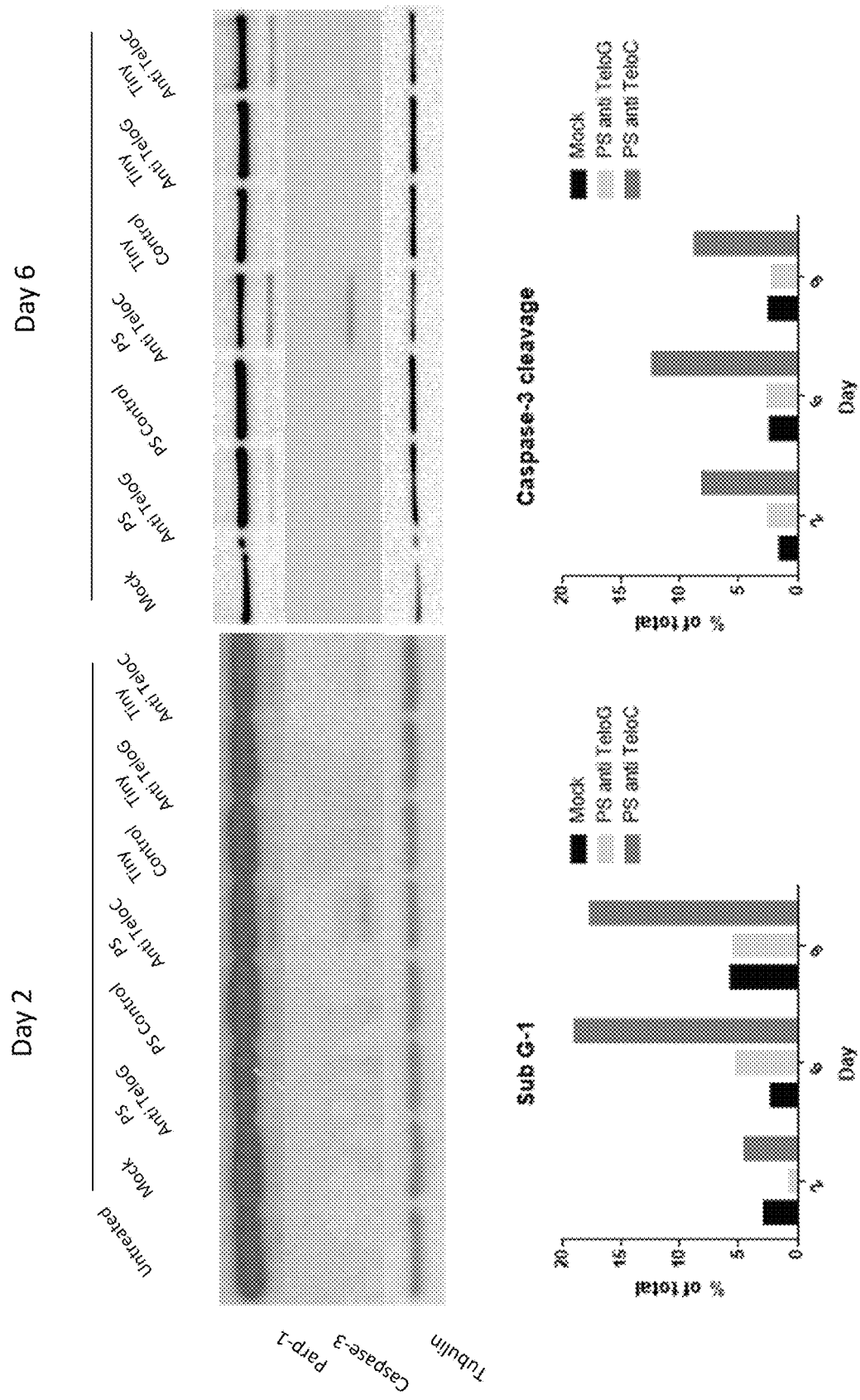

FIG. 24. Activation of apoptosis pathways in ALT cells upon anti TeloC treatment. U-2 OS cells were treated with the indicated LNAs. PS LNAs were transfected at 20 nM, while Tiny LNAs were transfected at 60 nM. Cells were transfected on day 0, 3, and 7. Samples were harvested on the indicated days for protein detection of apoptosis markers, Caspase 3 and Parp-1 cleavages, or for FACS analysis (Sub G1 fraction and caspase 3 cleavage).

Figure 25:
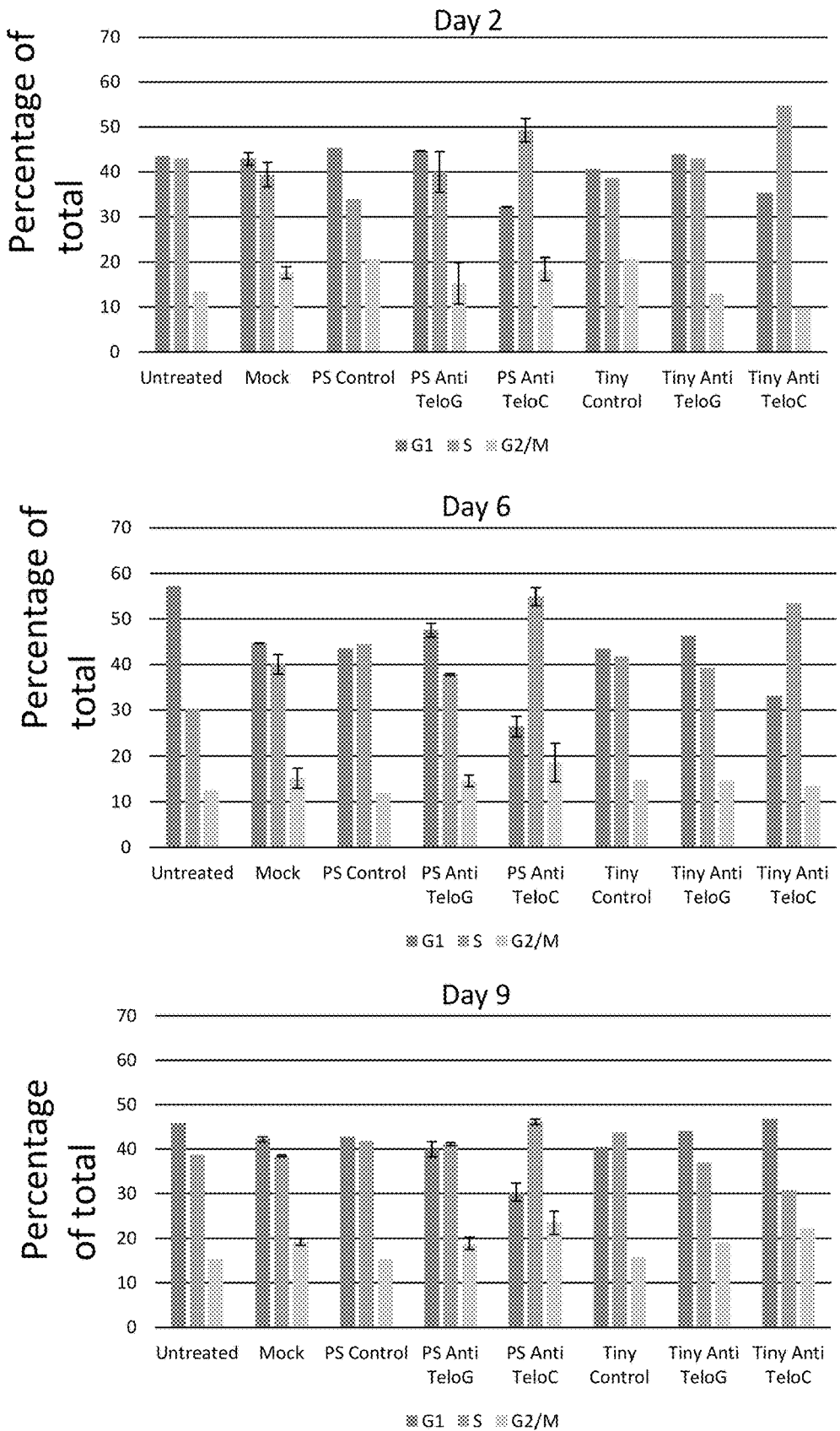

FIG. 25. Anti TeloC LNA induces a lengthened S-phase in ALT cells. U-2 OS cells were transfected with the indicated LNAs, PS LNA at 20 nM, and Tiny LNA at 60 nM, on day 0, 3, and 7. Cells were Harvested on day 2, 6, and 9 for FACS analysis of cell cycle.

Figure 26:
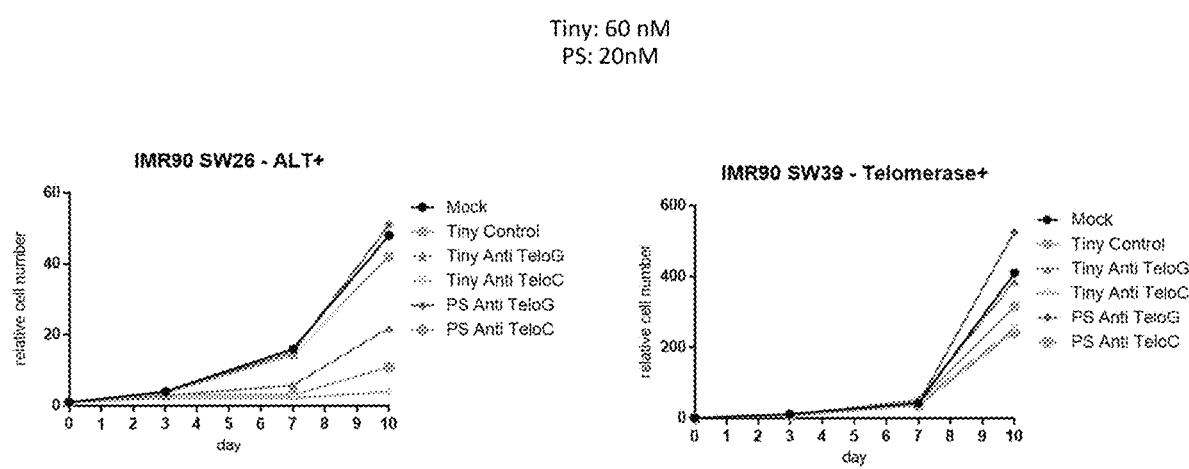

FIG. 26. Anti TeloC LNA is an ALT-specific inhibitor. Cell lines were transfected with the indicated LNAs, PS LNA at 20 nM, and Tiny LNA at 60 nM, on day 0, 3, and 7. Graphs show the relative cell number as measured by resazurin values normalized to day 0.

Figure 27:
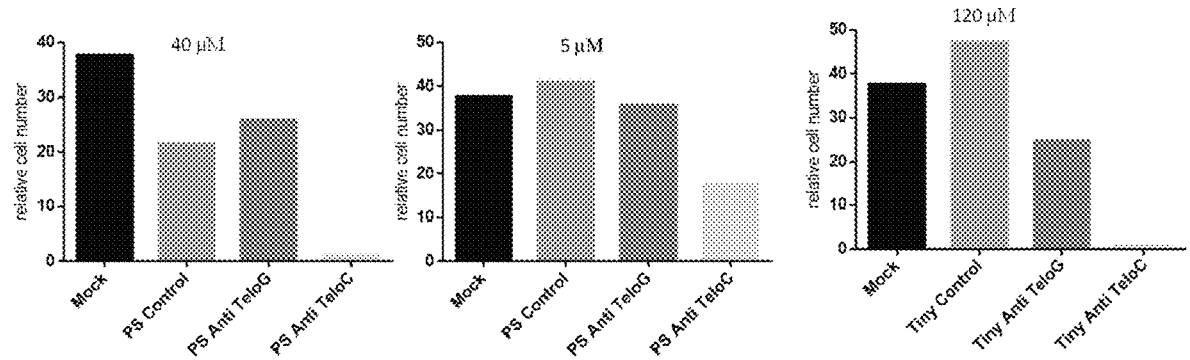
Figure 27:
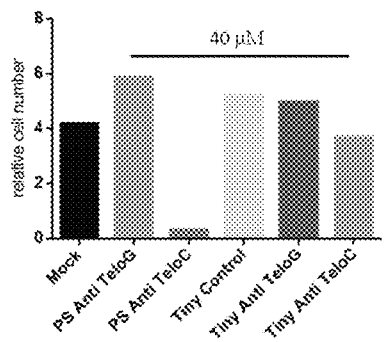

FIG. 27. Naked delivery of LNA is sufficient to inhibit U-2 OS cell growth. (A) U-2 OS cells were treated with LNA at the indicated concentrations on day 0. Graphs show the relative cell number at day 7 as measured by resazurin values normalized to day 0. (B) U-2 OS cells were treated as in (A), while the cell number measured at day 6.

Figure 28:
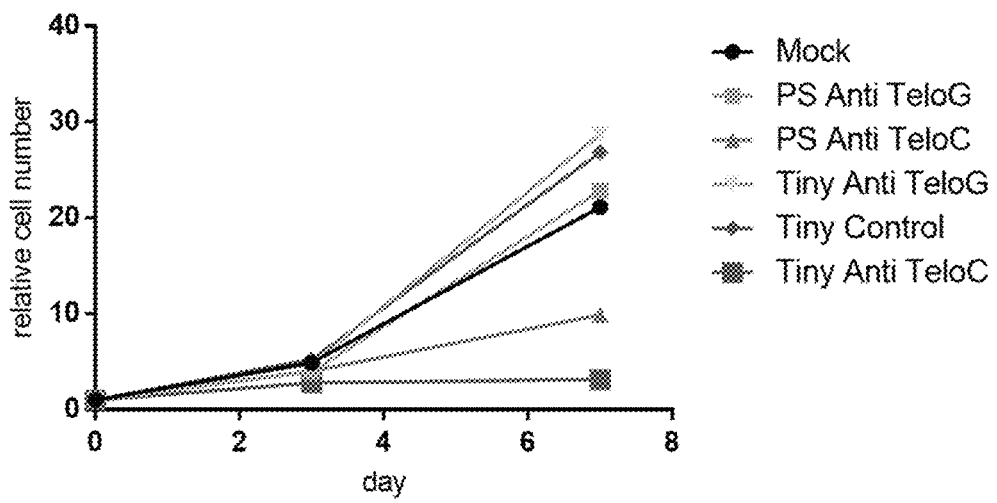

FIG. 28. G-292 growth is inhibited by anti TeloC LNA. G-292 was transfected with the indicated LNAs at 200 nM on day 0 and 3. The graph shows the relative cell number as measured by resazurin values normalized to day 0.

Figure 29:
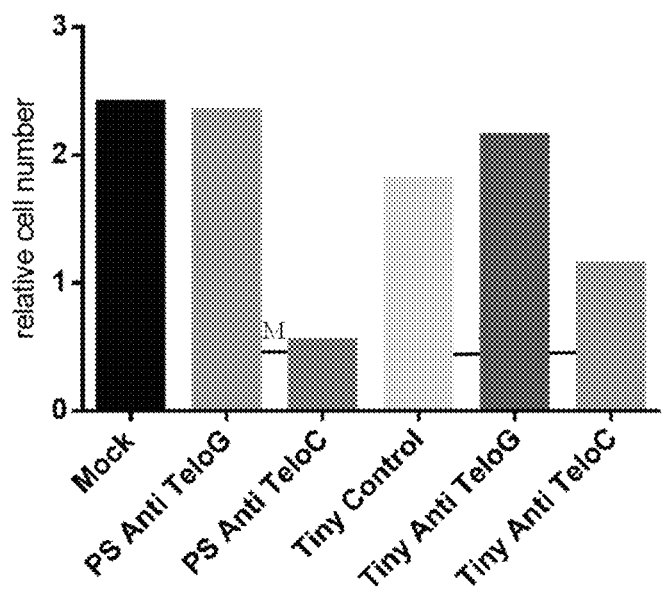

FIG. 29. Naked delivery of LNA is sufficient to inhibit G-292 cell growth. G-292 cells were treated with LNA at the indicated concentrations on day 0. The graph shows the relative cell number at day 7 as measured by resazurin values normalized to day 0.

Figure 30:
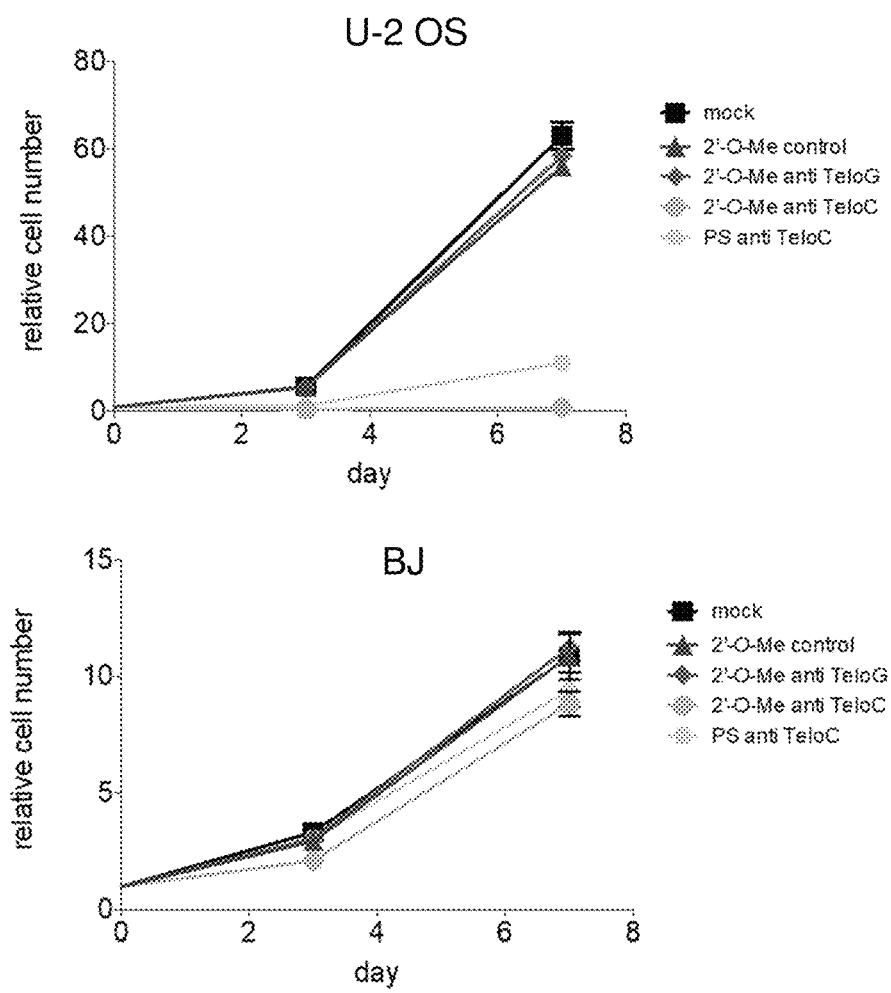

FIG. 30. 2'-O-Methyl (2'-O-Me) ASO anti TeloC ASO is effective in inhibiting cell growth specifically in U-2 OS cells. U-2 OS and BJ cells were transfected at day 0 with the indicated 2'-O-Me ASO or PS anti TeloC, at a concentration of 20 nM. Graphs show the relative cell number as measured by resazurin values normalized to day 0.

Figure 31:
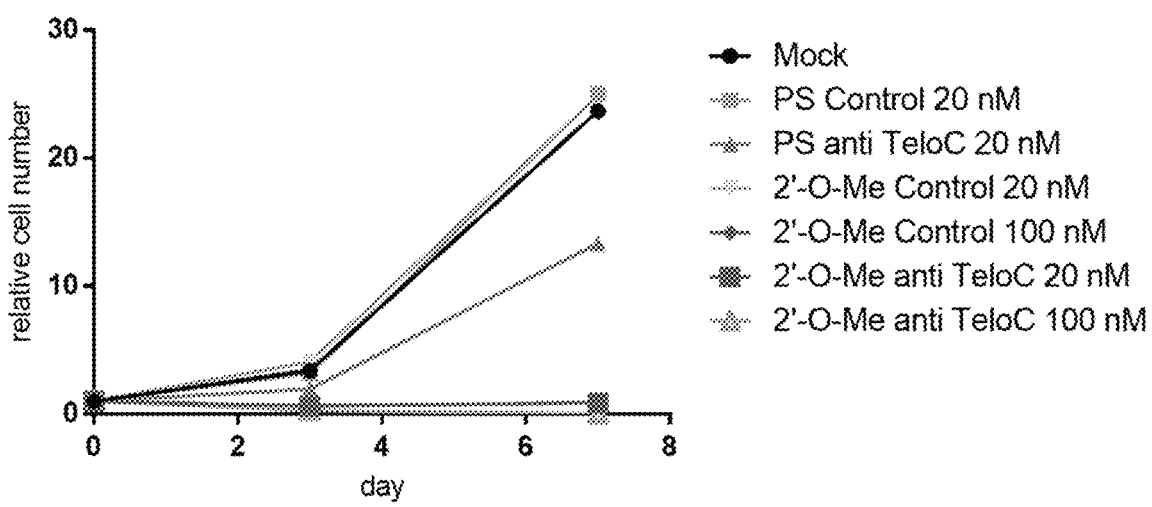

FIG. 31. 2'-O-Me ASOs are non-toxic up to 100 nM. U-2 OS cells were transfected on day 0 with the indicated ASOs, at the indicated concentration. Graphs show the relative cell number as measured by resazurin values normalized to day 0.

DETAILED DESCRIPTION OF THE INVENTION

Materials and Methods

Cultured cells: MEFs CRE-ER TRF2$^{fl/fl}$ and MEFs CRE-ER TRF2$^{fl/+}$ (Celli and de Lange, 2005) were grown in DMEM supplemented with 10% fetal bovine serum and 1% glutamine; for CRE activation and TRF2 knock out induction, cells were treated with 600 nM of 4 hydroxytamoxifen for 24 hours and analysed 24 hours later. U-2 OS cells (ATCC) were grown in DMEM supplemented with 10% fetal bovine serum and 1% glutamine. Saos-2 cells (ATCC) were grown in McCoy's 5A+Glutamax supplemented with 15% fetal bovine serum. WI-38 and WI-38 VA-13 (ATCC) were grown in MEM+Glutamax supplemented with 10% fetal bovine serum, 10 mM non-essential amino acids and 1 mM sodium pyruvate. The telomerase-positive cell line SW39 (ALT negative) and the ALT-positive cell line SW26 (Bechter et al., 2003) were grown in in a 4:1 mixture of Dulbecco modified Eagle medium-medium 199 supplemented with 10% defined supplemented bovine calf serum. BJ hTERT were obtained by retroviral infection of BJ cells (ATCC) with a human telomerase expressing plasmid, and were grown in MEM+Glutamax supplemented with 10% fetal bovine serum, 10 mM non-essential amino acids and 1 mM sodium pyruvate. BJ ELR (Hahn et al., 1999) were grown in DMEM:M199 4:1 supplemented with 10% fetal bovine serum, 1% glutamine, 1 mM sodium pyruvate and 25 mM HEPES. GBM14 (ALT positive) were grown in DMEM/F12 with GlutaMAX supplemented with 2% of B27, 5 µg/ml Heparin, 20 ng/ml of bFGF and 20 ng/ml of EGF. G-292 (ATCC) were grown in McCoy's 5A+Glutamax supplemented with 10% fetal bovine serum and 1% glutamine.

Transfection: LNA were boiled at 90° C. for 5 minutes and chilled in ice for 5 minutes before transfection with Lipofectamine RNAiMAX (Invitrogen) according to the manufacturer's instructions at the indicated final concentration. Mock-transfected cells were treated with RNAiMAX only.

Growth curves: At each indicated time point cells were counted in triplicate with a Coulter Counter (Beckman) or with the In Vitro Toxicology Assay Kit, Resazurin based (Sigma), which allows a spectrophotometric measurement of metabolic activity of living cells, in accordance with the manufacturer's instructions.

Immunofluorescence: Cells were fixed with 1:1 methanol/acetone solution for 2 minutes at room temperature. After blocking, cells were stained with anti PML (Santa Cruz) primary antibody for 1 hour at room temperature, washed and incubated with conjugated anti mouse secondary antibodies for 40 minutes at room temperature. Nuclei were stained with DAPI (1 µg/ml). Confocal sections were obtained with a Leica TCS SP2 AOBS confocal laser microscope by acquisition of optical z sections at different levels along the optical axis and number of APBs per cell was counted by CellProfiler software.

RNA isolation: Total cellular RNA was extracted using mirVana™ miRNA Isolation kit (Life Technologies) according to the manufacturer's instructions.

qPCR of small RNA: cDNA synthesis and RT-PCR were performed using the miScript PCR system (Qiagen). RNA was fractionated by running 5 µg of total RNA on a polyacrylamide denaturing gel. RNA species shorter than 40 nucleotides were gel extracted and cDNA was synthesized using the miScript II RT kit with HiSpec buffer. Reactions were incubated at 37° C. for 60 min followed by a heat-inactivation step for 5 min at 95° C. cDNA was analysed using the miScript SYBR Green PCR Master Mix, miScript Universal Primer, mir29b primer (TAGCACCATTT-GAAATCAGTGTT) SEQ ID No. 7, Spike-In primer (CGAATTCCACAAATTGTTATCC) SEQ ID No. 8 to monitor efficiency of RNA extraction from gel and telomere sequence-containing primers (TAGGGTTAGGGT-TAGGGT, SEQ ID No. 9, CCCTAACCCTAACCCTAA SEQ ID No. 10).

Strand specific qPCR: Total RNA coming from mirVana™ miRNA Isolation Kit was used. Samples were treated with DNase I (Thermo Scientific) to remove any potential residual genomic DNA contamination. 1000 ng of total RNA were reverse-transcribed using the Superscript First Strand cDNA synthesis kit (Invitrogen) with strand-specific primers. Primers for reverse-transcription used: RPP0rev for the detection of the housekeeping Rplp0 mRNA; teloCrev for the detection of G-rich-stranded telomeric precursor; teloGrev for the detection of C-rich-stranded telomeric precursor.

RT-qPCR was performed using Roche SYBR green. For each RT-qPCR reaction, 50 ng of cDNA were used. To amplify telomeric repeats the inventors adapted a technique described in (Cawthon, 2002), which allows the generation of a fixed-length amplification product. Primers for qPCR used: RPP0fwd and RPP0rev for the detection of the housekeeping Rplp0 mRNA; teloF and teloR for the detection of telomeric precursors.

Below, the list of primers (5'-3' orientation) used for strand-specific RT-qPCR:

RPP0fwd:
(SEQ ID No. 11)
TTCATTGTGGGAGCAGAC

RPP0rev:
(SEQ ID No. 12)
CAGCAGTTTCTCCAGAGC teloCrev:
(SEQ ID No. 13)
CCCTAACCCTAACCCTAA teloGrev:
(SEQ ID No. 14)
TAGGGTTAGGGTTAGGGT teloF:
(SEQ ID No. 15)
CGGTTTGTTTGGGTTTGGGTTTGGGTTTGGGTTTGGGTT teloR:
(SEQ ID No. 16)
GGCTTGCCTTACCCTTACCCTTACCCTTACCCTTACCCT Targeted sequencing of small RNA. Two linkers were ligated to the two ends of the RNA molecules in the sample to be analysed. The 3' end of the starting RNA was ligated to a monoadenylated DNA linker by a T4 RNA ligase 2 truncated enzyme (NEB) incubated for 1 hour at 25° C. The 5' RNA linker was then ligated by a T4 RNA ligase 1 (NEB) to the target RNA at 20° C. for 1 hour, after removing the 5' cap structure by Tobacco Acid Pyrophosphatase (Epicentre), incubated at 37° C. for 1 hour. Linkers enabled cDNA synthesis using PrimeScript RT-PCR Kit (Takara). The reverse transcription reaction was incubated at 44° C. for 1 hour. Subsequent PCR amplification using Phusion® High-Fidelity DNA Polymerase (NEB) was carried out as follows: 98° C. 2 minutes; 22 cycles of: 98° C. for 30 seconds, 55° C. for 30 seconds, 72° C. for 30 seconds; 72° C. for 5 minutes; hold at 4° C. To capture the amplified cDNA targets, complementary RNA baits containing biotin-labeled nucleotides were used. These RNA baits were produced by using AMbion MAXIscript T7 In Vitro Transcription kit (Life Technologies) and Biotin RNA labelling Mix (Roche). A T7-promoter-containing dsDNA was incubated at 37° C. for 1 hour to allow for in-vitro transcription. RNA baits and cDNA targets were incubated at 37° C. for 48 hours in the presence of SUPERase-inhibitor (Life Technologies) and of the following blocking agents: Human Cot-1 (Life Technologies), UltraPure™ Salmon Sperm DNA Solution (Thermo Scientific) and a 200 uM Customized Block. The hybrid RNA-cDNA molecules were captured by Dynabeads® MyOne™ Streptavidin C1 (Life Technologies) beads, while non-targeted cDNAs were washed away. Captured cDNAs were then barcoded by PCR with Script Index PCR primers (Illumina) and sequenced by a MiSeq (Illumina) sequencer. Oligonucleotide sequences (5'-3' orientation) were:

3' DNA linker
(SEQ ID No. 17)
AGATCGGAAGAGCACACGTCTGAACTCCAGTCAC-Amine

5' RNA linker
(SEQ ID No. 18)
ACACUCUUUCCCUACACGACGCUCUUCCGAUCU

RT primer
(SEQ ID No. 29)
GTGACTGGAGTTCAGACGTGTGCTCTTCCGATCT

```
                                -continued
PCR Fw
                                            (SEQ ID No. 30)
AATGATACGGCGACCACCGAGATCTACACTCTTTC

CCTACACGACGCTCTTCCGATCT

PCR Rv
                                            (SEQ ID No. 31)
CAAGCAGAAGACGGCATACGAGATCGGTCTCGGCA

TTCCTGCTGAACCGCTCTTCCGATCT

Block Fw
                                            (SEQ ID No. 32)
AATGATACGGCGACCACCGAGATCTACACTCTTTC

CCTACACGACGCTCTTCCGATCT

Block Rv
                                            (SEQ ID No. 33)
CAAGCAGAAGACGGCATACGAGATCGTGATGTGAC

TGGAGTTCAGACGTGTGCTCTTCCGATCT
```

Western blot: Cells were collected in lysis buffer TEB150 (50 mM Hepes, 150 mM NaCl, 2 mM MgCl2, 5 mM EGTA, 0.5% Triton, 10% glycerin), and flash frozen in liquid nitrogen until sample preparation for western blot. To lyse, cells were thawed on ice, spun for 15 minutes at +4° C. and 13200 RPM. The protein-containing supernatant was saved, and cell debris trashed. Proteins were quantified using the Bradford assay. After transfer, membranes were probed with an anti-caspase-3 antibody (Cell Signaling 9661), an anti-PARP antibody (Serotec), and an anti-tubulin antibody (Millipore). For Lamin A/C, Progerin, and Tubulin, cells were collected in Laemmli 1× buffer and stored at −80° C. To lyse, cells were passed through a syringe and boiled at 95° C. for 5 minutes. Proteins were quantified using the Lowry assay. After transfer, membranes were probed with anti-Lamin antibody (Santa Cruz Biotech sc-6215), recognizing both Lamin isoforms A and C, and Progerin and anti-Tubulin antibody (Millipore).

FACS analysis: For cell cycle analysis, the medium supernatant was saved and spun down with trypsinized cells, fixed in 75% ethanol and stained with Propidium Iodine (PI, Sigma, 50 μg/ml) and RNase A (Sigma, 250 μg/ml) solution in 1×PBS. For caspase-3 cleavage analysis by FACS, the medium supernatant was saved and spun down with trypsinized cells, fixed in 1% formamide on ice for 20 minutes, stored in 75% ethanol, stained with Caspase-3 antibody (Cell Signaling 9661) and subsequently conjugated to the fluorophore FITC (anti rabbit FITC, ImmunoJackson), and stained with PI/RNase A solution. Samples were analyzed on a BD Facs Cantoll, using a 488 nm laser and 530/30 filter for FITC, and 670 nm laser and 585/42 filter for PI. Acquisition was performed with the software BDFacsDIVA v6.1.1, and analysis was done using software ModfitLT3.0. For Sub G-1 and caspase positive cells, at least 500 events were analyzed per sample. For cell cycle, at least 8000 events were analyzed per sample.

Naked Delivery: Oligonucleotides in PBS were added straight to plated cells, while mock-treated cells were given only PBS. A constant amount of PBS was used per condition in each experiment.

Retroviral infection: BJ cells were transduced with a retroviral vector expressing either wild type LaminA or mutant Progerin gene and selected with puromycin.

In vivo treatment of the G292 xenografts: CD-1 nude male mice, from Charles River Italy were maintained in cages using steam autoclaved (sterile) bedding, γ-radiated diet and acidified mineral water.

$10 \times 10^6$ G-292 cells were injected subcutaneously into the left flank of nude male mice at day 0. Animals were examined regularly for the appearance of tumors. When tumors had reached a volume of 90 to 220 mm$^3$, mice were randomized and assigned to treatment groups, with a target of 7 mice per group. When treatment starts the mean tumor volume was about 0.14 cm$^3$. Treatments were administered intraperitoneally at a dose of 15 mg/kg at day 13, 17, 21, 25 for PBS and Tiny anti TeloC, day 13 and 17 for PS anti TeloC.

All procedures adopted for housing and handling of animals were in strict compliance with Italian and European guidelines for Laboratory Animal Welfare. Body weight at the day of tumor implant: g. 25-38.

In vivo treatment of the Tert mutant zebrafish: Heterozygous telomerase mutant zebrafish (Tert+/−, http://www.ncbi.nlm.nih.gov/pmc/articles/PMC2762901/) were incrossed and the eggs were injected at one cell stage with 0.5 ng/μl of PS LNA into the yolk. The injected fish were raised to adulthood in the nursery and then genotyped by fin clips to identify the homozygous mutant fish (Generation 1 tert−/−), which were incrossed and their offspring (Generation 2) was analyzed for survival rate and phenotype.

In vivo treatment of HGPS mice: HGPS mice expressing the progerin in epidermal keratinocytes (McKenna et al, Aging cell 2014) were intraperitoneally injected with the PS LNA oligonucleotides at a concentration of 15 mg/Kg every 3-4 days starting at embryonic day 17.5.

Antisense Oligonucleotides:

LNA sequences: The LNA oligonucleotides were produced by Exiqon.

LNA with a phosphate backbone (FIGS. 4, 5, 6):

```
Control
                                            (SEQ ID No. 19)
ACTGATAGGGAGTGGTAAACT Anti TeloG
                                            (SEQ ID No. 20)
CCCTAACCCTAACCCTAACCC Anti TeloC
                                            (SEQ ID No. 21)
GGGTTAGGGTTAGGGTTAGGG
```

LNA with a fully phosphorothioate backbone (LNA-PS) (FIGS. 7, 8, 10, 11, 12, 13, 14, 16, 17, 18, 19, 20, 21, 22, 24, 25, 26, 27, 28, 29, 30, 31):

```
(* signifies phosphorothioate modification)
PS Control
                                            (SEQ ID No. 19)
A*C*T*G*A*T*A*G*G*G*A*G*T*G*G*T*A*A*A*C*T PS Anti TeloG
                                            (SEQ ID No. 20)
C*C*C*T*A*A*C*C*C*T*A*A*C*C*C*T*A*A*C*C*C PS Anti TeloC
                                            (SEQ ID No. 21)
G*G*G*T*T*A*G*G*G*T*T*A*G*G*G*T*T*A*G*G*G
```

Tiny (8-mer) LNA with a fully phosphorothioate backbone (FIGS. 10, 11, 12, 13, 15, 16, 17, 24, 25, 26, 27, 28, 29):

```
Tiny Control
                                    (SEQ ID No. 22)
C*G*T*C*A*T*A*C Tiny Anti TeloG
              (nt 1 to 8 of SEQ ID No. 20)
C*C*C*T*A*A*C*C Tiny Anti TeloC
              (nt 1 to 8 of SEQ ID No. 21)
G*G*G*T*T*A*G*G
```

2'-O-Methyl oligonucleotides (FIGS. 30, 31): The 2'-O-Methyl oligonucleotides were produced by Integrated DNA Technologies.

(* signifies phosphorothioate modification; m signifies methyl group modification on 2' position)

```
2'-O-Me Control:
                                    (SEQ ID No. 34)
mU*mU*mA*mU*mC*mC*mG*mC*mU*mC*mA* mC*mA*mA*mU*mU*mC*mC*mA*mC*mA*mU

2'-O-Me Anti TeloG:
                                    (SEQ ID No. 20)
mC*mC*mC*mT*mA*mA*mC*mC*mC*mT*mA* mA*mC*mC*mC*mT*mA*mA*mC*mC*mC

2'-O-Me Anti TeloC:
                                    (SEQ ID No. 21)
mG*mG*mG*mT*mT*mA*mG*mG*mG*mT* mT*mA*mG*mG*mG*mT*mT*mA*mG*mG* mG
```

Statistical analysis: Results are shown as mean plus or minus standard deviation or standard error of the mean. P value was calculated by Student's two-tailed t-test, Chi-square test, Mann Whitney test or Mantel-Cox test, as appropriate.

Results

The inventors measured the levels of DDRNAs generated at damaged telomeres by qPCR. To do so, they used mouse embryonic fibroblasts (MEFs) in which telomeres can be deprotected by knocking out the telomere binding protein TRF2 (Celli and de Lange, 2005). This leads to the activation of DDR at virtually all telomeres. This is an accepted model of telomere dysfunction. It has already been shown that, when the DNA is damaged, small RNA molecules named DDRNAs are generated at that specific damaged locus, and that they carry the same sequence of the damaged DNA (Francia et al., 2012); thus the inventors reasoned that two different sets of molecules of DDRNAs could be generated upon telomere deprotection, a set deriving from the transcription of the G-rich telomeric DNA strand (TeloC DDRNA) and a set deriving from the transcription of the C-rich telomeric DNA strand (TeloG DDRNA; FIG. 1). By RT-qPCR and by targeted sequencing of small RNA, they were able to detect a reproducible two to three fold increase of both TeloC and TeloG DDRNAs in cells with deprotected telomeres, compared with control cells with normal telomeres (FIG. 2).

In cells with deprotected telomeres, both TeloG and TeloC DDRNA precursor transcripts were strongly induced when compared to control cells (FIG. 23*a*), indicating that telomere deprotection induces transcription at telomeres.

ALT-positive cells display a strong chronic DDR activation at the telomeres (Cesare and Reddel, 2010). The inventors discovered that this correlates with higher levels of tDDRNAs, as detected by RT-qPCR, in ALT-positive WI-38 VA-13, compared with their parental cell line, WI-38 human fibroblasts, and in the ALT-positive SW26 compared with the telomerase-positive SW39 fetal lung fibroblasts, which are cell lines immortalized from the same fibroblast cell line, IMR90, resulting in different telomere maintenance mechanisms (Bechter et al., 2003) (FIG. 3). In addition, both TeloG and TeloC DDRNA precursor transcripts were also strongly upregulated in SW26 ALT-positive cells compared to control SW39 cells (FIG. 23*b*).

ALT-positive cells rely on the homologous recombination mechanism to maintain their telomeres (Cesare and Reddel, 2010); thus the inventors tested whether they are hypersensitive to DDRNA inhibition.

The inventors transfected an ALT cell line, U-2 OS human osteosarcoma cells, with locked nucleic acid (LNA) (Veedu and Wengel, 2010) molecules targeting either the G or the C-rich telomeric transcripts (anti TeloG and anti TeloC, respectively), or a control LNA, and the inventors monitored the cell growth for ten days. The growth of the cells transfected with the control and the anti TeloG LNA did not differ from the mock-treated cells; differently, the anti TeloC LNA significantly impaired U-2 OS growth (FIG. 4).

The effect is specific for ALT cells, since the anti TeloC LNA did not have a significant impact on growth rate of telomerase-expressing human fibroblast cells, either transformed (BJ ELR), or normal (BJ hTERT) (FIG. 4).

To monitor the impact of LNA treatment on ALT biomarkers, the inventors evaluated the presence of ALT-associated PML bodies (APBs), nuclear structures containing recombination factors and telomeric DNA specific of ALT cells (Henson and Reddel, 2010). By an indirect immunostaining against the PML protein, the inventors observed a decrease of APBs in U-2 OS cells treated with the anti TeloC LNA, compared with the control or the anti TeloG LNA (FIG. 5).

In order to extend their observations, the inventors transfected the ALT-positive cell lines U-2 OS, Saos-2 and WI-38 VA-13 with anti TeloG and anti TeloC LNA. The anti TeloC LNA significantly inhibited the cell growth in all three cell lines tested (FIG. 6).

The phosphorothioate backbone ("PS") is a modification that makes an oligonucleotide more resistant to nuclease degradation and that is commonly used to enhance the activity of oligonucleotides, especially in vivo. The inventors designed LNA molecules that have the same sequence of the phosphodiester LNA, but with a fully phosphorothioate backbone (PS LNA, see Material and Methods). The PS anti TeloC LNA prevents U-2 OS cell growth at a concentration of 20 nM, which is 10 times lower than the concentration used for the phosphodiester LNA (FIGS. 7 and 8), while it had a smaller effect on BJ hTERT cells, used as a control.

So called "tiny/short LNA oligonucleotides", which are at least 6nt, preferably at least 8nt long fully LNA oligonucleotides, have been shown to target specifically their complementary RNA target, both in vitro and in vivo (Obad et al., 2011). The inventors designed tiny/short LNA oligonucleotides with a phosphorothioate backbone, named "tiny anti TeloC" and "tiny anti TeloG", which are 8 nucleotides in length and target the telomeric transcripts (FIG. 9).

U-2 OS cells transfected with tiny anti TeloC oligonucleotide grew significantly less than mock transfected cells or cells transfected with a control or tiny anti TeloG oligonucleotide (FIG. 10). The effect was specific for ALT cells, because the anti TeloC LNA did not impair cell growth in normal human fibroblasts (BJ cells) (FIG. 11). However, the impact of the tiny anti TeloC oligonucleotide on the cell growth was less pronounced in comparison to the PS anti TeloC LNA, used at the same molarity (FIG. 10).

Figure 13:
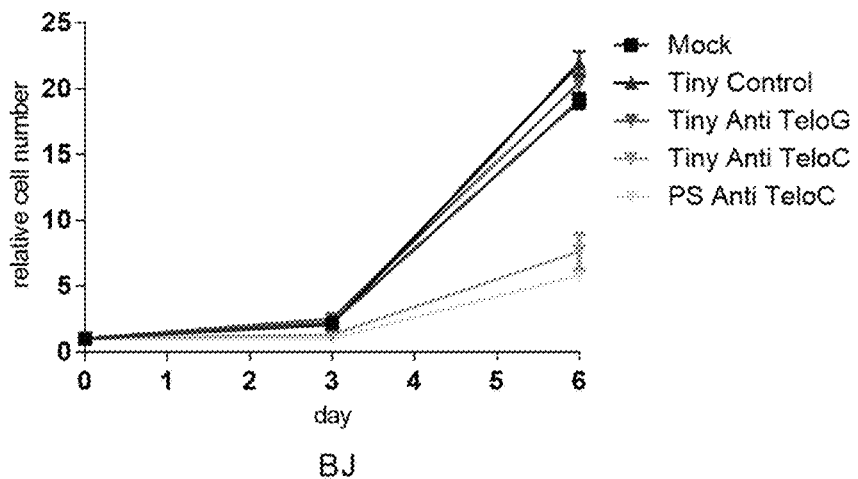
Figure 13:
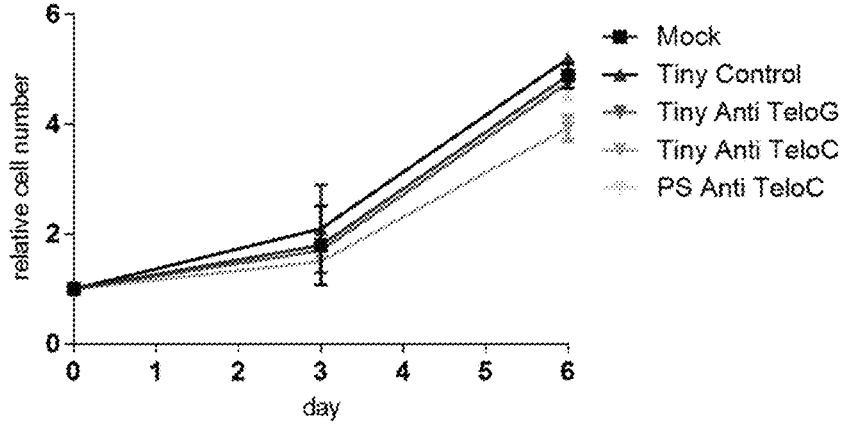

By using a 3-fold higher amount of the tiny LNA oligos (60 nM) proportional to their shorter length and thus to their ability to match a telomeric repeats RNA, the inventors observed an inhibitory effect on ALT cell proliferation of the tiny anti TeloC LNA, similar to the PS anti TeloC LNA at 20 nM concentration (FIG. 12). Also at this higher concentration, the effect of the tiny/short anti TeloC LNA was specific for ALT cells (FIG. 13).

Anti TeloC LNA-mediated growth impairment, by both PS LNA and Tiny LNA, was accompanied by induction of apoptosis, evidenced by caspase-3 cleavage, and increased sub G-1 cells indicative of cell death, as shown by FACS analysis, as well as by caspase-3 and PARP-1 cleavage, as shown by western blot analysis, (FIG. 24). Additionally, U-2 OS cells transfected with anti TeloC LNAs displayed a lengthened S phase (FIG. 25), indicative of exacerbated replication stress, thought to be linked to the ALT mechanism (O'Sullivan and Karlseder, 2010).

To further prove the specificity of anti TeloC LNAs, the inventors tested the effect of LNA transfection on paired cell lines SW26 (ALT) and SW39 (telomerase-positive), described previously. The anti TeloC LNAs inhibited growth of ALT cells much more than the matched non-ALT controls (FIG. 26).

As transfection of cells can be achieved in vitro, but not in vivo, it is important to test the ability of cells to uptake "naked" LNA, with no transfection agent. This process is termed "gymnotic delivery," and is believed to be a better predictor of the effectiveness of a treatment in vivo (Stein et al., 2010). Thus, the inventors sought to determine the efficacy of naked delivery of LNAs in multiple ALT cell lines.

Naked Delivery of LNAs was effective in U-2 OS cells, both PS anti TeloC LNA and Tiny anti TeloC LNA inhibited cell growth (FIG. 27 A, B). Meanwhile, the control- and anti TeloG-treated cells were relatively unaffected.

In order to demonstrate that the efficacy of the phosphorothioate backbone oligonucleotides was not restricted to the osteosarcoma cell lines, the inventors tested them on another cell type, the ALT-positive glioblastoma cell line GBM14 (Heaphy et al., 2011) by naked delivery. Only the PS anti TeloC and tiny anti TeloC LNA significantly reduced cell growth compared to untreated cells (FIG. 14, 15).

Another ALT-positive cell line, G-292, is capable of growing as a xenograft in mice (Lauvrak et al., 2013). The inventors first determined that this cell line was also affected by only anti TeloC LNA and not controls (FIG. 28). Then, they determined the efficacy of naked delivery, finding that PS anti TeloC and Tiny anti TeloC were capable of inhibiting growth, while the respective controls PS anti TeloG, Tiny Control, and Tiny anti TeloG had no effect (FIG. 29).

To test the efficacy of the ASO treatment on the growth of ALT-positive tumors in vivo, G-292 cells were injected into the flank of nude mice, until they formed a detectable tumor mass. Tumor-bearing mice were treated intraperitoneally with ASOs. Both the PS anti TeloC and the tiny anti TeloC reduced the tumor growth compared to the vehicle (PBS)-injected mice (FIG. 16). The inventors did not perform a maximum tolerated dose study, therefore it is possible that a higher dose could have a stronger inhibitory effect on tumor growth. In addition, the PS anti TeloC and the tiny anti TeloC increased the time needed for the tumor to reach the size of 1 $cm^3$ (FIG. 17).

The inventors tested the efficacy and the specificity of another class of ASOs, 2'-O-Methyl (2'-O-Me) ASOs with a phosphorothioate backbone. Only U-2 OS transfected with 2'-O-Me anti-TeloC grew significantly less than mock-transfected cells, while control and anti-TeloG ASO did not affect cell growth (FIG. 30). Importantly, when used at the same concentration (20 nM), 2'-O-Me anti-TeloC effect on cell growth was greater than PS anti TeloC. Differently, 2'-O-Me anti-TeloC did not impair BJ cells growth. Additionally, 2'-O-Me ASOs were not toxic up to 100 nM (FIG. 31).

Non-Cancer Conditions Associated with Telomere Dysfunction

Genetic inactivation of telomerase functions in fish *Danio rerio* (zebrafish) induces telomere dysfunction and a number of pathological events recapitulating ageing in an accelerated form (Anchelin et al., 2013; Carneiro et al., 2016). Therefore this is an established faithful vertebrate model of telomere dysfunction, in particular of physiological ageing. Second-generation telomerase-mutant zebrafish animals were studied because of a stronger phenotype compared to first generation zebrafish. The animals are characterized by morphological defects and shorter lifespan and animals die few days after birth. PS LNA were injected in one-cell embryos from first generation telomerase mutant fish, which were crossed to obtain a second generation. The fish born from individuals treated with either anti TeloC or anti TeloG showed a significant reduction of the morphological defects associated with premature ageing (FIG. 18) and survived longer (FIG. 19).

The inventors infected normal human fibroblasts with a vector expressing the mutated form of the Lamin A gene, also known as progerin (Gonzalo et al., 2016) or the wild-type Lamin A gene as control. This gene is mutated in the HGPS patients and its expression leads to a slow down of the cell growth and to premature senescence, recapitulating the premature ageing phenotype observed in telomere syndrome such as the HGPS patients. The progerin expression has been shown to cause telomere dysfunction (Chojnowski et al., 2015). The inventors monitored the cell growth of these cells upon PS LNA transfection. In the presence of either PS anti TeloC or PS anti TeloG, the progerin-expressing cells grew more than cells mock transfected or transfected with the PS control LNA, as monitored by BrdU incorporation and expression of the proliferation marker KI67 (FIG. 20), despite similar levels of progerin expression (FIG. 21). These results suggest that ASOs targeting tDDRNAs are able to prevent the progerin-induced senescence establishment.

A HGPS mouse model, which expresses the progerin in epidermal keratinocytes shows epidermal hyperplasia, severe skin abnormalities, hair thinning, marked hyperkeratosis, moderate fibrosis of the dermis, infiltration by inflammatory cells and they die within the first two postnatal weeks (McKenna et al., 2014). The inventors treated the progerin-expressing and wild-type mice with PS anti TeloG LNA once during pregnancy, injecting the pregnant females, and every 3 days after birth. The treatment with the anti TeloG significantly prolonged the lifespan of progeric mice, compared with untreated animals (FIG. 22).

REFERENCES

Anchelin, M., Alcaraz-Perez, F., Martinez, C. M., Bernabe-Garcia, M., Mulero, V., and Cayuela, M. L. (2013). Premature aging in telomerase-deficient zebrafish. Dis Model Mech 6, 1101-1112.

Armanios, M., and Blackburn, E. H. (2012). The telomere syndromes. Nature reviews Genetics 13, 693-704.

Azzalin, C. M., Reichenbach, P., Khoriauli, L., Giulotto, E., and Lingner, J. (2007). Telomeric repeat containing RNA and RNA surveillance factors at mammalian chromosome ends. Science 318, 798-801.

Bechter, O. E., Zou, Y., Shay, J. W., and Wright, W. E. (2003). Homologous recombination in human telomerase-positive and ALT cells occurs with the same frequency. EMBO Rep 4, 1138-1143.

Begg, A. C., Stewart, F. A., and Vens, C. (2011). Strategies to improve radiotherapy with targeted drugs. Nat Rev Cancer 11, 239-253.

Benson, E. K., Lee, S. W., and Aaronson, S. A. (2010). Role of progerin-induced telomere dysfunction in HGPS premature cellular senescence. J Cell Sci 123, 2605-2612.

Carneiro, M. C., Henriques, C. M., Nabais, J., Ferreira, T., Carvalho, T., and Ferreira, M. G. (2016). Short Telomeres in Key Tissues Initiate Local and Systemic Aging in Zebrafish. PLoS Genet 12, e1005798.

Cawthon, R. M. (2002). Telomere measurement by quantitative PCR. Nucleic Acids Res 30, e47.

Celli, G. B., and de Lange, T. (2005). DNA processing is not required for ATM-mediated telomere damage response after TRF2 deletion. Nat Cell Biol 7, 712-718.

Cesare, A. J., and Reddel, R. R. (2010). Alternative lengthening of telomeres: models, mechanisms and implications. Nat Rev Genet 11, 319-330.

Chojnowski, A., Ong, P. F., Wong, E. S., Lim, J. S., Mutalif, R. A., Navasankari, R., Dutta, B., Yang, H., Liow, Y. Y., Sze, S. K., et al. (2015). Progerin reduces LAP2alpha-telomere association in Hutchinson-Gilford progeria. Elife 4.

d'Adda di Fagagna, F. (2008). Living on a break: cellular senescence as a DNA-damage response. Nat Rev Cancer 8, 512-522.

d'Adda di Fagagna, F., Reaper, P. M., Clay-Farrace, L., Fiegler, H., Carr, P., Von Zglinicki, T., Saretzki, G., Carter, N. P., and Jackson, S. P. (2003). A DNA damage checkpoint response in telomere-initiated senescence. Nature 426, 194-198.

Durant, S. T. (2012). Telomerase-independent paths to immortality in predictable cancer subtypes. J Cancer 3, 67-82.

Feng, F. Y., de Bono, J. S., Rubin, M. A., and Knudsen, K. E. (2015). Chromatin to Clinic: The Molecular Rationale for PARP1 Inhibitor Function. Mol Cell 58, 925-934.

Flynn, R. L., Cox, K. E., Jeitany, M., Wakimoto, H., Bryll, A. R., Ganem, N. J., Bersani, F., Pineda, J. R., Suva, M. L., Benes, C. H., et al. (2015). Alternative lengthening of telomeres renders cancer cells hypersensitive to ATR inhibitors. Science 347, 273-277.

Francia, S., Michelini, F., Saxena, A., Tang, D., de Hoon, M., Anelli, V., Mione, M., Carninci, P., and d'Adda di Fagagna, F. (2012). Site-specific DICER and DROSHA RNA products control the DNA-damage response. Nature 488, 231-235.

Fumagalli, M., Rossiello, F., Clerici, M., Barozzi, S., Cittaro, D., Kaplunov, J. M., Bucci, G., Dobreva, M., Matti, V., Beausejour, C. M., et al. (2012). Telomeric DNA damage is irreparable and causes persistent DNA-damage-response activation. Nat Cell Biol 14, 355-365.

Gonzalo, S., Kreienkamp, R., and Askjaer, P. (2016). Hutchinson-Gilford Progeria Syndrome: A premature aging disease caused by LMNA gene mutations. Ageing Res Rev.

Gray, K., Kumar, S., Figg, N., Harrison, J., Baker, L., Mercer, J., Littlewood, T., and Bennett, M. (2015). Effects of DNA damage in smooth muscle cells in atherosclerosis. Circ Res 116, 816-826.

Hahn, W. C., Counter, C. M., Lundberg, A. S., Beijersbergen, R. L., Brooks, M. W., and Weinberg, R. A. (1999). Creation of human tumour cells with defined genetic elements. Nature 400, 464-468.

Heaphy, C. M., de Wilde, R. F., Jiao, Y., Klein, A. P., Edil, B. H., Shi, C., Bettegowda, C., Rodriguez, F. J., Eberhart, C. G., Hebbar, S., et al. (2011). Altered telomeres in tumors with ATRX and DAXX mutations. Science 333, 425.

Henriques, C. M., Carneiro, M. C., Tenente, I. M., Jacinto, A., and Ferreira, M. G. (2013). Telomerase is required for zebrafish lifespan. PLoS Genet 9, e1003214.

Henson, J. D., and Reddel, R. R. (2010). Assaying and investigating Alternative Lengthening of Telomeres activity in human cells and cancers. FEBS letters 584, 3800-3811.

Herbig, U., Ferreira, M., Condel, L., Carey, D., and Sedivy, J. M. (2006). Cellular senescence in aging primates. Science 311, 1257.

Herbig, U., Jobling, W. A., Chen, B. P., Chen, D. J., and Sedivy, J. M. (2004). Telomere shortening triggers senescence of human cells through a pathway involving ATM, p53, and p21(CIP1), but not p16(INK4a). Mol Cell 14, 501-513.

Hewitt, G., Jurk, D., Marques, F. D., Correia-Melo, C., Hardy, T., Gackowska, A., Anderson, R., Taschuk, M., Mann, J., and Passos, J. F. (2012). Telomeres are favoured targets of a persistent DNA damage response in ageing and stress-induced senescence. Nat Commun 3, 708.

Hogrefe, R. I. (1999). An antisense oligonucleotide primer. Antisense Nucleic Acid Drug Dev 9, 351-357.

Hu, J., Hwang, S. S., Liesa, M., Gan, B., Sahin, E., Jaskelioff, M., Ding, Z., Ying, H., Boutin, A. T., Zhang, H., et al. (2012). Antitelomerase therapy provokes ALT and mitochondrial adaptive mechanisms in cancer. Cell 148, 651-663.

Jackson, S. P., and Bartek, J. (2009). The DNA-damage response in human biology and disease. Nature 461, 1071-1078.

Janssen, H. L., Reesink, H. W., Lawitz, E. J., Zeuzem, S., Rodriguez-Torres, M., Patel, K., van der Meer, A. J., Patick, A. K., Chen, A., Zhou, Y., et al. (2013). Treatment of HCV infection by targeting microRNA. N Engl J Med 368, 1685-1694.

Jiang, W. Q., Zhong, Z. H., Henson, J. D., Neumann, A. A., Chang, A. C., and Reddel, R. R. (2005). Suppression of alternative lengthening of telomeres by Sp100-mediated sequestration of the MRE11/RAD50/NB S1 complex. Mol Cell Biol 25, 2708-2721.

Jiang, W. Q., Zhong, Z. H., Henson, J. D., and Reddel, R. R. (2007). Identification of candidate alternative lengthening of telomeres genes by methionine restriction and RNA interference. Oncogene 26, 4635-4647.

Kamranvar, S. A., Chen, X., and Masucci, M. G. (2013). Telomere dysfunction and activation of alternative lengthening of telomeres in B-lymphocytes infected by Epstein-Barr virus. Oncogene 32, 5522-5530.

Kelley, M. R., Logsdon, D., and Fishel, M. L. (2014). Targeting DNA repair pathways for cancer treatment: what's new? Future Oncol 10, 1215-1237.

Kudlow, B. A., Stanfel, M. N., Burtner, C. R., Johnston, E. D., and Kennedy, B. K. (2008). Suppression of proliferative defects associated with processing-defective lamin A mutants by hTERT or inactivation of p53. Mol Biol Cell 19, 5238-5248.

Lauvrak, S. U., Munthe, E., Kresse, S. H., Stratford, E. W., Namlos, H. M., Meza-Zepeda, L. A., and Myklebost, O. (2013). Functional characterisation of osteosarcoma cell lines and identification of mRNAs and miRNAs associated with aggressive cancer phenotypes. Br J Cancer 109, 2228-2236.

Lee, M., Hills, M., Conomos, D., Stutz, M. D., Dagg, R. A., Lau, L. M., Reddel, R. R., and Pickett, H. A. (2014). Telomere extension by telomerase and ALT generates variant repeats by mechanistically distinct processes. Nucleic Acids Res 42, 1733-1746.

Li, Z., and Rana, T. M. (2014). Therapeutic targeting of microRNAs: current status and future challenges. Nat Rev Drug Discov 13, 622-638.

Lu, Y., Leong, W., Guerin, O., Gilson, E., and Ye, J. (2013). Telomeric impact of conventional chemotherapy. Front Med 7, 411-417.

McKenna, T., Rosengardten, Y., Viceconte, N., Baek, J. H., Grochova, D., and Eriksson, M. (2014). Embryonic expression of the common progeroid lamin A splice mutation arrests postnatal skin development. Aging Cell 13, 292-302.

Monteleone, G., Neurath, M. F., Ardizzone, S., Di Sabatino, A., Fantini, M. C., Castiglione, F., Scribano, M. L., Armuzzi, A., Caprioli, F., Sturniolo, G. C., et al. (2015). Mongersen, an oral SMAD7 antisense oligonucleotide, and Crohn's disease. N Engl J Med 372, 1104-1113.

Muller, S., and Rodriguez, R. (2014). G-quadruplex interacting small molecules and drugs: from bench toward bedside. Expert Rev Clin Pharmacol 7, 663-679.

Neidle, S. (2010). Human telomeric G-quadruplex: the current status of telomeric G-quadruplexes as therapeutic targets in human cancer. FEBS J 277, 1118-1125.

O'Sullivan, R. J., and Karlseder, J. (2010). Telomeres: protecting chromosomes against genome instability. Nat Rev Mol Cell Biol 11, 171-181.

Obad, S., dos Santos, C. O., Petri, A., Heidenblad, M., Broom, O., Ruse, C., Fu, C., Lindow, M., Stenvang, J., Straarup, E. M., et al. (2011). Silencing of microRNA families by seed-targeting tiny LNAs. Nat Genet 43, 371-378.

Opresko, P. L., and Shay, J. W. (2016). Telomere-associated aging disorders. Ageing Res Rev.

Page, D. T., and Cudmore, S. (2001). Innovations in oral gene delivery: challenges and potentials. Drug Discov Today 6, 92-101.

Pollex, R. L., and Hegele, R. A. (2004). Hutchinson-Gilford progeria syndrome. Clin Genet 66, 375-381.

Potts, P. R., and Yu, H. (2007). The SMCS/6 complex maintains telomere length in ALT cancer cells through SUMOylation of telomere-binding proteins. Nat Struct Mol Biol 14, 581-590.

Ruden, M., and Puri, N. (2013). Novel anticancer therapeutics targeting telomerase. Cancer Treat Rev 39, 444-456.

Rudolph K L, Chang S, Millard M, Schreiber-Agus N, DePinho R A. (2000). Inhibition of experimental liver cirrhosis in mice by telomerase gene delivery. Science. 287(5456): 1253-8.

Salvati, E., Rizzo, A., Iachettini, S., Zizza, P., Cingolani, C., D'Angelo, C., Porru, M., Mondello, C., Aiello, A., Farsetti, A., et al. (2015). A basal level of DNA damage and telomere deprotection increases the sensitivity of cancer cells to G-quadruplex interactive compounds. Nucleic Acids Res 43, 1759-1769.

Sanjiv, K., Hagenkort, A., Calderon-Montano, J. M., Koolmeister, T., Reaper, P. M., Mortusewicz, O., Jacques, S. A., Kuiper, R. V., Schultz, N., Scobie, M., et al. (2016). Cancer-Specific Synthetic Lethality between ATR and CHK1 Kinase Activities. Cell Rep 14, 298-309.

Satyanarayana A, Wiemann S U, Buer J, Lauber J, Dittmar K E, Wüstefeld T, Blasco M A, Manns M P, Rudolph K L. (2003) Telomere shortening impairs organ regeneration by inhibiting cell cycle re-entry of a subpopulation of cells. EMBO J. 22 (15), 4003-13.

Sissi, C., and Palumbo, M. (2014). Telomeric G-quadruplex architecture and interactions with potential drugs. Curr Pharm Des 20, 6489-6509.

Stein, C. A., Hansen, J. B., Lai, J., Wu, S., Voskresenskiy, A., Hog, A., Worm, J., Hedtjarn, M., Souleimanian, N., Miller, P., et al. (2010). Efficient gene silencing by delivery of locked nucleic acid antisense oligonucleotides, unassisted by transfection reagents. Nucleic Acids Res 38, e3.

Stenvang, J., Petri, A., Lindow, M., Obad, S., and Kauppinen, S. (2012). Inhibition of microRNA function by antimiR oligonucleotides. Silence 3, 1.

Veedu, R. N., and Wengel, J. (2010). Locked nucleic acids: promising nucleic acid analogs for therapeutic applications. Chem Biodivers 7, 536-542.

Wang, J., Uryga, A. K., Reinhold, J., Figg, N., Baker, L., Finigan, A., Gray, K., Kumar, S., Clarke, M., and Bennett, M. (2015). Vascular Smooth Muscle Cell Senescence Promotes Atherosclerosis and Features of Plaque Vulnerability. Circulation 132, 1909-1919.

Ward, A., Khanna, K. K., and Wiegmans, A. P. (2015). Targeting homologous recombination, new pre-clinical and clinical therapeutic combinations inhibiting RAD51. Cancer Treat Rev 41, 35-45.

Weber, A. M., and Ryan, A. J. (2015). ATM and ATR as therapeutic targets in cancer. Pharmacol Ther 149, 124-138.

Xi, H., Li, C., Ren, F., Zhang, H., and Zhang, L. (2013). Telomere, aging and age-related diseases. Aging Clin Exp Res 25, 139-146.

Yeager, T. R., Neumann, A. A., Englezou, A., Huschtscha, L. I., Noble, J. R., and Reddel, R. R. (1999). Telomerase-negative immortalized human cells contain a novel type of promyelocytic leukemia (PML) body. Cancer Res 59, 4175-4179.

Zhong, Z. H., Jiang, W. Q., Cesare, A. J., Neumann, A. A., Wadhwa, R., and Reddel, R. R. (2007). Disruption of telomere maintenance by depletion of the MRE11/RAD50/NBS1 complex in cells that use alternative lengthening of telomeres. J Biol Chem 282, 29314-29322.

The invention claimed is:

1. A method for treating a cancer in which a tumor maintains telomere length by an alternative lengthening of telomeres (ALT) mechanism in a subject in need of thereof, the method comprising:
   administering to the subject, an oligonucleotide that is 6-25 nucleotides long and comprises one of the following sequences: (TTAGGG) SEQ ID No. 1, (TAGGGT) SEQ ID No. 2, (AGGGTT) SEQ ID No. 3, (GGGTTA) SEQ ID No. 4, (GGTTAG) SEQ ID No. 5 or (GTTAGG) SEQ ID No. 6 or a complementary sequence thereof or a variant or a mixture thereof, or administering to the subject an oligonucleotide comprising one of the following sequences: (TTAGGG)n, (TAGGGT)n, (AGGGTT)n, (GGGTTA)n, (GGTTAG)n or (GTTAGG)n wherein 1<n<5,
   wherein the variant comprises one of the following sequences: TCAGGG, TTCGGG, GTAGGG, TGAGGG, TTGGGG, TAAGGG, ATAGGG, CTAGGG, TTTGGG or TTAAGGG, and
   wherein the cancer is selected from the group consisting of: soft tissue sarcoma, central nervous system cancer, urinary bladder cancer, adrenal gland or peripheral nervous system cancer, neuroendocrine neoplasms, kidney cancer, lung and pleural cancer, skin cancer, liver cancer, testis cancer, breast cancer, uterus cancer, ovary cancer, gall bladder cancer, oesophagus cancer and osteosarcoma.

2. The method of claim 1, wherein said oligonucleotide is complementary to the sequence of an RNA, said RNA being a RNA transcript synthesized using a specific dysfunctional telomeric DNA as a template for transcription or a fragment of said RNA transcript, said fragment (DDRNA) being generated by processing by Dicer and/or Drosha.

3. The method of claim 1, wherein the cancer is osteosarcoma.

4. The method of claim 1, wherein oligonucleotide comprises a locked nucleic acid (LNA)-modified oligonucleotide, a 2'-O-Methyl-modified oligonucleotide, a phosphorothioate modified oligonucleotide, a phosphorothioate modified locked nucleic acid, a 2'-O-methoxyethyl modified oligonucleotide, a 20-[2-(N-Methylcarbamoyl) ethyl] ribonucleoside, a methylphosphonate, a morpholino oligonucleotide, a LNA-DNA-LNA gapmer oligonucleotide, a mixmer, a Chimeric 2'-O-methyl RNA-DNA gapmer, a N3'-P5' Phosphoroamidate, a 2'-fluoro-arabino nucleic acid, a Phosphoroamidate Morpholino, Cyclohexene nucleic acid, a Tricyclo-DNA, a Peptide nucleic acid, an Unlocked nucleic acid, a Hexitol nucleic acid, a Boranophosphate oligonucleotide, a Phosphoroamidate oligonucleotide.

5. The method of claim 1, further comprising administering at least one additional therapeutic agent, wherein the additional therapeutic agent is an anti-tumoral agent or an anti-emetic agent.

6. The method of claim 5, wherein the additional therapeutic agent is selected from the group consisting of: ATR inhibitor, DDR inhibitor, HR inhibitor, molecule that specifically target telomeres, G-quadruplexes interacting molecules, and a molecule that causes DNA damage generation at telomeres, wherein the molecule that specifically target telomeres and/or causes DNA damage generation at telomeres is selected from G-quadruplex-binding ligands, topoisomerase inhibitors, cisplatin and hydroxyurea.

7. The method of claim 1, further comprising detecting the presence and/or measuring the amount of an RNA,
   wherein said RNA is a RNA transcript synthesized using a specific dysfunctional telomeric DNA as a template for transcription or a fragment of said RNA transcript, said fragment (DDRNA or tDDRNA) being generated by processing by Dicer and/or Drosha, and
   wherein said subject is affected by the cancer.

8. The method of claim 1 wherein the method comprises administering an oligonucleotide comprising (TTAGGG) SEQ ID No. 1, (TAGGGT) SEQ ID No. 2, (AGGGTT) SEQ ID No. 3, (GGGTTA) SEQ ID No. 4, (GGTTAG) SEQ ID No. 5 or (GTTAGG) SEQ ID No. 6 or a complementary sequence thereof or a mixture thereof.

9. The method of claim 1 wherein the method comprises administering an oligonucleotide comprising one of the following sequences: (TTAGGG)n, (TAGGGT)n, (AGGGTT)n, (GGGTTA)n, (GGTTAG)n or (GTTAGG)n wherein 1<n<5.

10. The method of claim 1 wherein the method comprises administering a variant of an oligonucleotide comprising (TTAGGG) SEQ ID No. 1, (TAGGGT) SEQ ID No. 2, (AGGGTT) SEQ ID No. 3, (GGGTTA) SEQ ID No. 4, (GGTTAG) SEQ ID No. 5 or (GTTAGG) SEQ ID No. 6 wherein the variant comprises one of the following sequences: TCAGGG, TTCGGG, GTAGGG, TGAGGG, TTGGGG, TAAGGG, ATAGGG, CTAGGG, TTTGGG or TTAAGGG.

11. The method of claim 1 wherein the oligonucleotide has SEQ ID NO: 21 (GGGTTAGGGTTAGGGTTAGGG).

12. The method of claim 11 wherein the oligonucleotide is a modified LNA phosphorothioate.

* * * * *

SEQUENCE LISTING

<160> NUMBER OF SEQ ID NOS: 34

<210> SEQ ID NO 1
<211> LENGTH: 6
<212> TYPE: DNA
<213> ORGANISM: Artificial Sequence
<220> FEATURE:
<223> OTHER INFORMATION: synthetic

<400> SEQUENCE: 1 ttaggg                                                                    6

<210> SEQ ID NO 2
<211> LENGTH: 6
<212> TYPE: DNA
<213> ORGANISM: Artificial Sequence
<220> FEATURE:
<223> OTHER INFORMATION: synthetic

<400> SEQUENCE: 2 tagggt                                                                    6

<210> SEQ ID NO 3
<211> LENGTH: 6
<212> TYPE: DNA
<213> ORGANISM: Artificial Sequence
<220> FEATURE:
<223> OTHER INFORMATION: synthetic

<400> SEQUENCE: 3 agggtt                                                                    6

<210> SEQ ID NO 4
<211> LENGTH: 6
<212> TYPE: DNA
<213> ORGANISM: Artificial Sequence
<220> FEATURE:
<223> OTHER INFORMATION: synthetic

<400> SEQUENCE: 4 gggtta                                                                    6

<210> SEQ ID NO 5
<211> LENGTH: 6
<212> TYPE: DNA
<213> ORGANISM: Artificial Sequence
<220> FEATURE:
<223> OTHER INFORMATION: synthetic

<400> SEQUENCE: 5 ggttag                                                                    6

<210> SEQ ID NO 6
<211> LENGTH: 6
<212> TYPE: DNA
<213> ORGANISM: Artificial Sequence
<220> FEATURE:
<223> OTHER INFORMATION: synthetic

<400> SEQUENCE: 6 gttagg                                                                    6

<210> SEQ ID NO 7
<211> LENGTH: 23
<212> TYPE: DNA
<213> ORGANISM: Artificial Sequence

```
<220> FEATURE:
<223> OTHER INFORMATION: synthetic

<400> SEQUENCE: 7
tagcaccatt tgaaatcagt gtt                                              23

<210> SEQ ID NO 8
<211> LENGTH: 22
<212> TYPE: DNA
<213> ORGANISM: Artificial Sequence
<220> FEATURE:
<223> OTHER INFORMATION: synthetic

<400> SEQUENCE: 8
cgaattccac aaattgttat cc                                               22

<210> SEQ ID NO 9
<211> LENGTH: 18
<212> TYPE: DNA
<213> ORGANISM: Artificial Sequence
<220> FEATURE:
<223> OTHER INFORMATION: synthetic

<400> SEQUENCE: 9
tagggttagg gttagggt                                                    18

<210> SEQ ID NO 10
<211> LENGTH: 18
<212> TYPE: DNA
<213> ORGANISM: Artificial Sequence
<220> FEATURE:
<223> OTHER INFORMATION: synthetic

<400> SEQUENCE: 10
ccctaaccct aaccctaa                                                    18

<210> SEQ ID NO 11
<211> LENGTH: 18
<212> TYPE: DNA
<213> ORGANISM: Artificial Sequence
<220> FEATURE:
<223> OTHER INFORMATION: synthetic

<400> SEQUENCE: 11
ttcattgtgg gagcagac                                                    18

<210> SEQ ID NO 12
<211> LENGTH: 18
<212> TYPE: DNA
<213> ORGANISM: Artificial Sequence
<220> FEATURE:
<223> OTHER INFORMATION: synthetic

<400> SEQUENCE: 12
cagcagtttc tccagagc                                                    18

<210> SEQ ID NO 13
<211> LENGTH: 18
<212> TYPE: DNA
<213> ORGANISM: Artificial Sequence
<220> FEATURE:
<223> OTHER INFORMATION: synthetic

<400> SEQUENCE: 13
ccctaaccct aaccctaa                                                    18
```

<210> SEQ ID NO 14
<211> LENGTH: 18
<212> TYPE: DNA
<213> ORGANISM: Artificial Sequence
<220> FEATURE:
<223> OTHER INFORMATION: synthetic

<400> SEQUENCE: 14
tagggttagg gttagggt                                              18

<210> SEQ ID NO 15
<211> LENGTH: 39
<212> TYPE: DNA
<213> ORGANISM: Artificial Sequence
<220> FEATURE:
<223> OTHER INFORMATION: synthetic

<400> SEQUENCE: 15
cggtttgttt gggtttgggt ttgggtttgg gtttgggtt                       39

<210> SEQ ID NO 16
<211> LENGTH: 39
<212> TYPE: DNA
<213> ORGANISM: Artificial Sequence
<220> FEATURE:
<223> OTHER INFORMATION: synthetic

<400> SEQUENCE: 16
ggcttgcctt acccttaccc ttaccttac ccttaccct                        39

<210> SEQ ID NO 17
<211> LENGTH: 34
<212> TYPE: DNA
<213> ORGANISM: Artificial Sequence
<220> FEATURE:
<223> OTHER INFORMATION: synthetic

<400> SEQUENCE: 17
agatcggaag agcacacgtc tgaactccag tcac                            34

<210> SEQ ID NO 18
<211> LENGTH: 33
<212> TYPE: DNA
<213> ORGANISM: Artificial Sequence
<220> FEATURE:
<223> OTHER INFORMATION: synthetic

<400> SEQUENCE: 18
acacucuuuc ccuacacgac gcucuuccga ucu                             33

<210> SEQ ID NO 19
<211> LENGTH: 21
<212> TYPE: DNA
<213> ORGANISM: Artificial Sequence
<220> FEATURE:
<223> OTHER INFORMATION: synthetic

<400> SEQUENCE: 19
actgataggg agtggtaaac t                                          21

<210> SEQ ID NO 20
<211> LENGTH: 21
<212> TYPE: DNA
<213> ORGANISM: Artificial Sequence
<220> FEATURE:
<223> OTHER INFORMATION: synthetic

```
<400> SEQUENCE: 20
ccctaaccct aaccctaacc c                                              21

<210> SEQ ID NO 21
<211> LENGTH: 21
<212> TYPE: DNA
<213> ORGANISM: Artificial Sequence
<220> FEATURE:
<223> OTHER INFORMATION: synthetic

<400> SEQUENCE: 21
gggttagggt tagggttagg g                                              21

<210> SEQ ID NO 22
<211> LENGTH: 8
<212> TYPE: DNA
<213> ORGANISM: Artificial Sequence
<220> FEATURE:
<223> OTHER INFORMATION: synthetic

<400> SEQUENCE: 22 cgtcatac                                                              8

<210> SEQ ID NO 23
<211> LENGTH: 21
<212> TYPE: DNA
<213> ORGANISM: Artificial Sequence
<220> FEATURE:
<223> OTHER INFORMATION: synthetic

<400> SEQUENCE: 23
caatcccaat cccaatccca a                                              21

<210> SEQ ID NO 24
<211> LENGTH: 18
<212> TYPE: RNA
<213> ORGANISM: Artificial Sequence
<220> FEATURE:
<223> OTHER INFORMATION: synthetic

<400> SEQUENCE: 24
uuaggguuag gguuaggg                                                  18

<210> SEQ ID NO 25
<211> LENGTH: 42
<212> TYPE: DNA
<213> ORGANISM: Artificial Sequence
<220> FEATURE:
<223> OTHER INFORMATION: synthetic

<400> SEQUENCE: 25
ttagggttag ggttagggtt agggttaggg ttagggttag gg                       42

<210> SEQ ID NO 26
<211> LENGTH: 42
<212> TYPE: DNA
<213> ORGANISM: Artificial Sequence
<220> FEATURE:
<223> OTHER INFORMATION: synthetic

<400> SEQUENCE: 26
aatcccaatc ccaatcccaa tcccaatccc aatcccaatc cc                       42

<210> SEQ ID NO 27
```

```
<211> LENGTH: 18
<212> TYPE: RNA
<213> ORGANISM: Artificial Sequence
<220> FEATURE:
<223> OTHER INFORMATION: synthetic

<400> SEQUENCE: 27
aaucccaauc ccaauccc                                           18

<210> SEQ ID NO 28
<211> LENGTH: 21
<212> TYPE: DNA
<213> ORGANISM: Artificial Sequence
<220> FEATURE:
<223> OTHER INFORMATION: synthetic

<400> SEQUENCE: 28
gttagggtta gggttagggt t                                       21

<210> SEQ ID NO 29
<211> LENGTH: 34
<212> TYPE: DNA
<213> ORGANISM: Artificial Sequence
<220> FEATURE:
<223> OTHER INFORMATION: synthetic

<400> SEQUENCE: 29
gtgactggag ttcagacgtg tgctcttccg atct                         34

<210> SEQ ID NO 30
<211> LENGTH: 58
<212> TYPE: DNA
<213> ORGANISM: Artificial Sequence
<220> FEATURE:
<223> OTHER INFORMATION: synthetic

<400> SEQUENCE: 30
aatgatacgg cgaccaccga gatctacact ctttccctac acgacgctct tccgatct    58

<210> SEQ ID NO 31
<211> LENGTH: 61
<212> TYPE: DNA
<213> ORGANISM: Artificial Sequence
<220> FEATURE:
<223> OTHER INFORMATION: synthetic

<400> SEQUENCE: 31
caagcagaag acggcatacg agatcggtct cggcattcct gctgaaccgc tcttccgatc   60
t                                                             61

<210> SEQ ID NO 32
<211> LENGTH: 58
<212> TYPE: DNA
<213> ORGANISM: Artificial Sequence
<220> FEATURE:
<223> OTHER INFORMATION: synthetic

<400> SEQUENCE: 32
aatgatacgg cgaccaccga gatctacact ctttccctac acgacgctct tccgatct    58

<210> SEQ ID NO 33
<211> LENGTH: 64
<212> TYPE: DNA
<213> ORGANISM: Artificial Sequence
<220> FEATURE:
<223> OTHER INFORMATION: synthetic
```

```
<400> SEQUENCE: 33
caagcagaag acggcatacg agatcgtgat gtgactggag ttcagacgtg tgctcttccg    60
atct                                                                64

<210> SEQ ID NO 34
<211> LENGTH: 22
<212> TYPE: RNA
<213> ORGANISM: Artificial Sequence
<220> FEATURE:
<223> OTHER INFORMATION: synthetic

<400> SEQUENCE: 34
uuauccgcuc acaauuccac au                                            22
```